United States Patent [19]
Ortyn et al.

[11] Patent Number: 5,875,258
[45] Date of Patent: Feb. 23, 1999

[54] BIOLOGICAL SPECIMEN ANALYSIS SYSTEM PROCESSING INTEGRITY CHECKING APPARATUS

[75] Inventors: William E. Ortyn, Devall; Louis R. Piloco; Jon W. Hayenga, both of Kent, all of Wash.

[73] Assignee: NeoPath, Inc., Redmond, Wash.

[21] Appl. No.: 697,480

[22] Filed: Aug. 26, 1996

Related U.S. Application Data

[63] Continuation of Ser. No. 309,249, Sep. 20, 1994, abandoned.

[51] Int. Cl.[6] ................................................. G06K 9/00
[52] U.S. Cl. ...................... 382/133; 382/129; 382/134; 128/922; 359/39
[58] Field of Search ........................ 382/100, 128, 382/129, 130, 131, 132, 133, 134, 181, 224, 226, 321, 325, 270, 145, 147; 128/922; 356/39, 40; 377/10, 11

[56] References Cited

U.S. PATENT DOCUMENTS

| | | | |
|---|---|---|---|
| 3,692,982 | 9/1972 | McMillin | 382/270 |
| 3,824,393 | 7/1974 | Brain . | |
| 4,175,860 | 11/1979 | Bacus . | |
| 4,202,033 | 5/1980 | Strobel . | |
| 4,741,043 | 4/1988 | Bacus | 382/6 |
| 4,887,892 | 12/1989 | Bacus | 350/523 |
| 4,932,044 | 6/1990 | Williams et al. | 377/10 |
| 4,965,725 | 10/1990 | Rutenberg . | |
| 5,007,100 | 4/1991 | D'Aoust et al. . | |
| 5,016,283 | 5/1991 | Bacus et al. | 382/6 |
| 5,018,209 | 5/1991 | Bacus | 382/6 |
| 5,038,216 | 8/1991 | Easterly et al. . | |
| 5,134,662 | 7/1992 | Bacus et al. | 382/6 |
| 5,202,931 | 4/1993 | Bacus | 382/6 |
| 5,235,522 | 8/1993 | Bacus | 364/497 |
| 5,255,085 | 10/1993 | Spence . | |
| 5,257,182 | 10/1993 | Luck et al. . | |
| 5,281,517 | 1/1994 | Bacus et al. | 435/6 |
| 5,287,272 | 2/1994 | Rutenberg et al. . | |
| 5,315,700 | 5/1994 | Johnston et al. . | |
| 5,361,140 | 11/1994 | Hayenga et al. . | |

OTHER PUBLICATIONS

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H. et al., "A Self–Learning Computer Program for Cell Recognition", *ACTA Cytologica: The Journal of Clinical Cytology*, 14:8, pp. 486–494, Oct. 1970.

Smith, Warren J., *Modern Optical Engineering: The Design of Optical Systems*, McGraw–Hill Book Company, pp. 308–325, Copyright 1966.

Tanaka, Noboru et al., "Automated Cytologic Screening System (CYBEST Model 4) : an Integrated Image Cytometry System", Reprinted from *Applied Optics*, vol. 26, pp 3301, Aug. 15, 1987. Copyright © 1987 by the Optical Society of America and reprinted by permission of the copyright owner.

*Primary Examiner*—Bipin Shalwala
*Attorney, Agent, or Firm*—Hans I. Sun; Emil Moffa

[57] ABSTRACT

A suite of tests and parameter monitoring methods for at least five major subsystems that are found in most automated image processing systems, as well as calibration routines for three major system functions. The five areas of subsystem verification include processing quality, illumination quality, image collection quality, autofocus quality, and position quality. An automated biological specimen analysis system uses self measures of system parameters to provide a system status. The system status is reported to the user.

23 Claims, 47 Drawing Sheets

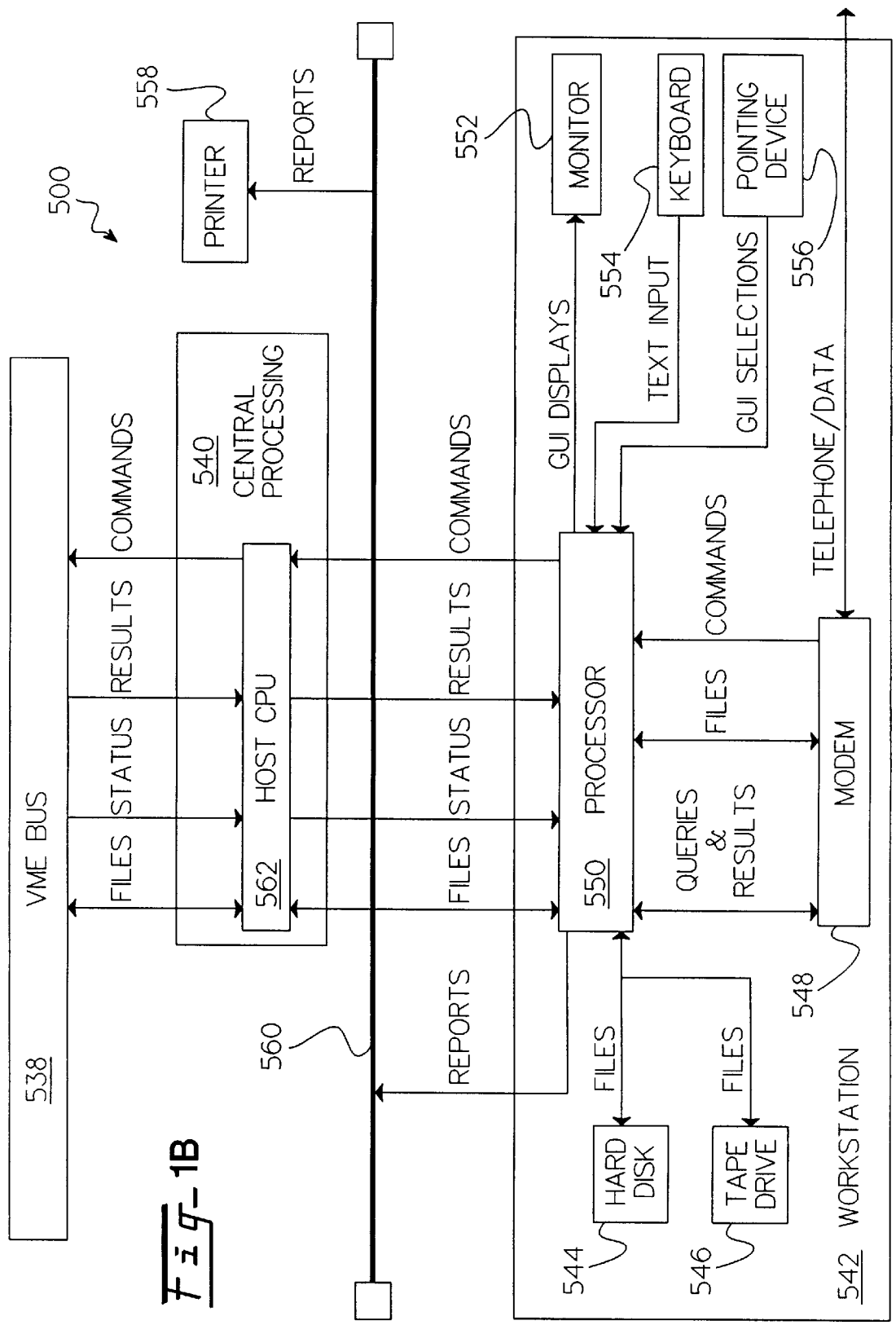

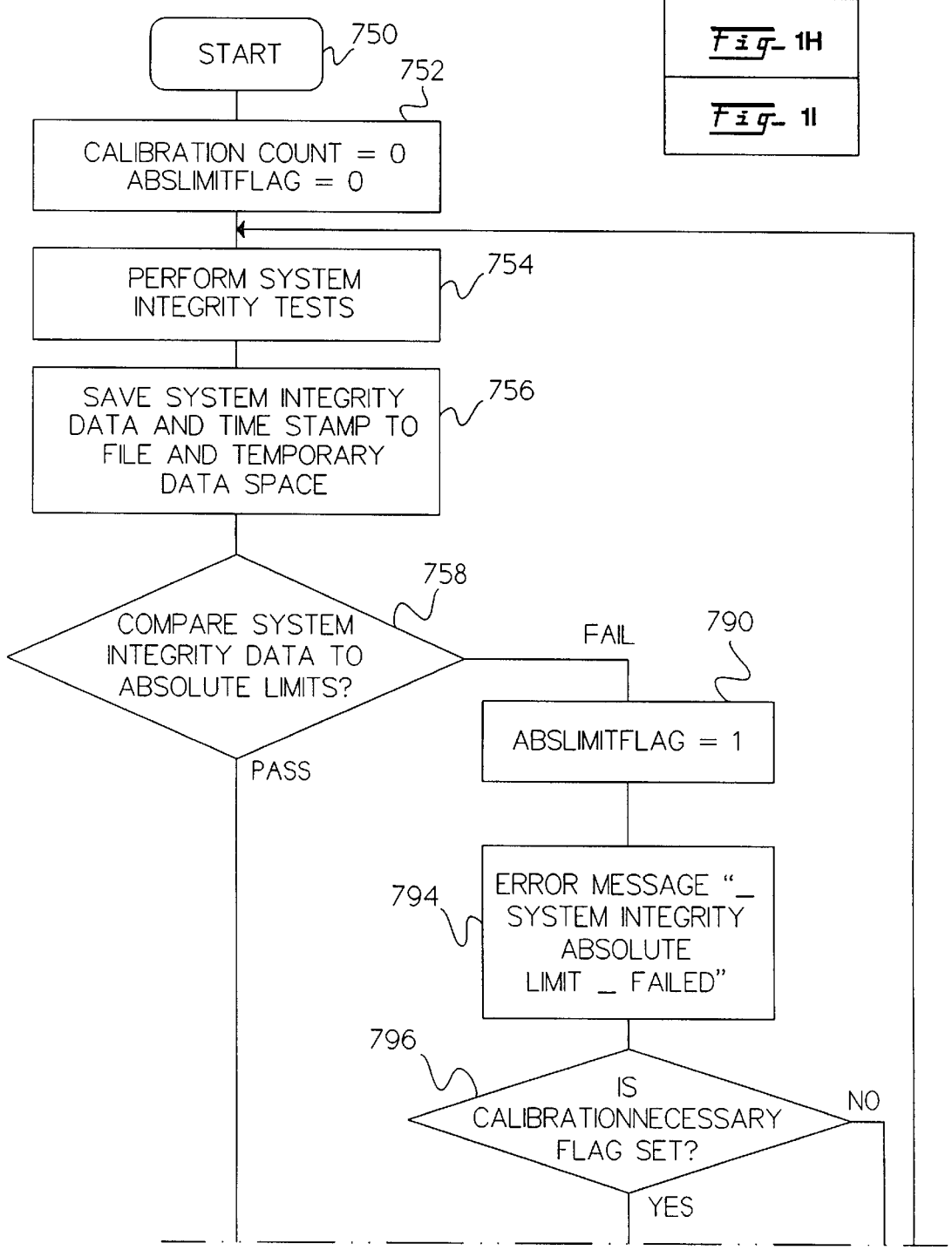

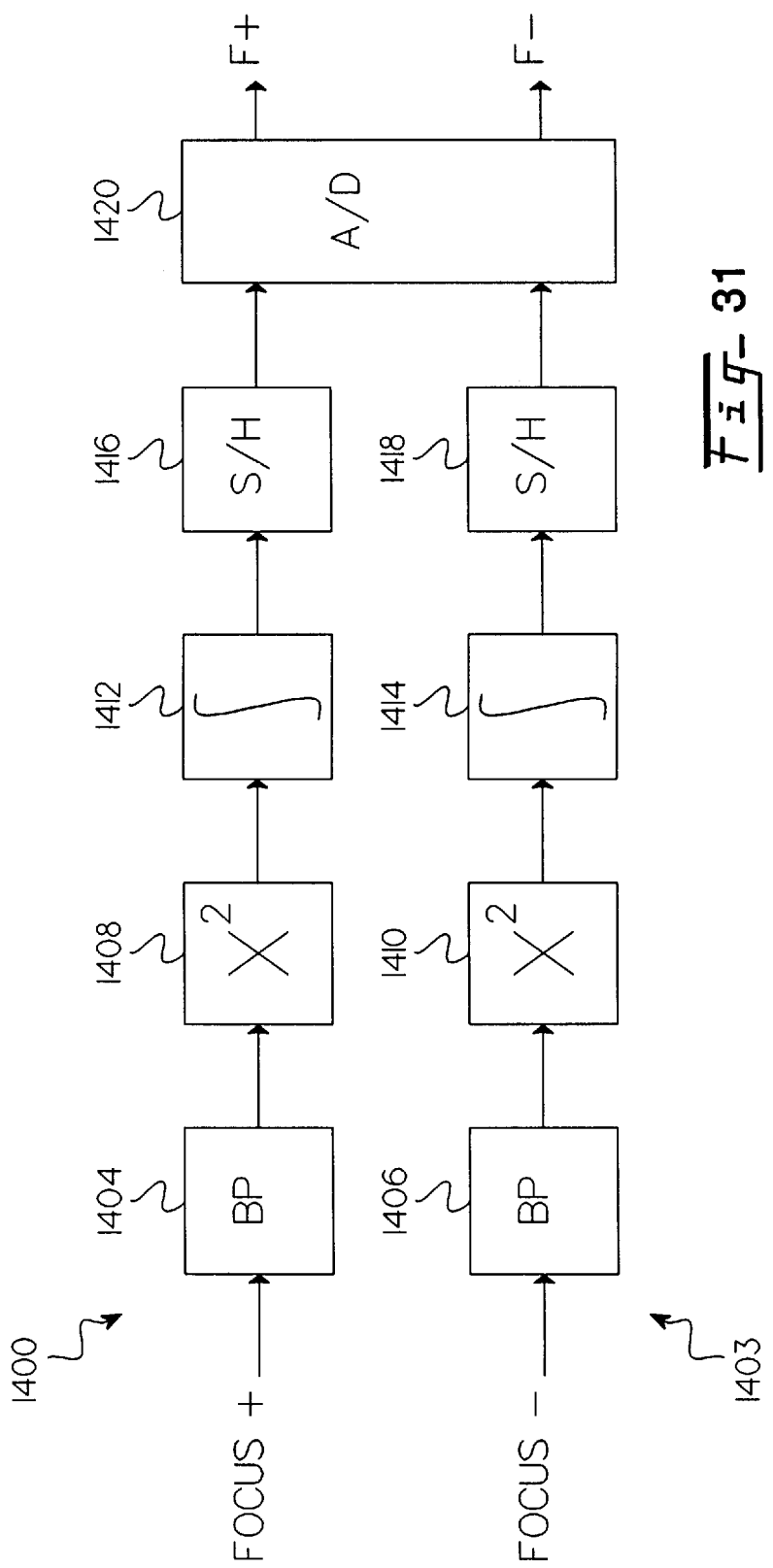

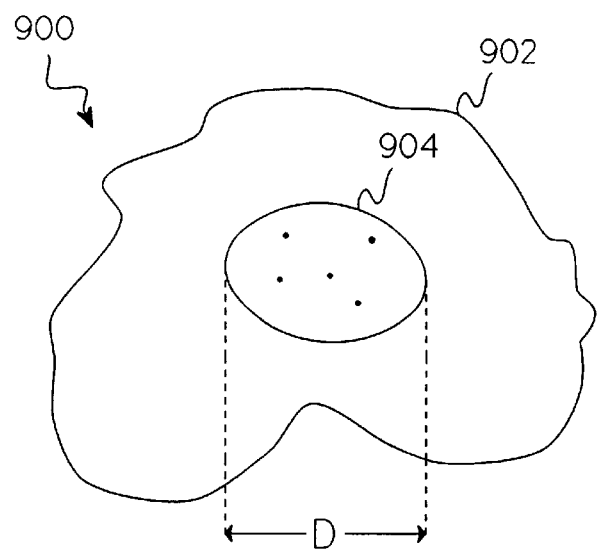
Fig_32
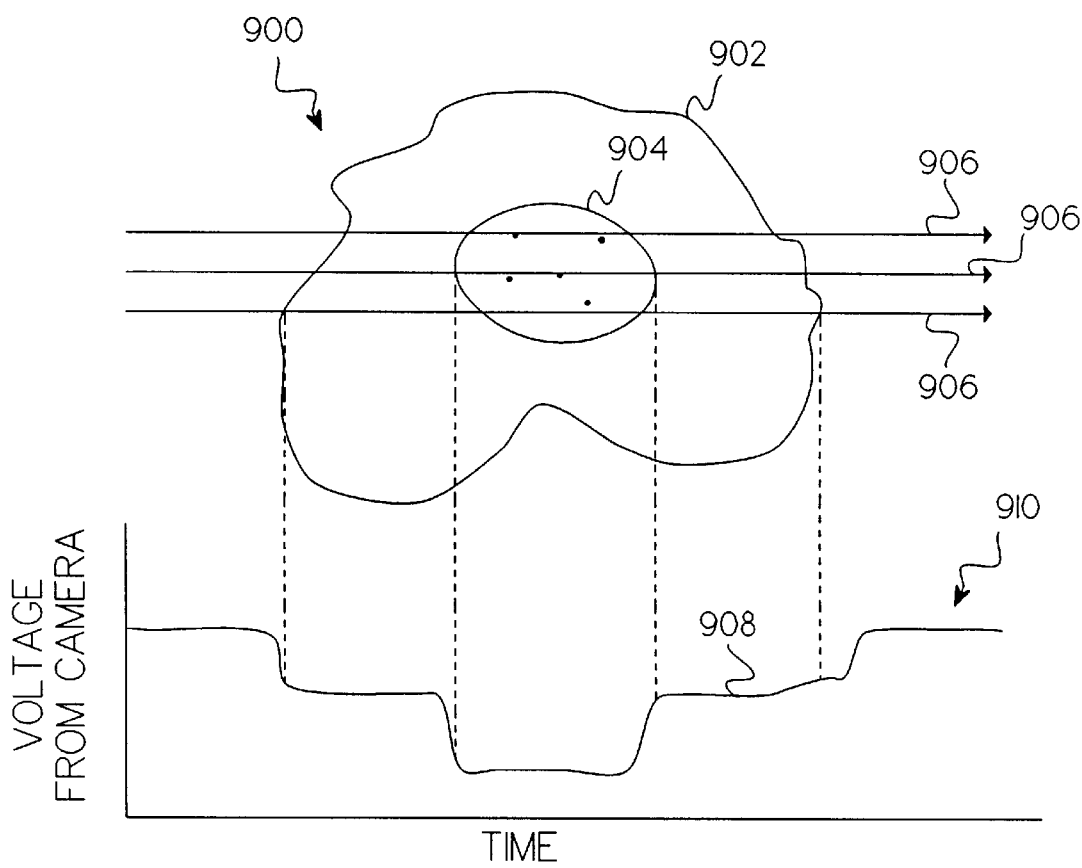
Fig_33

BIOLOGICAL SPECIMEN ANALYSIS SYSTEM PROCESSING INTEGRITY CHECKING APPARATUS

This is a continuation of application Ser. No. 08/309,249, filed on Sep. 20, 1994, now abandoned.

FIELD OF THE INVENTION

The present invention relates to automated scanning systems. More particularly, the present invention relates to a method and apparatus for checking biological specimen system processing integrity in an automated biological specimen analysis system. Still more particularly, the present invention relates to an automated biological specimen analysis system that can test, evaluate and take appropriate action with respect to illumination quality, image collection quality, autofocus system quality, position system quality and processing quality.

BACKGROUND OF INVENTION

Automated cytology instruments are required to perform at a high degree of integrity. Errors caused by such biological specimen analysis systems may have potentially catastrophic effects. Therefore, it is highly desirable for automated biological specimen instruments to monitor themselves at regularly defined intervals. Monitoring may comprise a series of automated tests of each critical subsystem in the instrument.

Generally systems that perform automated scanning have five critical subsystems including illumination, image collection, autofocus, positioning and image processing systems.

In order to achieve a high degree of accuracy and repeatability, such automated biological specimen analysis systems tend to be complex, because they may contain thousands of components. Such complexity demands measuring a large number of parameters to accurately characterize the functionality of such a system. Typically, for instruments manufactured for applications like automated semiconductor wafer and photomask inspection, testing is done at the time of manufacture with stand alone oscilloscopes, spectrum analyzers displacement transducers and the like. Once the instruments pass such tests, they are shipped to customer sites. Typically, problems with these instruments are usually corrected only if they have a major impact on the efficacy of the device. Minor fluctuations in the efficacy of such instruments go unnoticed. It is common practice to run a suite of diagnostic tests only in accordance with regularly scheduled preventative maintenance programs. This may be typically scheduled several times a year. Unfortunately, the instruments are usually taken off line to run such tests and, as a result, productivity suffers. Until the scheduled tests are done, the untested instruments may produce faulty results for months before any problems are caught and rectified.

In addition, standard practice does not facilitate rapid advancement of image processing technologies. Many image processing applications are highly statistical. Therefore large amounts of data must be collected before reasonable conclusions can be drawn. This is particularly true in image processing applications concerning biological specimens where measured features characterizing objects in biological specimens such as, for example, area, perimeter, frequency content, and optical density, among others, vary along a continuum. The standard deviation of any particular feature may be quite large. Further, to obtain accurate, repeatable, and reliable diagnosis of a biological specimen, hundreds of features may be measured for each object in an image. This is further compounded by the fact that thousands of specimens must be evaluated to determine the efficacy of a device. Therefore, image and object feature calculations are taken over the time frame of months. The problem in advancement of image processing technology partially lies in the fact that it is very difficult to know exactly how various system parameters, such as illumination uniformity or image collection frequency response, affect the outcome of various feature calculations. Since standard practice only allows for the measurement of system parameters over long time periods, on the order of months, and requires taking systems scheduled for maintenance out of productivity, to use stand alone equipment, it is nearly impossible to determine system performance at any specific time between maintenance periods. Such uncertainty makes relating system parameters to feature calculation results nearly impossible.

The present invention, for the first time, serves to substantially reduce such reliability problems by providing an automated, on line test to quickly identify any unacceptable deviations in system performance. The apparatus and method of the invention allows formulation of more reliable relationships between system parameters and feature calculations.

The present invention provides an automated method to perform such tests. In accordance with the novel aspects of the invention, testing is done using a test slide containing calibrated clear areas and image primitives that stimulate components of the automated biological specimen analysis system to produce a quantifiable effect. The quantifiable effects are compared to system specifications to ensure that the automated biological specimen system is operating within its engineered limits. If the automated biological specimen analysis system fails to meet these limits, appropriate action is taken. Failing a test may result, for example, in invalidation of all slide results produced since the last acceptable system integrity testing sequence.

SUMMARY OF THE INVENTION

The method and apparatus of the invention comprises a suite of tests and parameter monitoring methods for at least five major subsystems that are found in most automated image processing systems, as well as calibration routines for three major system functions. The five areas of subsystem verification comprise processing quality, illumination quality, image collection quality, autofocus quality, and position quality.

Processing quality

Electronic systems and processors found in automated image processing systems are among the most reliable components in these systems. However, a failure in these areas can have ill effects. Therefore, the power supplies and the image processing computers are automatically checked by a computer processor to provide assurance of processing quality integrity during processing.

Illumination quality

The illumination system is potentially the most volatile component of an automated image processing system. This is true because arc lamps, which are characterized by high nonuniformity and spatial variation, are often used. Also changes in ambient conditions, including temperature and vibration, may affect uniformity. The goal of testing this system is to ensure the field of view is consistently and uniformly illuminated at the proper intensity over a defined range of conditions. These conditions include variations in the thickness of the slide upon which the specimen is mounted.

Image collection quality

The collection system is one of the most complex of the five subsystems. This is because it requires a higher degree of mechanical, optical and electrical complexity to perform its function. The objective of testing this system is to ensure that the images provided to the processing system are collected with the desired linearity, frequency response and signal-to-noise ratio.

Autofocus quality

The autofocus system provides the closed loop control that ensures the images received by the image collection system have a focus of clinical value. The goal is to ensure proper balance of frequency response, spatial position and signal-to-noise ratio at the focus cameras. Generally, this balance dictates the clinical value of the focus.

Position quality

The positioning system must ensure that the proper fields are appropriately positioned in the illumination, image collection and autofocus systems. Repeatability failures in the turret and the X,Y stage contribute to positioning errors that may cause a critical portion of the field to be missed by the instrument. This suite of tests ensures that the likelihood of a missed object is minimized.

CALIBRATIONS

In one embodiment, the areas of calibration include 4×illumination and pixel calibration, 20×illumination and pixel calibration, and parfocal and centration calibration. The camera illumination must be set up at each magnification to optimize use of the camera's dynamic range. The sensitivity variation of camera pixels, the variation of camera dark current, and variations in the illumination intensity require the final pixel offset and sensitivity adjustments. The 20×magnification uses the same calibration rationale as the 4×magnification. However, the 20×calibration also includes some adjustments to the autofocus system. These adjustments involve subtracting the noise floor from the focus cameras. In this calibration, a white field image is presented to the focus cameras. In this case, since there is no image to focus on, the focus score produced should be "0". However, some residual score is usually present due to sensitivities in the system, such as dust, temperature etc. This score is referred to as the noise floor and is subtracted from the signal for processing during runtime. The mechanics within the system are subject to many tolerances and thermal variations. Fortunately, these variations can be compensated for by measuring deviations from expected values. By measuring these deviations, correction factors, or offsets, can be computed and applied to compensate for the variations.

It is one motivation of the invention to provide a method for identifying potential device efficacy problems, thereby providing a means to substantially reduce erroneous results that could lead to misdiagnosis.

It is another motivation of the invention to provide a method and apparatus for data collection to determine the relationship between system parameters and feature calculations for highly statistical image processing applications. This provides a means for rapid advancement for this class of image processing applications.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 31 is an illustrative diagram of a circuit for determining the focus position of the camera assembly of FIG. 30 in accordance with an alternate focussing procedure.

FIG. 32 shows a schematic view of a typical cell.

FIG. 33 shows a process for converting physical cell size into electrical band width.

DETAILED DESCRIPTION OF THE PREFERRED EMBODIMENT

In a presently preferred embodiment of the invention, the camera system disclosed herein is used in a system for analyzing cervical pap smears, such as that shown and disclosed in U.S. Pat. No. 5,787,188, issued Jul. 28, 1998 to Nelson et al., entitled "METHOD FOR IDENTIFYING NORMAL BIOMEDICAL SPECIMENS" which is a file wrapper continuation of abandoned U.S. patent application Ser. No. 07/838,064, filed Feb. 18, 1992; U.S. Pat. No. 5,528,703, issued Jun. 18, 1996 to Lee entitled "METHOD FOR IDENTIFYING OBJECTS USING DATA PROCESSING TECHNIQUES", which is a file wrapper continuation of abandoned U.S. patent application Ser. No. 07/838,395, filed Feb. 18, 1992; U.S. Pat. No. 5,315,700, issued May. 24, 1994 to Johnston et al., entitled "METHOD AND APPARATUS FOR RAPIDLY PROCESSING DATA SEQUENCES"; U.S. Pat. No. 5,361,140, issued Nov. 1, 1994 to Hayenga et al., entitled "METHOD AND APPARATUS FOR DYNAMIC CORRECTION OF MICROSCOPIC IMAGE SIGNALS"; and allowed U.S. patent application Ser. No. 08/302,355, for which the issue fee has been paid, filed Sep. 7, 1994 entitled "METHOD AND APPARATUS FOR RAPID CAPTURE OF FOCUSED MICROSCOPIC IMAGES" to Hayenga et al., which is a continuation-in-part of abandoned U.S. patent application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention, filed on Sep. 20, 1994 unless otherwise noted, and which are all hereby incorporated by reference including U.S. Pat. No. 5,715,326, issued Feb. 3, 1998 to Ortyn et al., entitled "CYTOLOGICAL SYSTEM ILLUMINATION INTEGRITY CHECKING APPARATUS AND METHOD"; U.S. Pat. No. 5,581,631, issued Dec. 3, 1996 to Ortyn et al., entitled "CYTOLOGICAL SYSTEM IMAGE COLLECTION INTEGRITY CHECKING APPARATUS", assigned to the same assignee as this application; U.S. Pat. No. 5,557,097, issued Sep. 17, 1996 to Ortyn et al., entitled "CYTOLOGICAL SYSTEM AUTOFOCUS INTEGRITY CHECKING APPARATUS"; U.S. Pat. No. 5,499,097, issued Mar. 12, 1996 to Ortyn et al., entitled "METHOD AND APPARATUS FOR CHECKING AUTOMATED OPTICAL SYSTEM PERFORMANCE REPEATABILITY".

Figure 1A:
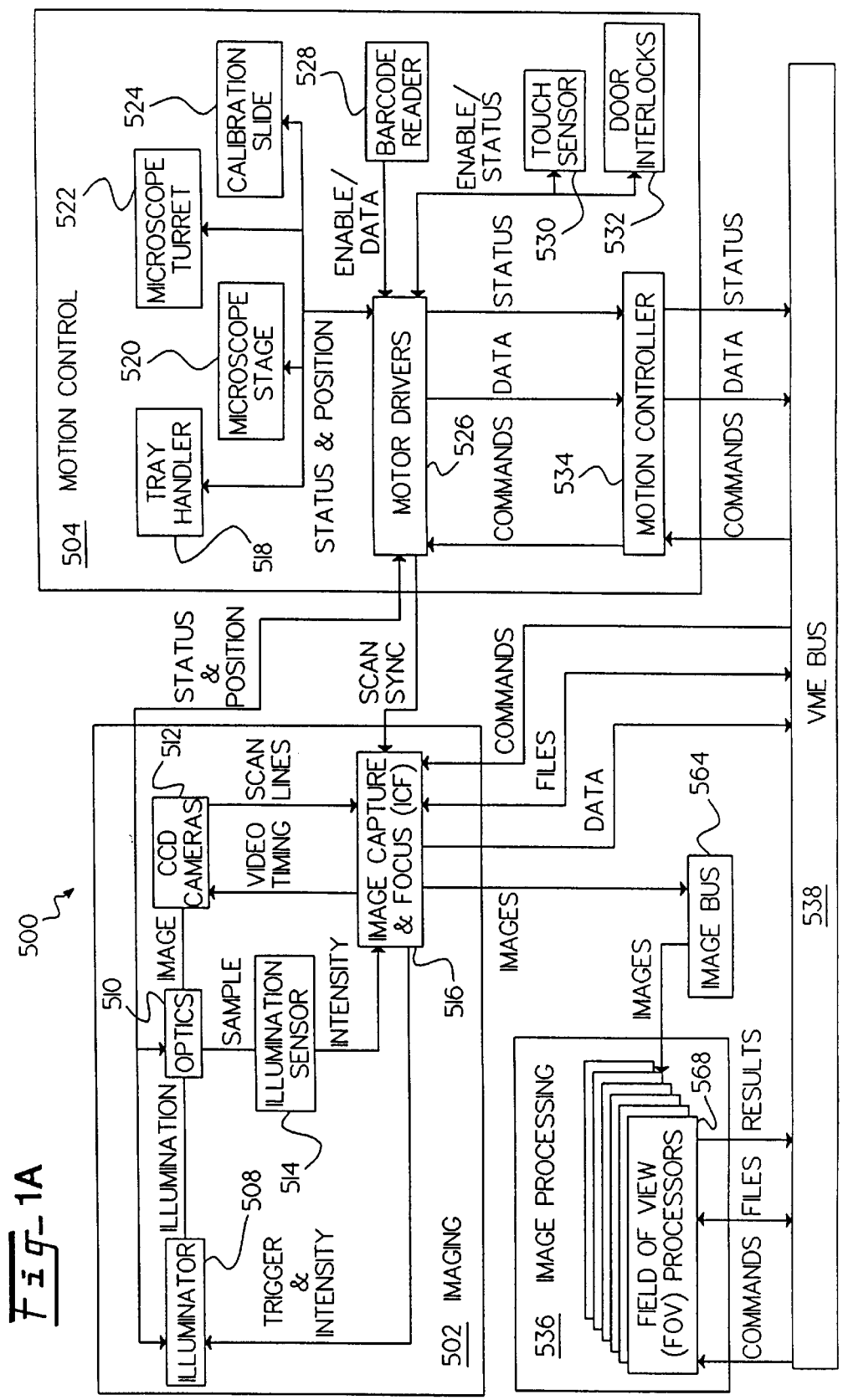
FIGS. 1A, 1B, 1C and 1D show an automated cytology system and the placement of a calibration and test target into an optical path of an automated microscope as employed by the method and apparatus of the invention.

Now refer to FIGS. 1A and 1B which show a schematic diagram of one embodiment of the apparatus of the invention for checking system autofocus integrity for an automated scanning system. While the method and apparatus of the invention will be discussed in terms of an example herein related to an automated cytology apparatus, it will be understood that the invention is not so limited. The features and principles of the invention may be applied to check urine analysis processes, semiconductor process defects, liquid crystal devices and other types of processing systems employing, for example, continuous arc lamps, filament lamps, laser sources, tube cameras, PIN diodes and photomultiplier tubes.

The apparatus 500 of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In one embodiment of the invention, the optics may further comprise an automated microscope. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a Motorola 68030 CPU. The motion controller 504 is comprised of a tray handler 518, a microscope stage controller 520, a microscope turret controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet (TM) communication system 560 communicates to a workstation 542 to provide control of the system. A hard disk 544 is controlled by workstation processor 550. In one embodiment, workstation 542 may comprise a Sun SPARC Classic (TM) workstation. A tape drive 546 is connected to the workstation processor 550 as well as a modem 548, a monitor 552, a keyboard 554, and a mouse pointing device 556. A printer 558 is connected to the Ethernet (TM) network 560.

During system integrity checking, the central computer 540, running a real time operating system, controls the automated microscope and the processor to acquire and digitize images from the microscope. The flatness of the slide may be checked, for example, by contacting the four corners of the slide using a computer controlled touch sensor. The computer 540 also controls the microscope stage to position the specimen under the microscope objective, and from one to 15 field of view (FOV) processors 568 which receive images under control of the computer 540.

It is to be understood that the various processes described hereinabove with respect to checking illumination quality, noise floor level, focus filter frequency response, focus camera frequency response, focus camera longitudinal separation, focus camera lateral and angular alignment, and closed loop accuracy in an instrument performing automated biological specimen analysis may be implemented in software suitable for running on a digital processor or computer. The software may be embedded, for example, in the central processor 540.

Figure 1C:
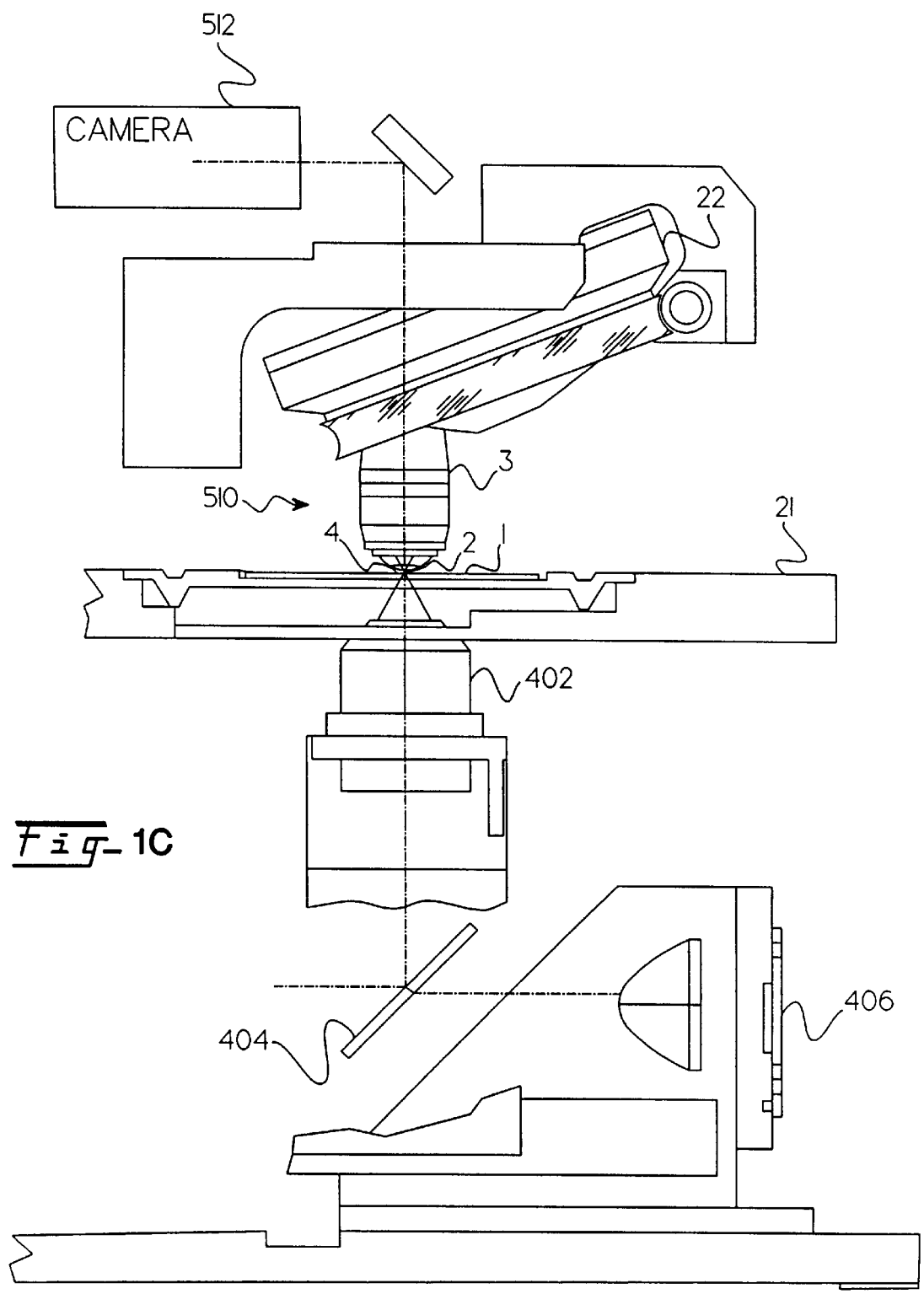

Referring now to FIG. 1C, there shown is placement of a calibration and test target 1 into an optical path of an automated microscope 3 having a turret 22. The calibration and test target may be mounted on a stage 21 substantially in a horizontal X,Y plane which intersects the optical path. The stage 21 is movable in the X,Y plane as well as along a Z axis which is perpendicular to the X,Y plane and which is parallel to the optical axis of the automated microscope. The turret 22 may comprise multiple objective lenses as is well known in the art. The microscope turret control 522 provides signals in a well known manner for positioning a selected objective lens into position for viewing a slide, for example.

Figure 1D:
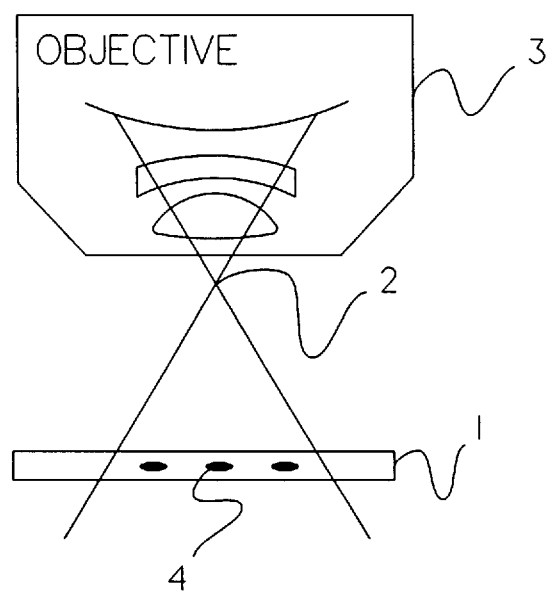

Referring now to FIGS. 1C and 1D, there shown is placement of a calibration and test target 1 into an optical path of an automated microscope 3. Several of the processes employed by the present invention require such a calibration and target plate. In the case of a transmission microscope, the calibration and test target 1 may be a clear piece of glass that is approximately 1.45 mm thick. The calibration and test target advantageously comprises specified clear areas and image primitives such as horizontal and vertical bar targets. Such calibration and test target plates are used for most transmission microscopes to simulate the optical path difference effects introduced by the substrate, coverslip and specimen media. The calibration and test target 1 is positioned longitudinally away from a plane of best focus 2 to reduce the effects of flaws in the glass and contaminants 4 that may stick to the surface of the calibration and test target plate.

Figure 1E:
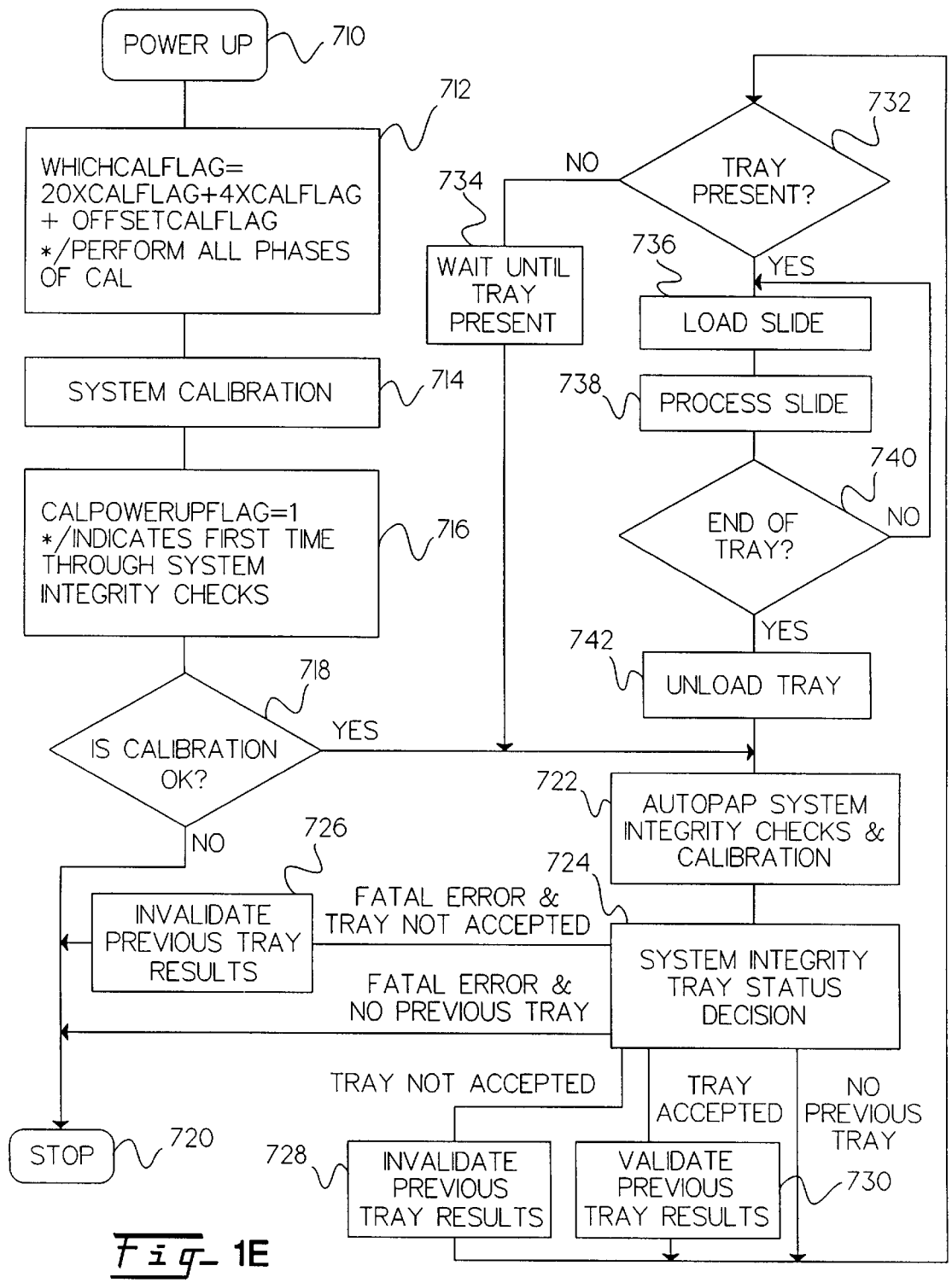
FIG. 1E shows a process flow diagram for an automated method for checking system integrity in an automated cytology system.

Now referring to FIG. 1E which shows a process flow diagram for an automated method for checking system integrity in an automated cytology system. When the system is powered up in step 710, all phases of calibration are performed, including setting WhichCalFlag=20×CalFlag+4×CalFlag+OffsetCalFlag in step 712. A System Calibration is performed in step 714. After calibration is completed, CalPowerUpFlag is set to 1 to indicate the first run through of the system integrity checks in step 716. The system then checks in step 718 if the system calibration is successful. If the calibration is unsuccessful, the system fails and stops in step 720. If the system calibration was successful in step 718, then the process flows to step 722, which initiates the system integrity checks and calibration.

Figure 1H:
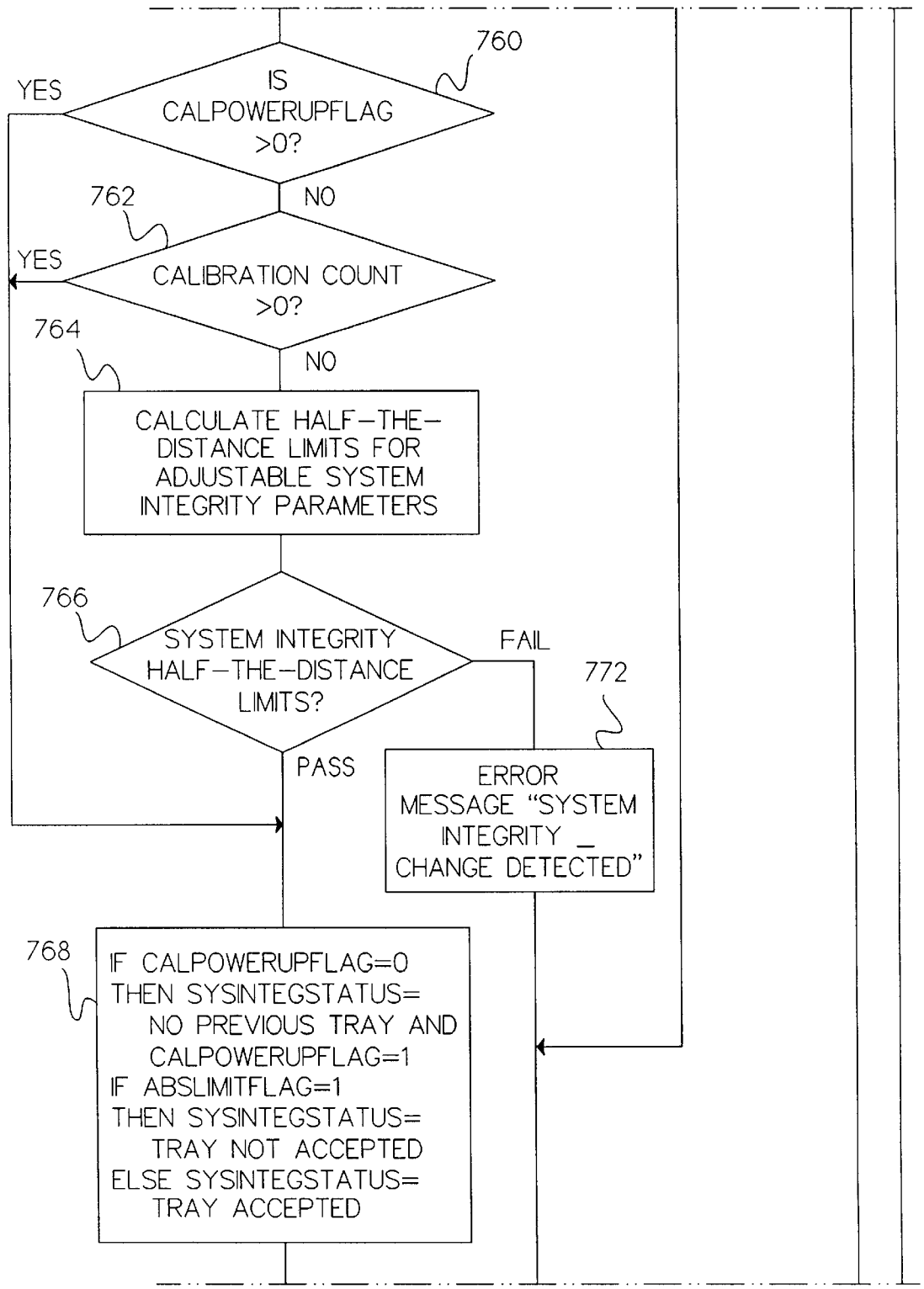
FIG. 1F comprises FIGS. 1G, 1H and 1I which are intended to be pieced together to show a more detailed process flow diagram for an automated method for running system integrity checks in an automated cytology system.

The system integrity checks and calibration are further illustrated in FIG. 1F which comprises FIG. 1G, FIG. 1H and FIG. 1I. After the system integrity checks have been performed, the system determines the status of the integrity of a current tray, where each tray contains slides having biological specimens. If the system failed the integrity checks and calibration in step 722, and there is no previous tray, then the system reports a fatal error and stops 720. If the system failed the integrity checks and a previous tray exists, then the system reports a fatal error and invalidates the previous tray results in step 726 and stops 720. If the system does not have a fatal error, then there are three outcomes. First, if there was no previous tray, the system proceeds to step 732 to check if a next tray is present. Second, if the tray is accepted, then the previous tray results are validated and the system proceeds to step 732 to check if a next tray is present. Finally, if the tray is not accepted, the previous tray results are invalidated and the system proceeds to step 732 to check if a next tray is present.

If a tray is not present, the process flows to step 734, requiring the system to wait until a next tray is present, then flowing to step 722 to perform the system integrity checks and calibration. If a tray is present in step 732, then the system loads a slide from the tray in step 736 and processes the slide in step 738. After the slide is processed, the system checks to see if the end of the tray has been reached. If there are more slides, the process flows back to step 736 until all the slides have been loaded and processed. Once the end of the tray has been reached, the system unloads the tray in step 742, and proceeds to step 722 to perform the system integrity checks and calibration.

Now referring to FIGS. 1G–1I which show a detailed process flow for step 722, performing system integrity checks and calibration. The process begins in step 750, and sets the calibration count=0 and the AbsLimitFlag=0. The system integrity tests are performed in step 754. The system then saves the system integrity data and a time stamp in a temporary data space in step 756. In step 758 the system performs a check to compare the system integrity to absolute limits. If the system passes the check, the process flows to step 760, where the system checks if CalPowerUpFlag >0. If CalPowerUpFlag is >0 the system passes the integrity checks and the process flows to step 768. If CalPowerUpFlag is not >0, then the process flows to step 762 to check if the calibration count >0. If the calibration count is >0, then the system passes the integrity checks and the process flows to step 768. if the calibration count is not >0, then the process flows to step 764 to calculate half-the-distance limits for adjustable system integrity parameters. In step 766, the adjustable system integrity parameters are check to see if they are within the half-the-distance limits. If they are the system passes and the process flows to step 768. If the adjustable system integrity parameters are not within the half-the-distance limits, then the system fails and displays an error message indicating that "system integrity change_ detected" in step 772. Wherein the computer system fills in the message.

In step 768, if CalPowerUpFlag=0, then SysIntegStatus is set to No Previous Tray and CalPowerUpFlag=1. If AbsLimitFlag=1 then SysIntegStatus=Tray Not Accepted and otherwise SysIntegStatus=Tray Accepted. The process then flows to step 770 and the integrity tray status is returned to the system.

If the system fails the integrity data comparison to absolute limits in step 758, then the system fails and AbsLimitFlag is set to 1 in step 790. The system then displays the error message "_System Integrity Absolute Limit_failed." The process then flows to step 796 to check whether the CalibrationNecessary Flag is set. If the CalibrationNecessary Flag has been set, then the system performs a system calibration in step 774. In step 776, the system checks whether the calibration has passed. If the calibration passed, the calibration count is incremented in step 778. The calibration count is checked in step 780 to see if the CalCountLimit has been exceeded. If the calibration count has not exceeded, the process returns to step 754 to perform the system integrity checks. If the calibration count has exceeded, then the process flows to step 782. If the calibration did not pass in step 776, the process flows to step 788 to check if the calibration count has exceeded CalCountLimit. If CalCountLimit was not exceeded, then the system returns to step 774 to recalibrate. Otherwise the process flows to step 782.

In step 782 the CalPowerUpFlag is checked to see if it is set to 0. If so, the SysIntStatus is set to "FATAL ERROR+No Previous Tray" and otherwise SysIntStatus is set to "FATAL ERROR+Tray Not Accepted."

In step 758, if the system fails the comparison of system integrity data to absolute limits, then the system fails and the process flows to step 790, where AbsLimitFlag is set to 1. The error message "_System Integrity Absolute Limit_ failed" is displayed in step 794, and the system proceeds to step 796 to check whether the CalibrationNecessary Flag is set. If so, the system proceeds to step 774 to run the system calibration. Otherwise, the system fails and the process flows to step 782.

The process illustrated by FIG. 1E indicates that slide specimen data is taken only after system integrity and calibration tests have been performed and passed to ensure that the system is operating within its engineered limits. If a system integrity failure is detected, the slide diagnosis results are invalidated for the previous tray. The system integrity tests are repeated until all tests have passed or until the number of allowed iterations has been exceeded. Continued failure of the system integrity tests causes processing to stop. This process is illustrated by FIGS. 1G–1I.

System integrity failure can be caused by a failure to perform the tests or by one or more of the tests failing the checks. All test measurements are compared against absolute limits. In addition, a half-the-distance check is also applied to those measurements that are susceptible to drift. The half-the-distance check improves throughput by attempting to predict a failure and thus reduces the possibility of having to invalidate the results after a tray analysis is complete.

System integrity absolute (SI absolute) is a criteria to be applied to the parameter limits. These limits define the absolute amount of variation for each parameter. If a measured parameter is outside of the absolute limits, then a system integrity failure results. An SI absolute failure results in termination of machine operation. The SI absolute criteria is applied as shown in FIG. 1E.

System integrity half the distance (SIHTD) is another criteria to be applied to the parameter limits. The purpose of SIHTD is to detect parameter drift. When parameter drift is detected, recalibration can be performed before the system drifts out of specification. By applying this criteria, throughput is improved by reducing the possibility of invalidating tray results because of a system integrity failure being detected after completely analyzing a tray. This criteria determines if a parameter has drifted more than half the way between its last measured value and the limit. An SIHTD failure results in a calibration. The criteria is applied as follows:

Where v equals value recently measured the limit. An SIHTD failure results in a calibration.

The criteria is applied as follows:

Where v equals value recently measured v' equals previous value l equals limits as defined in Section 3

For maximum limits:

If: $v > v' + (l-v')/2$ Then:fail

If: $v <= v' + (l-v')/2$ Then:pass

For minimum limits:

If: $v < v' + (l-v')/2$ Then:fail

If: $v >= V' + (l-V')/2$ Then:pass

To provide information about system integrity for diagnostic or debugging purposes, the SI tests must display test information to standard output devices that would not otherwise be available. This test information includes state of operation, intermediate measurement values, stage position, and so on. A verbosity switch is implemented that allows test reporting to be enabled at different levels (minimum or full reporting) or disabled. However, individual test failures are always recorded in the system log file, regardless of how the verbosity switch is set.

The following is a list of the individual tests:

Processing Quality
    Image Transfer and Processing
    Power Supply Limits
Illumination Quality
    Global Illumination Variation
    Static Field Uniformity
    Dynamic Field Uniformity
    Slide Thickness Variation
    Cal Plate Dirt Check
    Strobe Variation
    Strobe Drop Out Monitor
Collection Quality
    System Linearity
    20×Frequency Response
    4×Frequency Response
    Collection Signal to Noise
    Pixel Correction Gain and Offset
Focus Quality
    Focus Illumination
    Focus Noise Floor
    Focus Filter Frequency Response
    Focus Camera Frequency Response
    Focus Camera Longitudinal Separation Focus Camera Lateral and Angular Offsets
Closed Loop Fiducial Focus Test
Position Quality
  X,Y Repeatability
  Turret Repeatability
  Cal plate Tilt
  4×, 20×, Surface Sense Parfocality and Centration
4×Illumination and Pixel Calibration
  4×Illumination Adjustment
  4×Pixel Offset and Gain Adjustment
  4×Illumination Adjustment
  4×Pixel Offset and Gain Adjustment
20×Focus, Illumination and Pixel Calibration
  20×Illumination Adjustment
  20×Pixel Offset and Gain Adjustment
  20×Focus Noise Table Adjustment
Mechanical Parfocal and Centration Calibration
  4×to 20×Parfocal and Centration Adjustments
  20×to Surface Sense Adjustment The method of the invention for checking global illumination ensures the field of view is illuminated at the proper intensity and that the global intensity does not vary by more than the limits shown.

Figure 2:
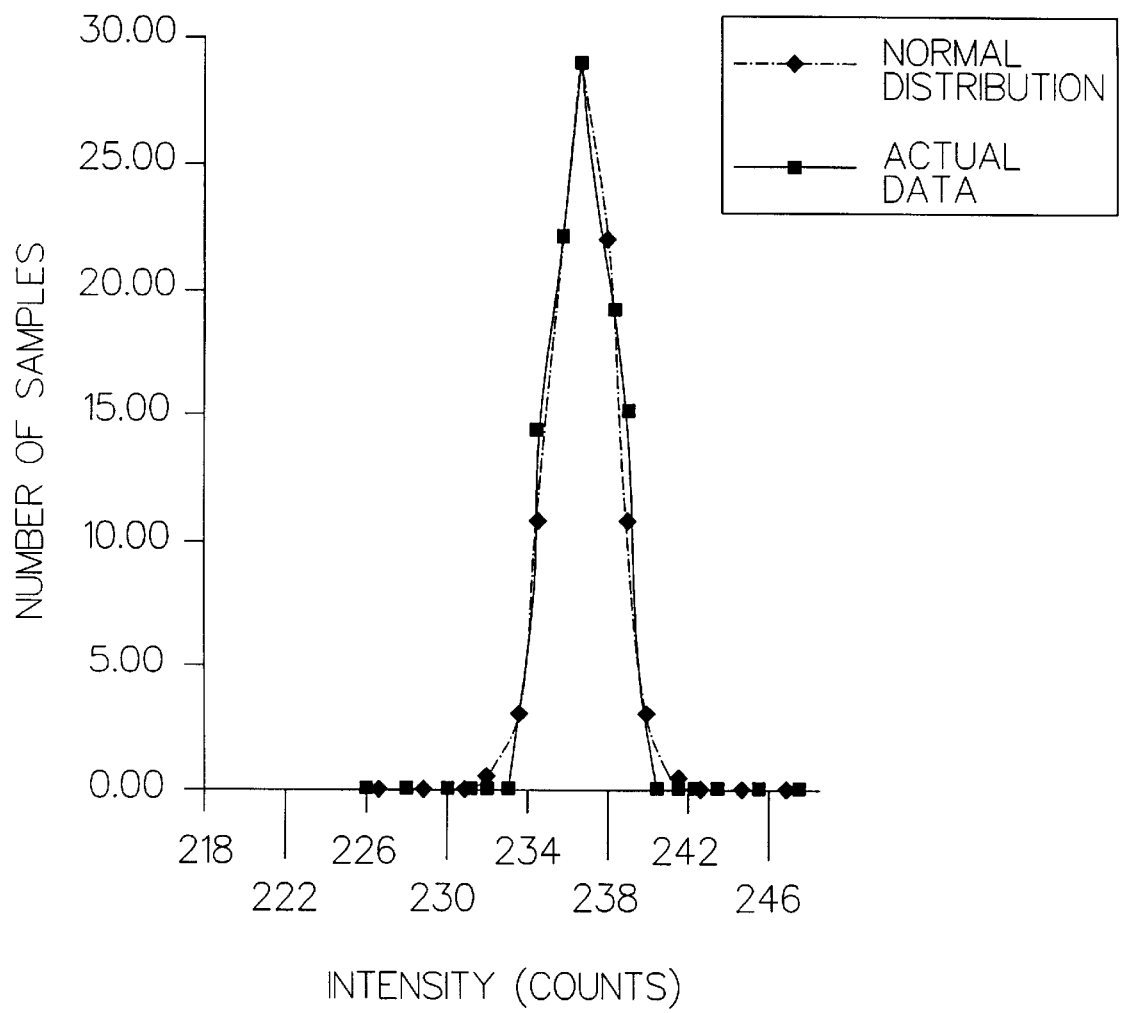
FIG. 2 shows a histogram of global illumination variation.
Figure 6:
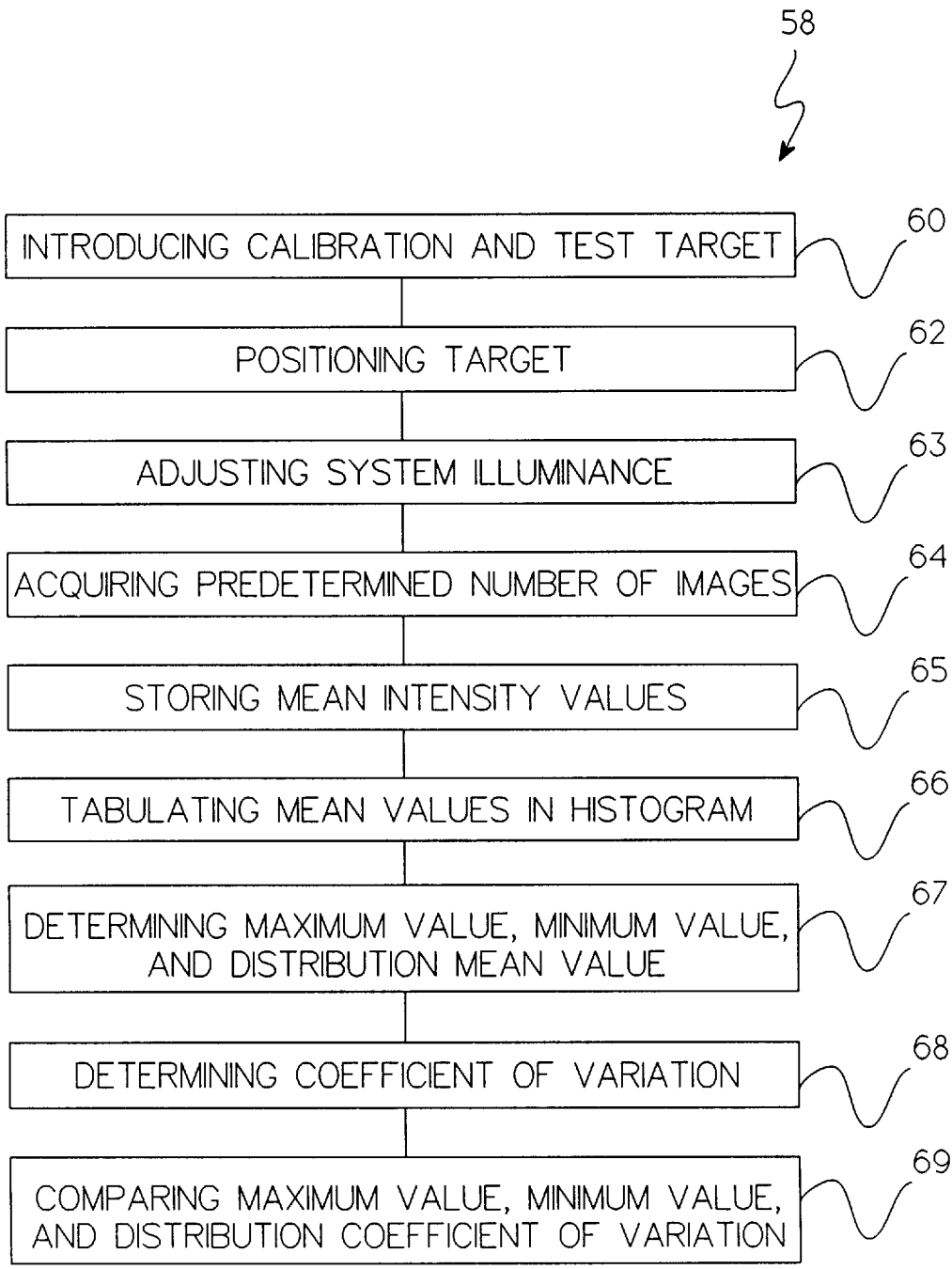
FIG. 6 shows a flow diagram of one example of a global illumination test as provided by the method of the invention.

FIG. 2 shows a plot of the data in Table 1. It is apparent from FIG. 2 that the variation behaves like a normal random distribution. As shown in FIG. 6, the maximum, minimum, mean and coefficient of variation for the distribution are determined at process step 67. These parameters are compared, in step 69 against engineered limits as shown in Table 2. A coefficient of variation of these mean values is determined at process step 69. Camera dynamic range is defined herein as the mean of mean voltages measured at the CCD for all images. Examples of engineering limits used in one example of the invention for checking global illumination variation are as follows.

Camera dynamic range: 0.665 V<x<0.690 V
  Coefficient of variation: <1.0%
  Maximum % Variation: (max-min)/(2*mean)<1.5%
  Mean: 223 counts<∞<242 counts

TABLE 1

| Intensity | Normal Distribution | Actual Data |
| --- | --- | --- |
| 226 | 0.00 | 0 |
| 227 | 0.00 | 0 |
| 228 | 0.00 | 0 |
| 229 | 0.00 | 0 |
| 230 | 0.00 | 0 |
| 231 | 0.06 | 0 |
| 232 | 0.53 | 0 |
| 233 | 3.06 | 0 |
| 234 | 10.67 | 14 |
| 235 | 22.59 | 23 |
| 236 | 29.00 | 29 |
| 237 | 22.59 | 19 |
| 238 | 10.67 | 15 |
| 239 | 3.06 | 0 |
| 240 | 0.53 | 0 |
| 241 | 0.06 | 0 |
| 242 | 0.00 | 0 |
| 243 | 0.00 | 0 |
| 244 | 0.00 | 0 |
| 245 | 0.00 | 0 |
| 246 | 0.00 | 0 |

TABLE 2

Parameter Results and Limits Comparison

| Parameter Description | Actual Value | Limits |
| --- | --- | --- |
| Mean Intensity | 236 | 223 counts < ∞ < 242 counts |
| Coefficient of Variation | 0.53% | <1.0% |
| Maximum % variation | 0.85% | (max-min)/(2*mean) < 1.5% |

Figure 3:
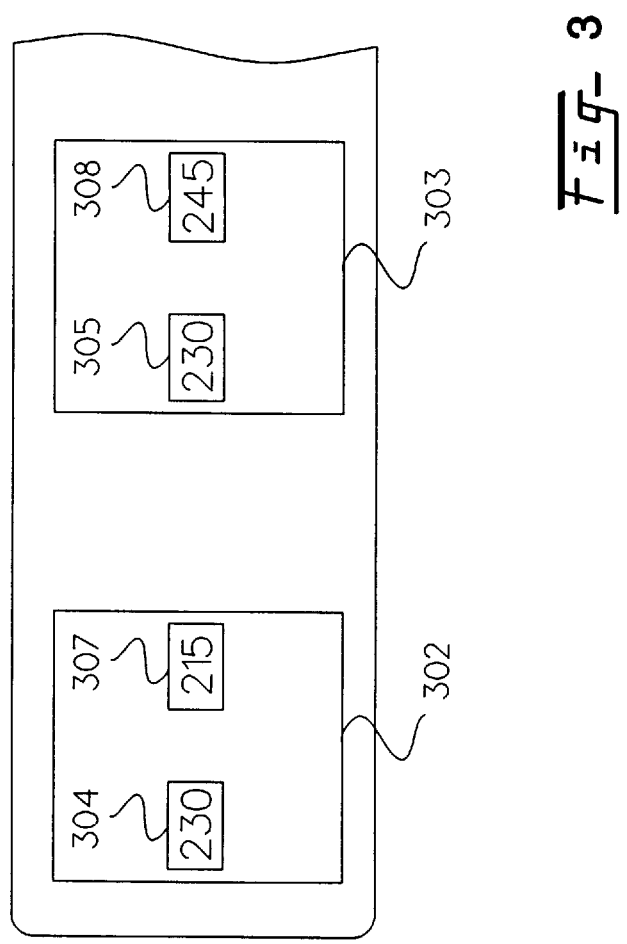
FIG. 3 shows an illustration of two illuminated fields as may be evaluated by a dynamic field uniformity test employed by the method of the invention.

FIG. 3 shows an illustration of two illuminated fields as may be evaluated by a dynamic field uniformity test employed by the method of the invention. In each of the two fields 302, 303 the pixel on the left 304, 305 respectively, maintained a value of 230. However, the intensity of the pixel on the right 307, 308 respectively differs by 30 counts between the fields. This represents a change in intensity of ±6.5%. The dynamic field uniformity test is run to check for such a condition.

Strobe Repeatability

Figure 4:
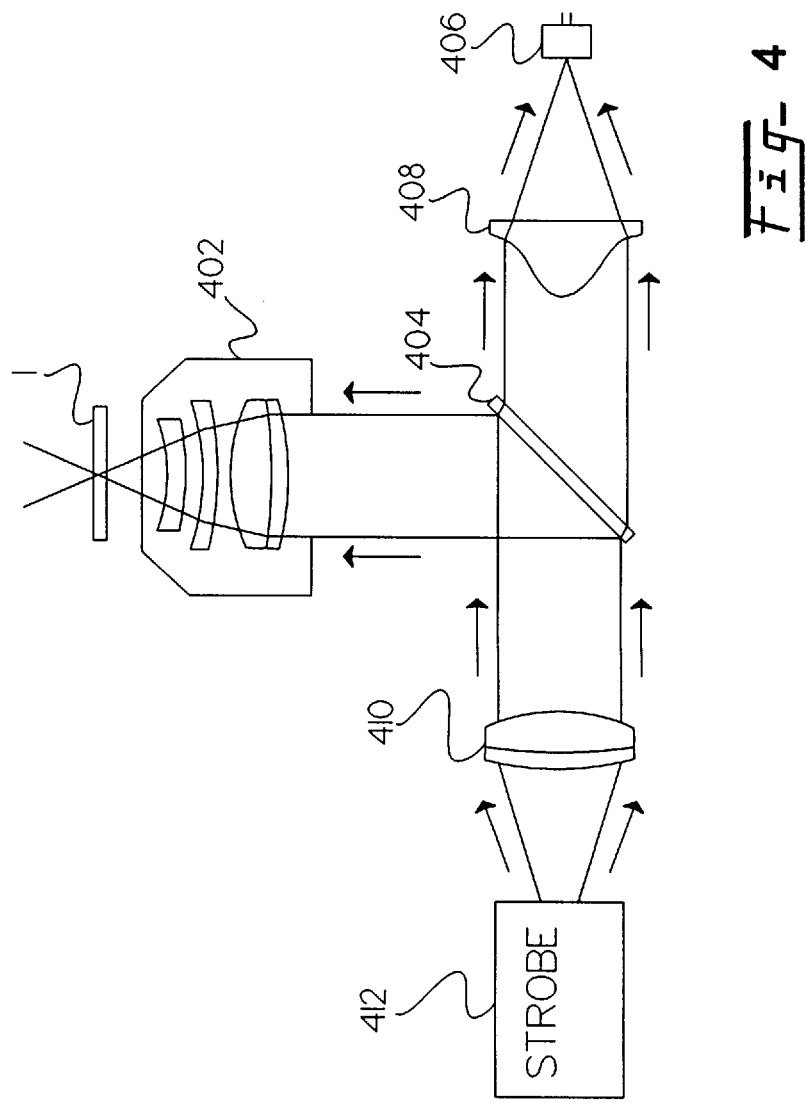
FIG. 4 shows an evaluation apparatus used in a strobe repeatability test method of the invention.

Referring now to FIG. 4, FIG. 4 shows an evaluation apparatus used in a strobe repeatability test method of the invention. In one example embodiment of the invention a pulsed arc lamp, or strobe 412, for illumination is employed. The strobe transmits light through optics 410. A beam splitter 404 is positioned to receive the light to split the light into a first beam and a second beam wherein the second beam provides illumination to condenser lens 402 for a microscopic evaluation of the slide 1. A detector 406 is positioned in an optical path defined by the beam splitter 404 and a second lens 408 to receive the first beam for providing a detected signal indicative of a first beam intensity. The automated microscope may use the detected signal to adjust for illumination variations. Alternately, a running average of detected signals is obtained. This average may be used to detect and correct for any long term drift of the strobe output intensity. Aging of the strobe and drive electronics can cause a strobe to become unstable and vary the energy output from flash to flash. This variation is not unlike variations that may occur in other illumination sources. The preferred embodiment shown comprises a double beam system where detector 406 comprises a PIN diode positioned to receive light from the strobe as light is split away from the main optical path of light directed toward the specimen. As shown, a beam splitter 404 is placed to split the light before it reaches the specimen.

Figure 5:
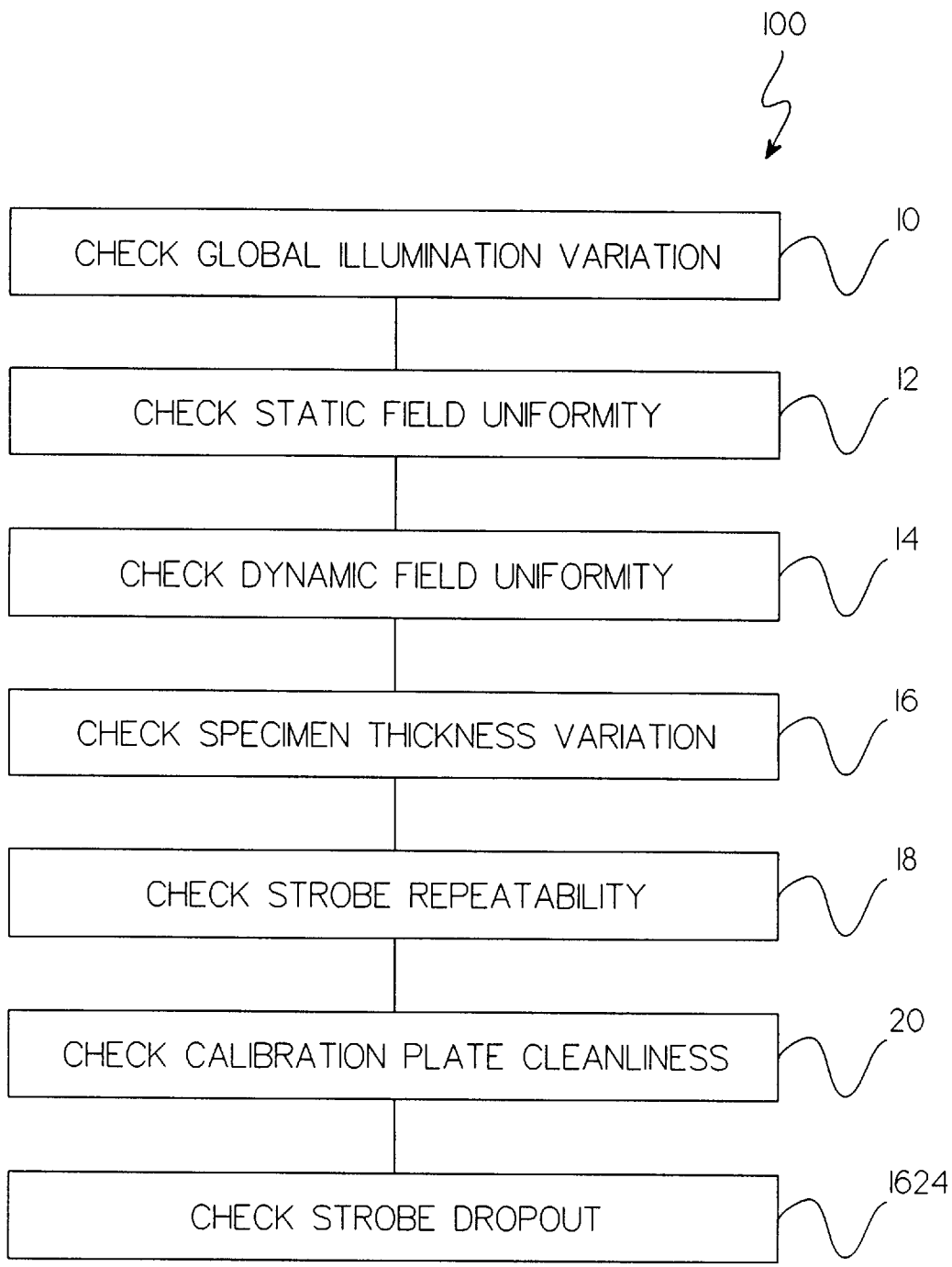
FIG. 5 shows a high level flow diagram of one example of the method of the invention to check biological specimen system illumination integrity.

Referring now to FIG. 5, a flow diagram of one example of the method of the invention for biological specimen system illumination integrity checking is shown. The order of checking process steps shown in FIG. 5 is by way of illustration only and is not intended to so limit the invention. The biological specimen system illumination integrity checking method 100 includes checking global illumination variation at process step 10, checking static field uniformity at process step 12, checking dynamic field uniformity at process step 14, checking specimen thickness variation at process step 16, checking strobe repeatability at process step 18, checking calibration plate cleanliness at process step 20 and checking strobe dropout at process step 1624. Each of these process steps will be explained in more detail hereinbelow.

Global Illumination

Illumination sources typically employed in automated vision analysis instruments exhibit variations in energy output from one collected image to another collected image. In the case of pulsed arc lamps, the arc is unconstrained and can vary spatially between flashes. The combined effects of energy output variations and spatial variations may cause a variation of illuminance over the entire field of view from collected image to collected image. In addition, in order to approach optimal use of an imaging device, such as a CCD focal plane, the imaging device should be used as near as possible to its optimal dynamic range. That is to say, illuminance should be set at a level suitable for obtaining the optimal discrimination performance of the imaging device for the application.

Referring now to FIG. 6, a flow diagram of one method of the invention for providing global illumination variation tests 58 is shown. Global illumination tests are used to check the illuminance level of a light source, such as an arc lamp. A calibration and test target is introduced into the optical path at process step 60 and positioned at process step 62. At process step 63, the system illuminance is adjusted to an optimal level as may best be determined by an operator or automated system, for example. A predetermined number of images are acquired at process step 64. In one example of the invention, about one hundred (100) images are acquired. Each image may comprise a 512×512 array of pixels that are quantized into 256 grey levels. The mean pixel value for each acquired image is computed and temporarily stored at process step 65. These mean intensity values are tabulated at step 66 in a histogram format like that shown in Table 1. The left most column of Table 1 represents the mean intensity of the illuminated field in counts. The right most column denotes the number of occurrences of the corresponding mean field intensity for the one hundred images acquired. The center column represents a normally distributed variation with a mean and standard deviation similar to the actual data. It is only shown to demonstrate that the actual data varies in accordance with normally distributed population. Therefore, the data can be analyzed using standard statistical parameters.

Static Field Uniformity

Figure 7:
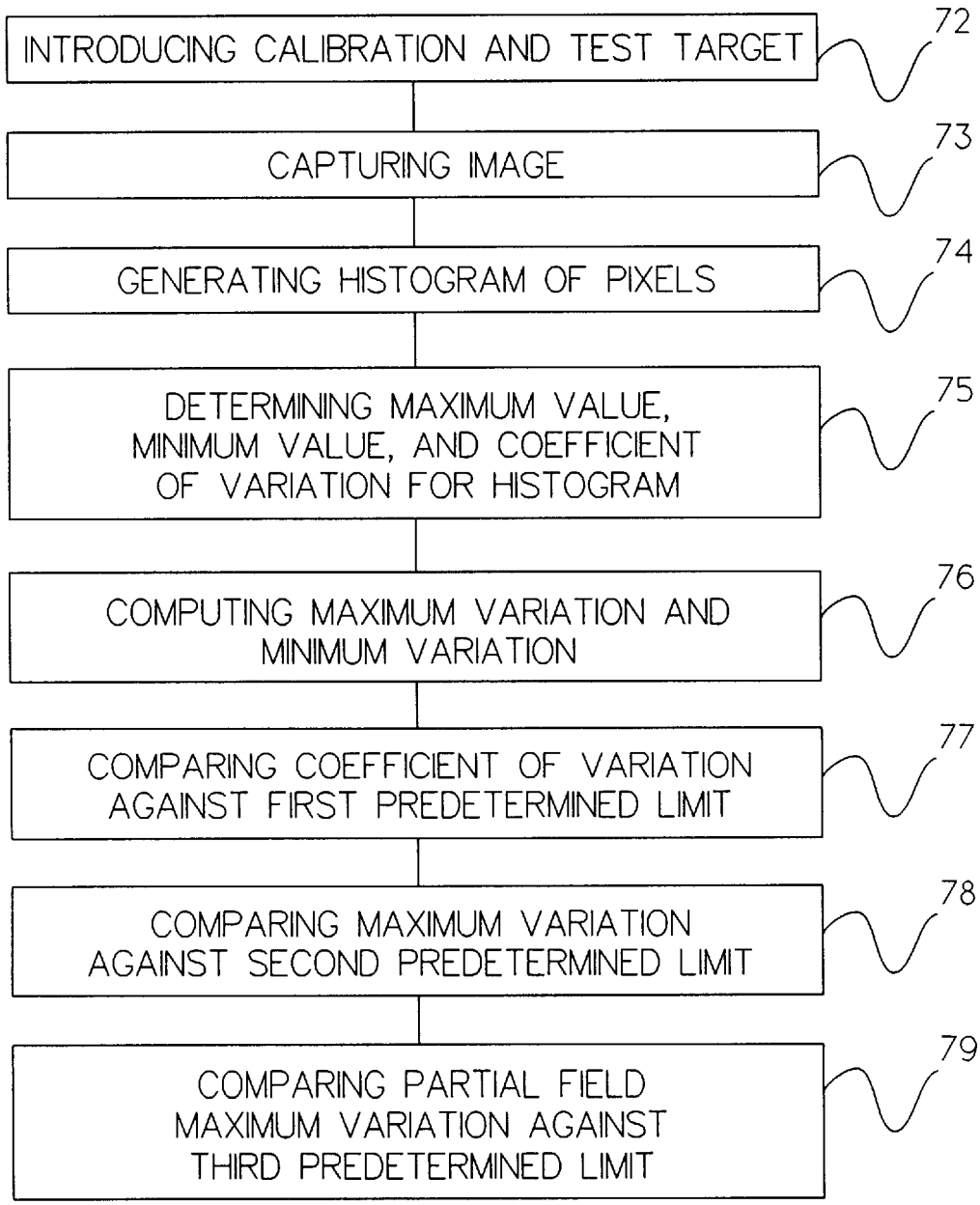
FIG. 7 shows a flow diagram of one example of a method for checking static field of uniformity as employed by the method of the invention.

Referring now to FIG. 7, a flow diagram illustrating the method of the invention for checking static field of uniformity as employed by the method of the invention is shown. The field of view illuminated in automated vision analysis instruments can vary in intensity at various points in the field due to misalignments, debris on optical surfaces, poor optical design in addition to other factors. In addition, the spatial response of the detector, such as a CCD camera, may also vary exhibiting a behavior known as patterning. The totality of these variations may be referred to as static field uniformity.

As before, a calibration and test target is introduced into the optical path at process step 72. A single image is captured and a histogram is generated for the image pixels at process steps 73 and 74 respectively. The maximum, minimum values and the coefficient of variation of the pixels are determined for the histogram at step 75. Additionally, at step 76, the maximum and minimum variation is computed for 99.9% of the field-of-view by ignoring the 0.1% outlying pixels at the tails of the histogram. This value provides a measure of the field uniformity without the affects of stray pixels. The variation factors are evaluated by comparing the coefficient of variation against a first predetermined limit 77, comparing the maximum variation against a second predetermined limit 78, comparing the partial field maximum variation against a third predetermined limit 79.

TABLE 3

Intensity Histogram of Entire Field
INT = INTENSITY, # = NUMBER OF PIXELS AT CORRESPONDING INTENSITY

| Int | # | Int | # | Int | # | Int | # | Int | # | Int | # | Int | # | Int | # |
|---|---|---|---|---|---|---|---|---|---|---|---|---|---|---|---|
| 0: | 0 | 32: | 0 | 64: | 0 | 96: | 0 | 128: | 0 | 160: | 0 | 192: | 0 | 224: | 2 |
| 1: | 0 | 33: | 0 | 65: | 0 | 97: | 0 | 129: | 0 | 161: | 0 | 193: | 0 | 225: | 7 |
| 2: | 0 | 34: | 0 | 66: | 0 | 98: | 0 | 130: | 0 | 162: | 0 | 194: | 0 | 226: | 213 |
| 3: | 0 | 35: | 0 | 67: | 0 | 99: | 0 | 131: | 0 | 163: | 0 | 195: | 0 | 227: | 1424 |
| 4: | 0 | 36: | 0 | 68: | 0 | 100: | 0 | 132: | 0 | 164: | 0 | 196: | 0 | 228: | 7803 |
| 5: | 0 | 37: | 0 | 69: | 0 | 101: | 0 | 133: | 0 | 165: | 0 | 197: | 0 | 229: | 47942 |
| 6: | 0 | 38: | 0 | 70: | 0 | 102: | 0 | 134: | 0 | 166: | 0 | 198: | 0 | 230: | 60366 |
| 7: | 0 | 39: | 0 | 71: | 0 | 103: | 0 | 135: | 0 | 167: | 0 | 199: | 0 | 231: | 74350 |
| 8: | 0 | 40: | 0 | 72: | 0 | 104: | 0 | 136: | 0 | 168: | 0 | 200: | 0 | 232: | 51837 |
| 9: | 0 | 41: | 0 | 73: | 0 | 105: | 0 | 137: | 0 | 169: | 0 | 201: | 0 | 233: | 15630 |
| 10: | 0 | 42: | 0 | 74: | 0 | 106: | 0 | 138: | 0 | 170: | 0 | 202: | 0 | 234: | 2231 |
| 11: | 0 | 43: | 0 | 75: | 0 | 107: | 0 | 139: | 0 | 171: | 0 | 203: | 0 | 235: | 317 |
| 12: | 0 | 44: | 0 | 76: | 0 | 108: | 0 | 140: | 0 | 172: | 0 | 204: | 0 | 236: | 22 |
| 13: | 0 | 45: | 0 | 77: | 0 | 109: | 0 | 141: | 0 | 173: | 0 | 205: | 0 | 237: | 0 |
| 14: | 0 | 46: | 0 | 78: | 0 | 110: | 0 | 142: | 0 | 174: | 0 | 206: | 0 | 238: | 0 |
| 15: | 0 | 47: | 0 | 79: | 0 | 111: | 0 | 143: | 0 | 175: | 0 | 207: | 0 | 239: | 0 |
| 16: | 0 | 48: | 0 | 80: | 0 | 112: | 0 | 144: | 0 | 176: | 0 | 208: | 0 | 240: | 0 |
| 17: | 0 | 49: | 0 | 81: | 0 | 113: | 0 | 145: | 0 | 177: | 0 | 209: | 0 | 241: | 0 |
| 18: | 0 | 50: | 0 | 82: | 0 | 114: | 0 | 146: | 0 | 178: | 0 | 210: | 0 | 242: | 0 |
| 19: | 0 | 51: | 0 | 83: | 0 | 115: | 0 | 147: | 0 | 179: | 0 | 211: | 0 | 243: | 0 |
| 20: | 0 | 52: | 0 | 84: | 0 | 116: | 0 | 148: | 0 | 180: | 0 | 212: | 0 | 244: | 0 |
| 21: | 0 | 53: | 0 | 85: | 0 | 117: | 0 | 149: | 0 | 181: | 0 | 213: | 0 | 245: | 0 |
| 22: | 0 | 54: | 0 | 86: | 0 | 118: | 0 | 150: | 0 | 182: | 0 | 214: | 0 | 246: | 0 |
| 23: | 0 | 55: | 0 | 87: | 0 | 119: | 0 | 151: | 0 | 183: | 0 | 215: | 0 | 247: | 0 |
| 24: | 0 | 56: | 0 | 88: | 0 | 120: | 0 | 152: | 0 | 184: | 0 | 216: | 0 | 248: | 0 |
| 25: | 0 | 57: | 0 | 89: | 0 | 121: | 0 | 153: | 0 | 185: | 0 | 217: | 0 | 249: | 0 |
| 26: | 0 | 58: | 0 | 90: | 0 | 122: | 0 | 154: | 0 | 186: | 0 | 218: | 0 | 250: | 0 |
| 27: | 0 | 59: | 0 | 91: | 0 | 123: | 0 | 155: | 0 | 187: | 0 | 219: | 0 | 251: | 0 |
| 28: | 0 | 60: | 0 | 92: | 0 | 124: | 0 | 156: | 0 | 188: | 0 | 220: | 0 | 252: | 0 |
| 29: | 0 | 61: | 0 | 93: | 0 | 125: | 0 | 157: | 0 | 189: | 0 | 221: | 0 | 253: | 0 |
| 30: | 0 | 62: | 0 | 94: | 0 | 126: | 0 | 158: | 0 | 190: | 0 | 222: | 0 | 254: | 0 |
| 31: | 0 | 63: | 0 | 95: | 0 | 127: | 0 | 159: | 0 | 191: | 0 | 223: | 0 | 255: | 0 |

In this embodiment the values are evaluated against the following limits.

TABLE 4

| Parameter Description | Actual Value | Limits |
|---|---|---|
| Coefficient of variation: | 0.6% | <1.0% |
| Maximum % variation (full field) : | 2.6% | <6.0% |
| Maximum % Variation (partial field): | 1.7% | <3.0% |

Dynamic Field Uniformity

In addition to static non-uniformity, the illumination may vary dynamically from image to image. For example, on a given strobe flash, the field may have a maximum static variation of 15 units. On a subsequent flash, the static uniformity may be also be 15 units. However, that 15 units may be evident in the opposite direction giving an actual non-uniformity of 30 units.

Figure 12:
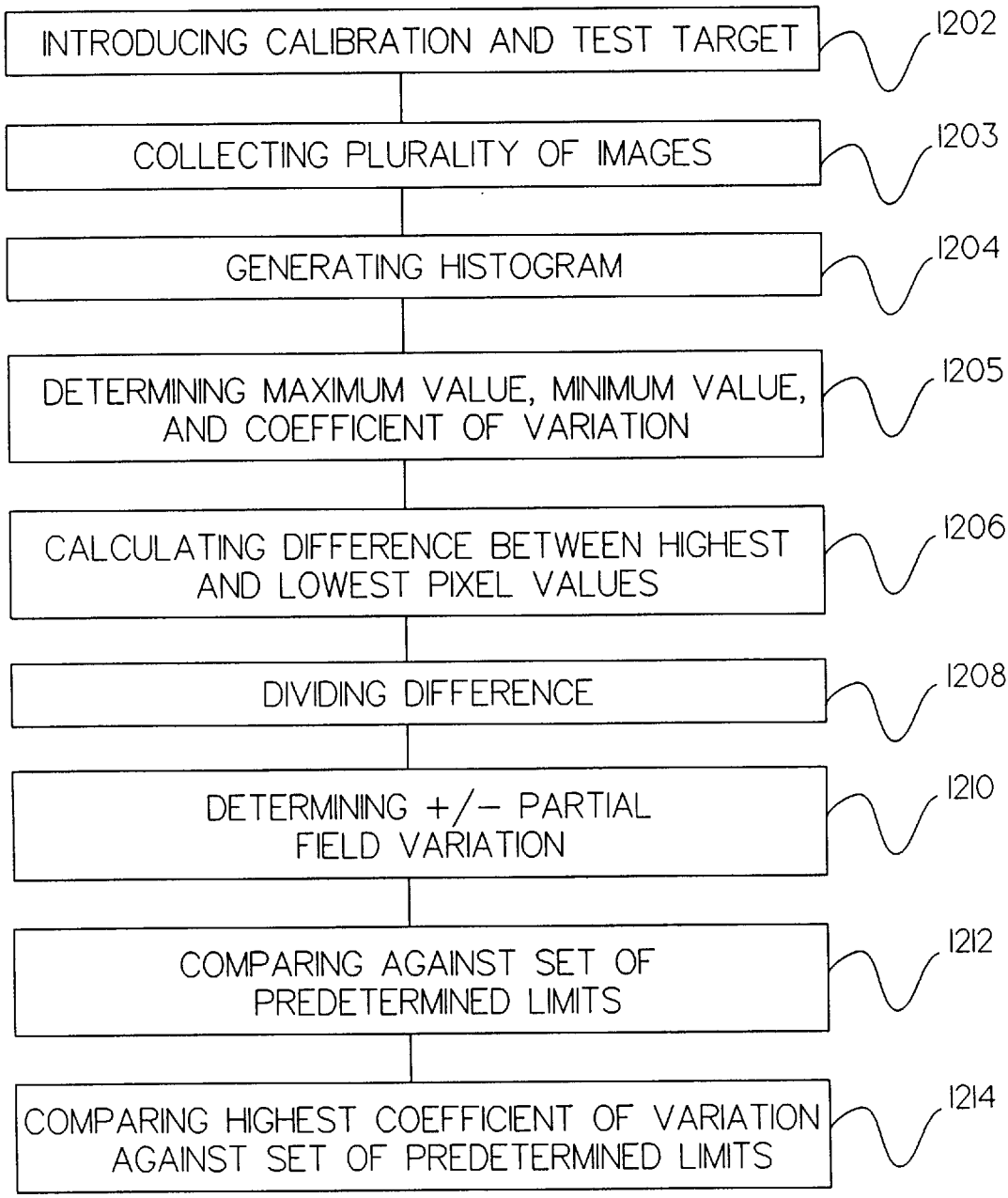
FIG. 12 shows a flow diagram of one method of the invention for checking dynamic field uniformity.

FIG. 12 shows a flow diagram of one method of the invention for checking dynamic field uniformity. As before, a calibration and test target is introduced into the optical path 1202. Fifty images are collected 1203 and a histogram is generated for each image 1204. The maximum, minimum values and the coefficient of variation are determined for each illuminated field 1205. Additionally, the maximum and minimum variation is computed for 99.9% of the field-of-view by ignoring the 0.1% outlying pixels at the tails of the histogram. A difference is taken between the highest and lowest pixel values for all 50 images 1206. This value is divided 1208 by two times the mean to determine the ± full field variations. The same method is used to determine the ± partial field variation 1210. These values are compared against limits 1212 as shown in Table 5. Likewise, the worst, that is the highest, coefficient of variation of the fifty fields is compared 1214 against the limit shown in Table 5. Table 5 also shows values from an actual test.

TABLE 5

Parameter Results and Limits Comparison for Dynamic Field Uniformity

| Parameter Description | Actual Value | Limits |
|---|---|---|
| Coefficient of variation | 0.6% | <1.0% |
| Maximum % variation (full field) : | 2.8% | <8.0% |
| Maximum % variation (partial field): | 1.9% | <4.0% |

Specimen Thickness Variation

The illumination system of FIG. 1C, for example, is designed to operate with prescribed optical path distances. However, in transmitted light microscopy, specimens are usually mounted on a substrate and a coverslip is placed over the substrate. The thickness of the substrate or slide, coverslip and mounting media may vary. These variations introduce a change in the optical path of the illumination system. These changes, if not carefully designed for, may degrade the illumination uniformity. In addition, uniformity may degrade at the upper of lower end of the slide thickness range due to the same reasons as mentioned in the static field uniformity section. Although this degradation may occur at one or the other or both extremes, it may not occur at the nominal slide thickness. Therefore, illumination uniformity must be checked at the extremes of the designed operating limits. In this embodiment the system is designed to accommodate a range of 1.0 mm to 1.9 mm of combined slide, mounting media and coverslip thickness variations.

Figure 8:
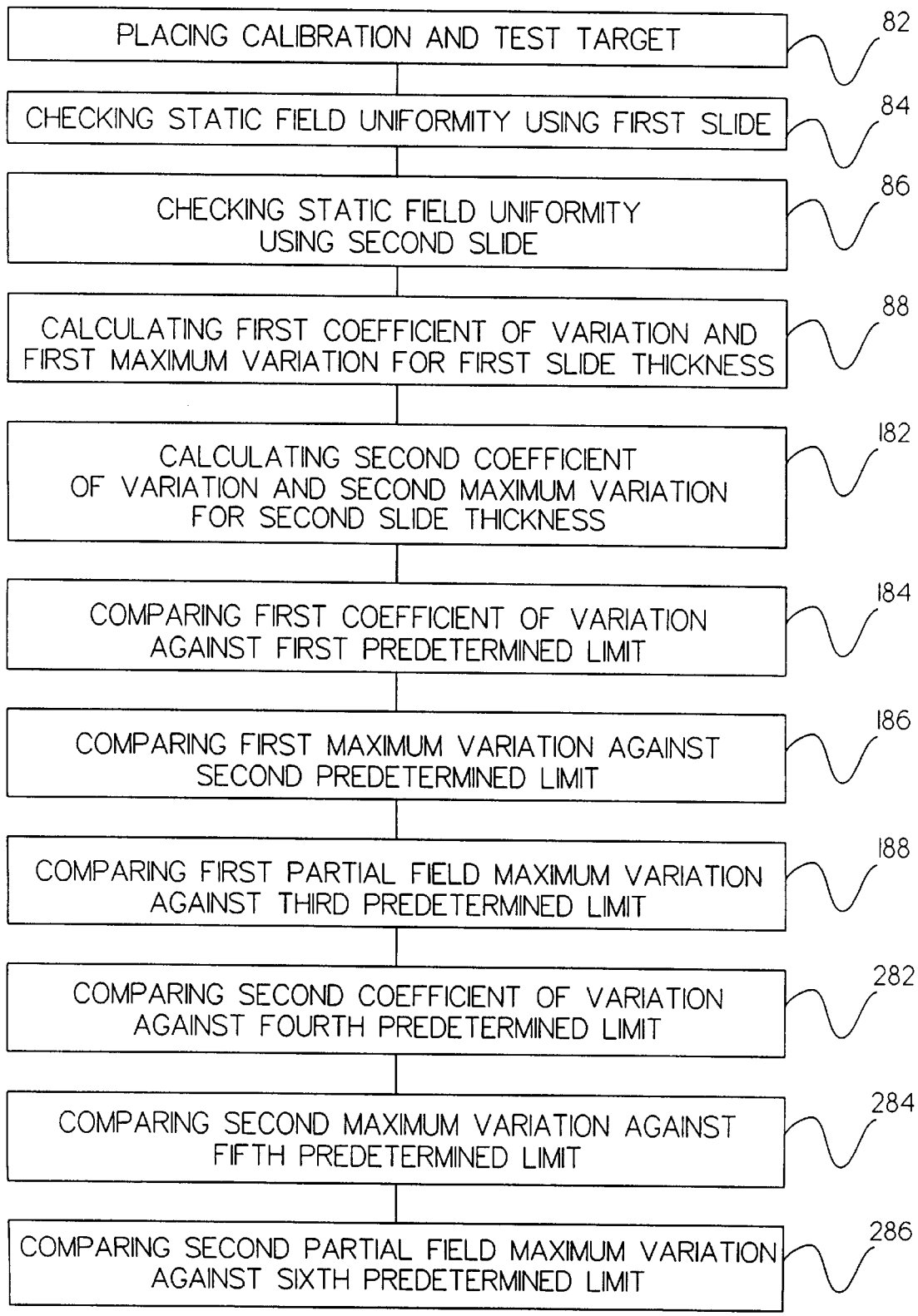
FIG. 8 shows a flow diagram of one method of the invention for checking illumination variation due to specimen thickness variation.

FIG. 8 shows a flow diagram of one method of the invention for checking specimen thickness variation. A calibration and test target is introduced into the optical path 82. However, this time different parts of the calibration plate are used. The calibration plate also contains clear areas that are 1.0 mm and 1.90 mm thick. These areas are used correspondingly to conduct the thickness test. In this test the static field uniformity test, described above is run twice—once with a 1.0 mm thick slide and a second time with a 1.9 mm thick slide at process steps 84 and 86 respectively. The coefficient of variation and maximum variation, for both the full and partial fields, are recorded for each slide thickness 88. A second coefficient of variation and a second maximum variation, for both the full and partial fields, are recorded for the second slide thickness 182. The results are evaluated by comparing the first coefficient of variation against a first predetermined limit 184, comparing the first maximum variation against a second predetermined limit 186, comparing the first maximum partial field variation against a third predetermined limit 188, comparing the second coefficient of variation against a fourth predetermined limit 282, comparing the second maximum variation against a fifth predetermined limit 284, and comparing the second maximum partial field variation against a sixth predetermined limit 286.

In one embodiment of the invention the following limits were employed.

TABLE 6

Parameter Results and Limits Comparison for Thin Slide Field Uniformity

| Parameter Description | Actual Value | Limits |
|---|---|---|
| Coefficient of variation: | 0.6% | <1.0% |
| Maximum % variation (full field): | 2.6% | <6.0% |
| Maximum % Variation (partial field): | 1.7% | <3.0% |

TABLE 7

Parameter Results and Limits Comparison for Thick Slide Field Uniformity

| Parameter Description | Actual Value | Limits |
|---|---|---|
| Coefficient of variation: | 0.6% | <1.0% |
| Maximum % variation (full field): | 2.6% | <6.0% |
| Maximum % Variation (partial field): | 1.7% | <3.0% |

Figure 9:
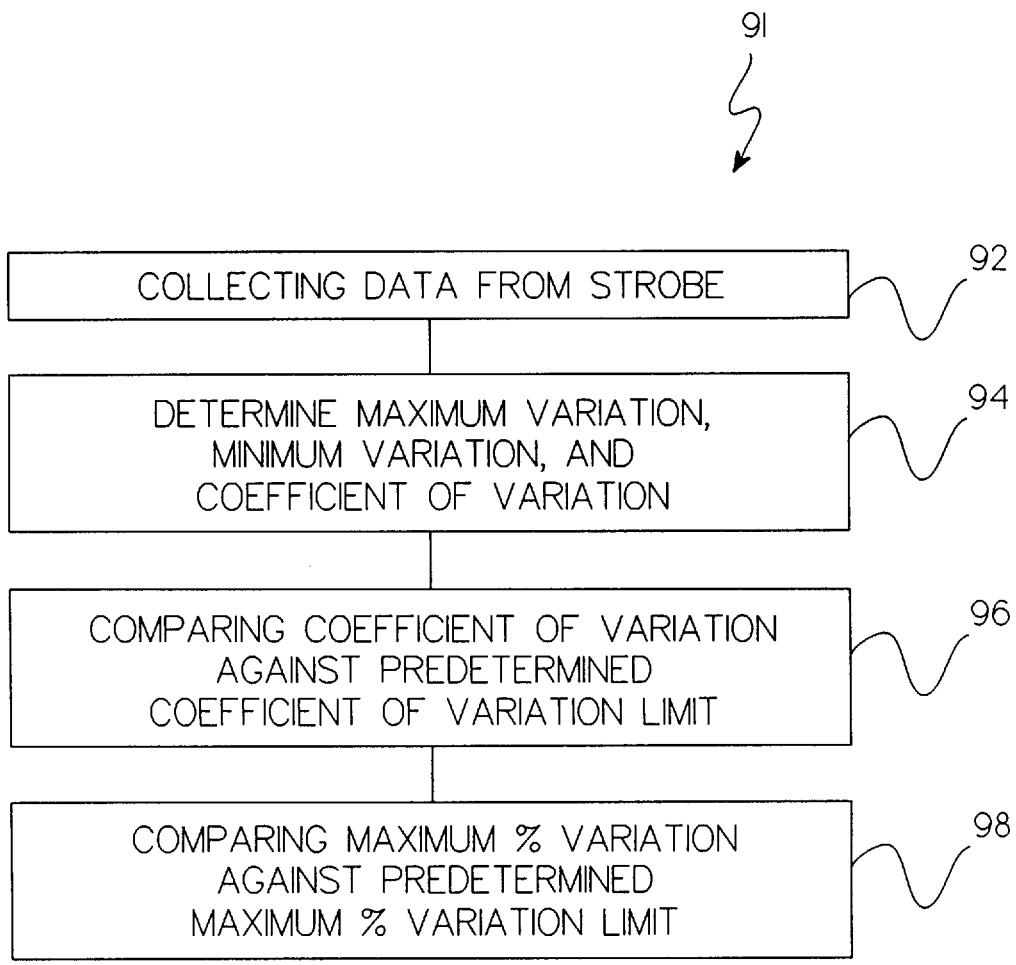
FIG. 9 shows a flow diagram of one method of the invention for checking strobe repeatability.

Referring now to FIG. 9, a flow diagram of one method of the invention for checking strobe repeatability 91 is shown. Data from the strobe sensor 76 may be collected during the global illumination test at process step 92. Data collected from the strobe may be proportional to strobe output intensity. From the collected one hundred strobe flashes, the maximum, minimum and coefficient of variation of strobe output is determined at process step 94. The results are evaluated as follows according to Table 8 at process step 98.

TABLE 8

Parameter Results and Limits Comparison for Strobe Repeatability Test

| Parameter Description | Actual Value | Limits |
|---|---|---|
| Coefficient of variation: | 0.6% | <1.0% |
| Maximum % variation: | 2.9% | <5.0% |

Calibration Plate Cleanliness

Figure 10:
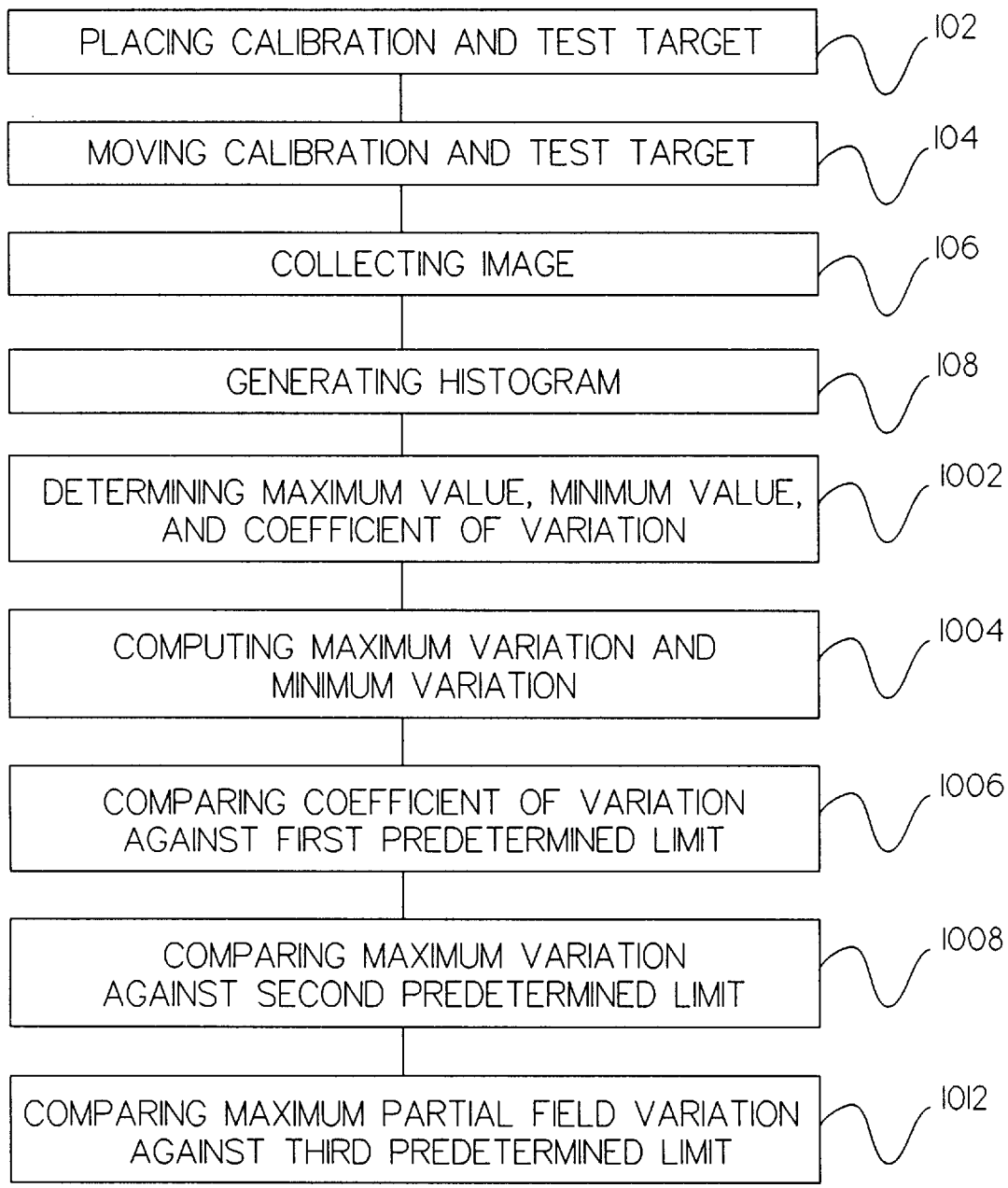
FIG. 10 shows a flow diagram of one method of the invention for checking calibration plate cleanliness.
Figure 11:
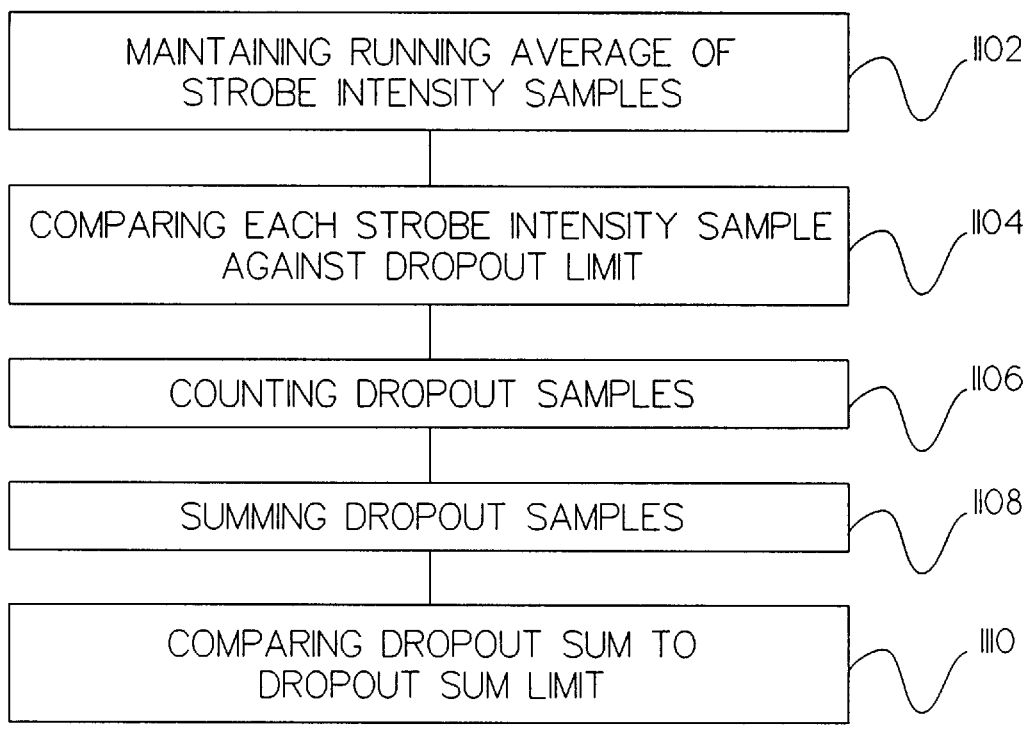

Referring now to FIG. 10, a flow diagram of one method of the invention for checking calibration plate cleanliness is shown. The calibration and target plate advantageously has a specified clear area for calibration of pixel gain and offset. At calibration, the calibration plate is lowered to remove its surfaces from the focal plane of the objectives. However, because of wide depth of field of some magnifications, large debris on the calibration plate may be visible. This can cause an erroneous calibration. The calibration plate dirt check test is run to check for this condition.

In one method for checking calibration plate cleanliness, a calibration and test target is introduced into the optical path at process step 102. At process step 104, the calibration and test target is moved about 50 microns in both x- and y-directions from its typical test and calibration position. This is done to highlight potentially contaminated areas that may be masked by the instrument pixel calibration. An image is collected and a histogram is generated at process steps 106 and 108 respectively. At step 1002 a coefficient of variation, for both full and partial field maximum variations are computed from the histogram data. At process step 1004 a maximum variation and a minimum variation are computed for a predetermined portion of the field-of-view by ignoring outlying pixels of the histogram so as to provide a measure of the calibration plate cleanliness. The results are evaluated by comparing the coefficient of variation against a first predetermined limit at step 1006, comparing the maximum variation against a second predetermined limit at step 1008 and comparing the partial field maximum variation against a third predetermined limit 1012.

One example of predetermined limits which may be employed are listed below.

Coefficient of variation: <1.0%

Maximum % variation (full field): <6.0%

Maximums % Variation (partial field): <3.0%

Strobe Dropout Monitor

Figure 11:
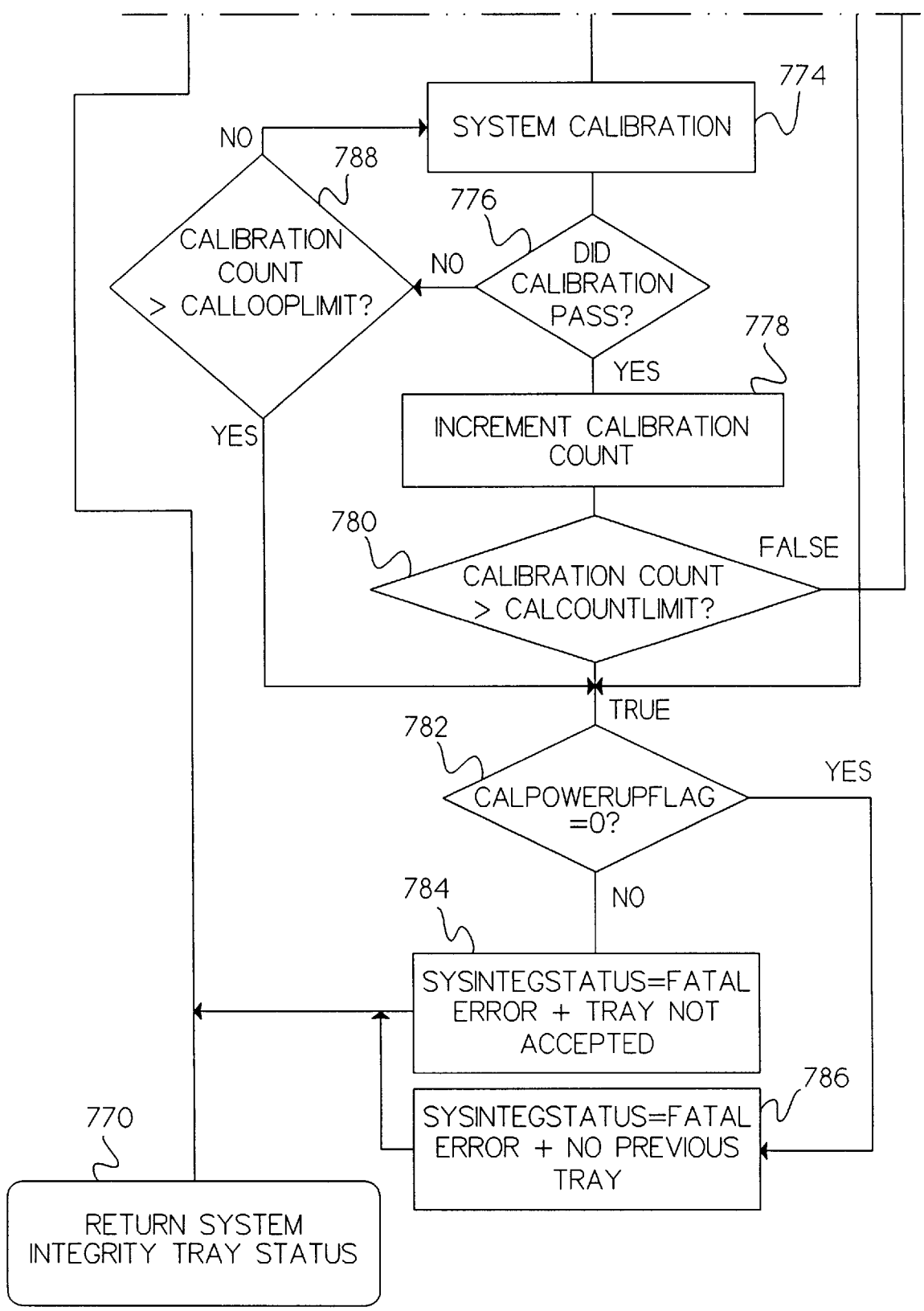
FIG. 11 shows a flow diagram of one method of the invention for checking strobe drop out.

Referring now to FIG. 11, a flow diagram of one method of the invention for checking strobe drop out is shown. The method includes the steps of maintaining a running average of strobe intensity samples over a predetermined number of samples 1102, comparing each strobe intensity sample against a dropout limit 1104 which may be comparing each instantaneous strobe sample against the running average of strobe intensity values, counting each strobe intensity sample which does not meet the dropout limit as a dropout sample to obtain a plurality of dropout samples 1106 where the count may be computed by counting all occurrences where the instantaneous value and running average differ by more than the dropout limit, summing the plurality of dropout samples occurring during a predetermined event to produce a dropout sum 1108, and after the predetermined event, comparing the dropout sum to a dropout sum limit 1110.

In operation, occasionally, a strobe lamp will generate arcs that are erratic in position or energy output. This type of behavior can cause the illumination system to produce a field of lower illuminance. In this embodiment of the invention, the strobe is constantly monitored. A running average of the strobe is maintained consisting of 500 samples. All samples taken that exceed 5% of the running average are considered drop outs. The strobe drop out monitor test sums these dropouts during a tray of processing (8 slides), or roughly one hour. After processing a tray, the sum is compared to a limit. In this embodiment, the total of acceptable errant flashes is around 0.03%. The limit is evaluated against a standard as follows: strobe dropouts greater than 5%: <30 dropouts per tray.

System Linearity Test

Figure 14:
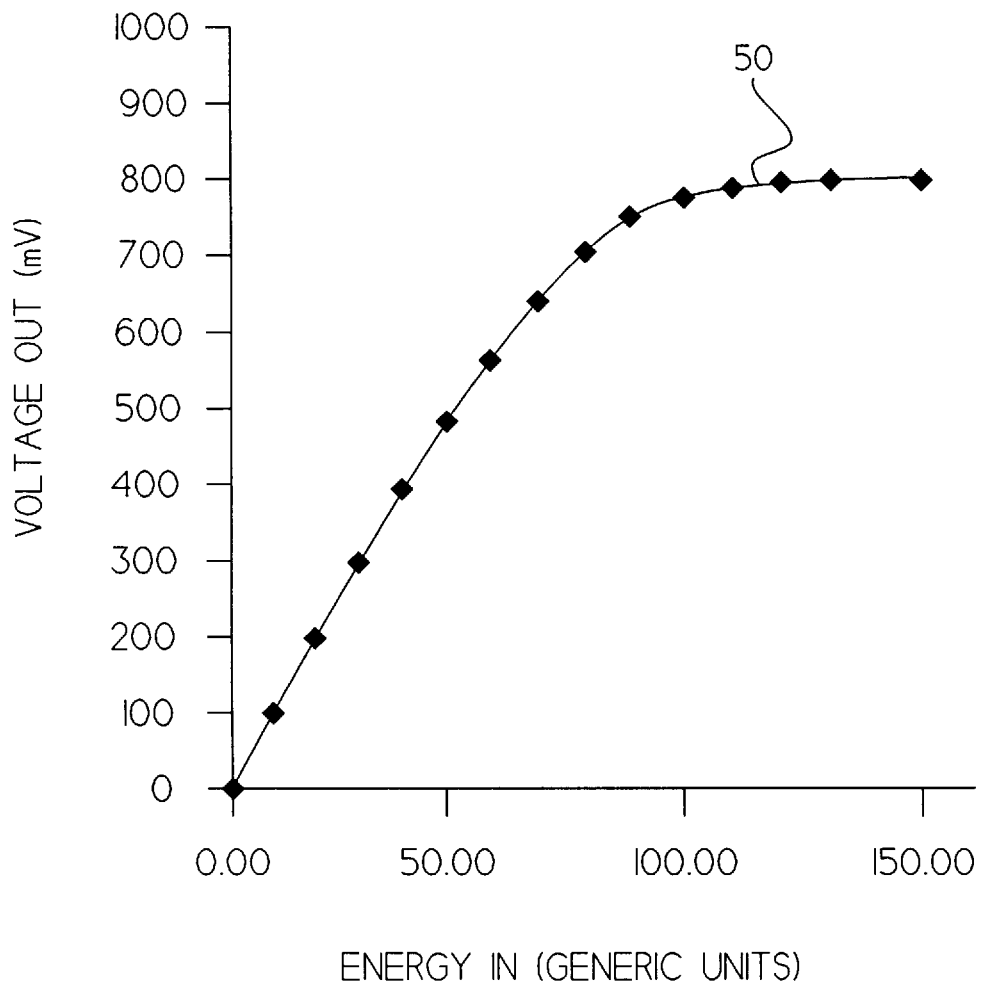
FIG. 14 shows a linearity profile for an automated cytology system.

Referring now to FIG. 14, a linearity profile for an automated cytology system is shown. The profile is plotted with respect to a horizontal axis representing energy in generic units and a vertical axis representing voltage output in millivolts. Linearity of response is the change in voltage out of a system with respect to the light level input. Note the characteristic saturation curve 50. In the region below 600 mV, corresponding to an input energy of about 70 units, the profile indicates that the system responds fairly linearly to a change in input energy. For voltages above 600 mV, the system appears to generate less of a voltage output for each additional energy input. After about 110 energy units of input, the system is saturated and no longer produces a change in voltage for a corresponding change in energy input.

Many components influence the linearity of an image capture system, such as an automated cytology analysis system, including the detector and subsequent electronics, optical components, stray light baffling and other elements. Most systems are designed for operation in the linear region. However, if a system is allowed to operate slightly into the nonlinear region, some dynamic range can be gained. This is often the case in many designs. In these types of systems it is critical that the system operate with the same characteristic linearity curve over time and temperature. Therefore, it is highly desirable to test system linearity.

Figure 15:
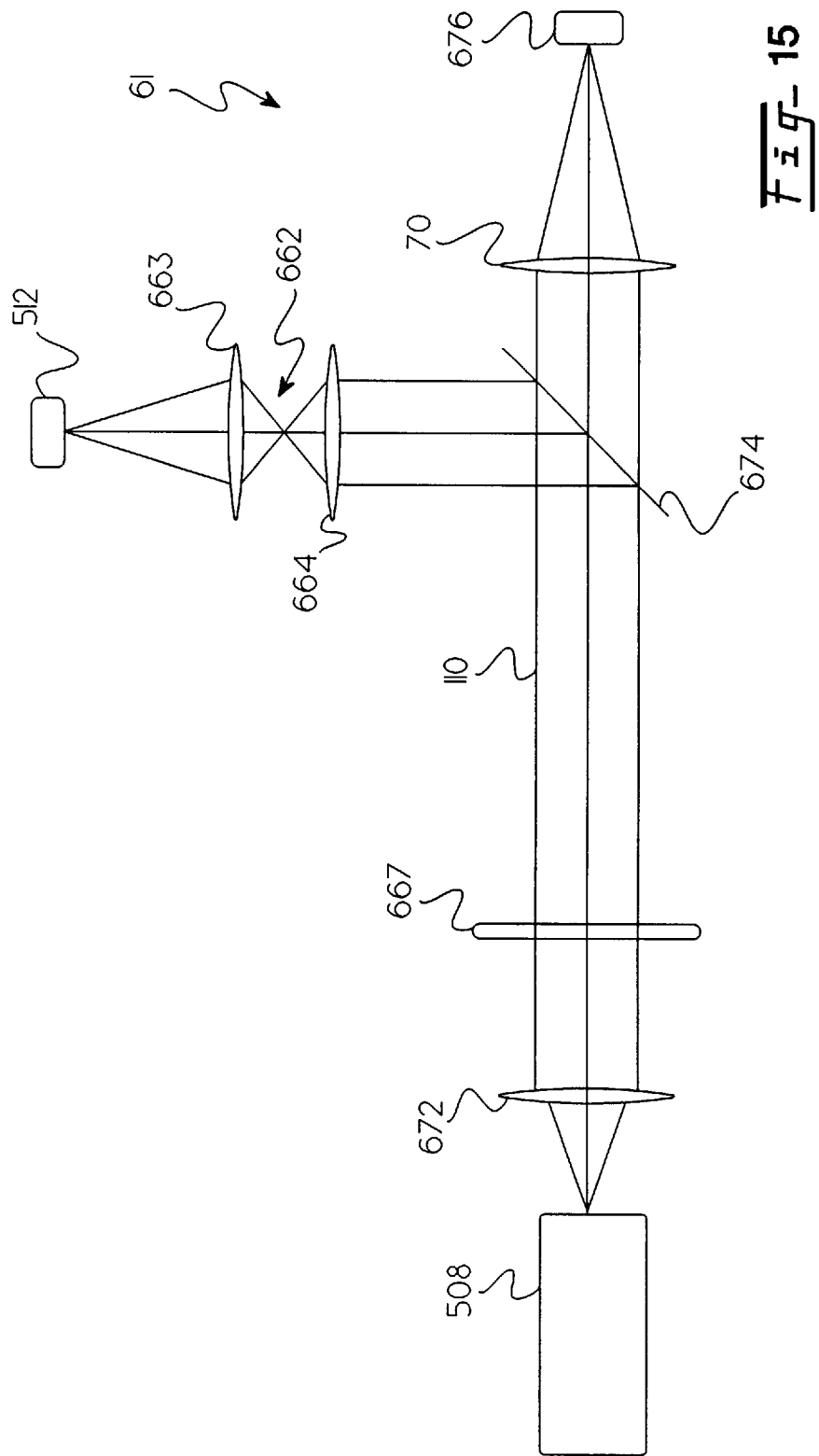
FIG. 15 schematically illustrates one example of a system apparatus used for testing linearity.

One example of a system linearity test apparatus is shown in FIG. 15. The linearity testing apparatus 61 comprises an illumination source 508, a camera 512, a specimen plane 662, a first lens 663, a second lens 664, a beam splitter 674, a photodetector 676, a neutral density wedge 667, a third lens 672, and a fourth lens 70. The first lens 663 may comprise an objective of an automated microscope, where the objective is selected to have a predetermined magnification and is positioned over the nominal clear area 34 of the calibration and target plate 1. It is advantageous to run the linearity test using objectives having high power and low power magnifications.

In one example using an automated microscope having two objectives, 20× and 4×magnifications are tested. The neutral density wedge 667 is positioned to yield a desired illumination level. A single image is acquired by the imaging apparatus and a mean pixel intensity is computed to characterize the camera response at the selected illumination level. The neutral density wedge 667 is positioned at another illumination level. A single image is again acquired and a second mean pixel intensity is computed to characterize the camera response at the second selected illumination level. This process is repeated for six different regions, in one example, to characterize the linearity profile of the system.

Figure 16:
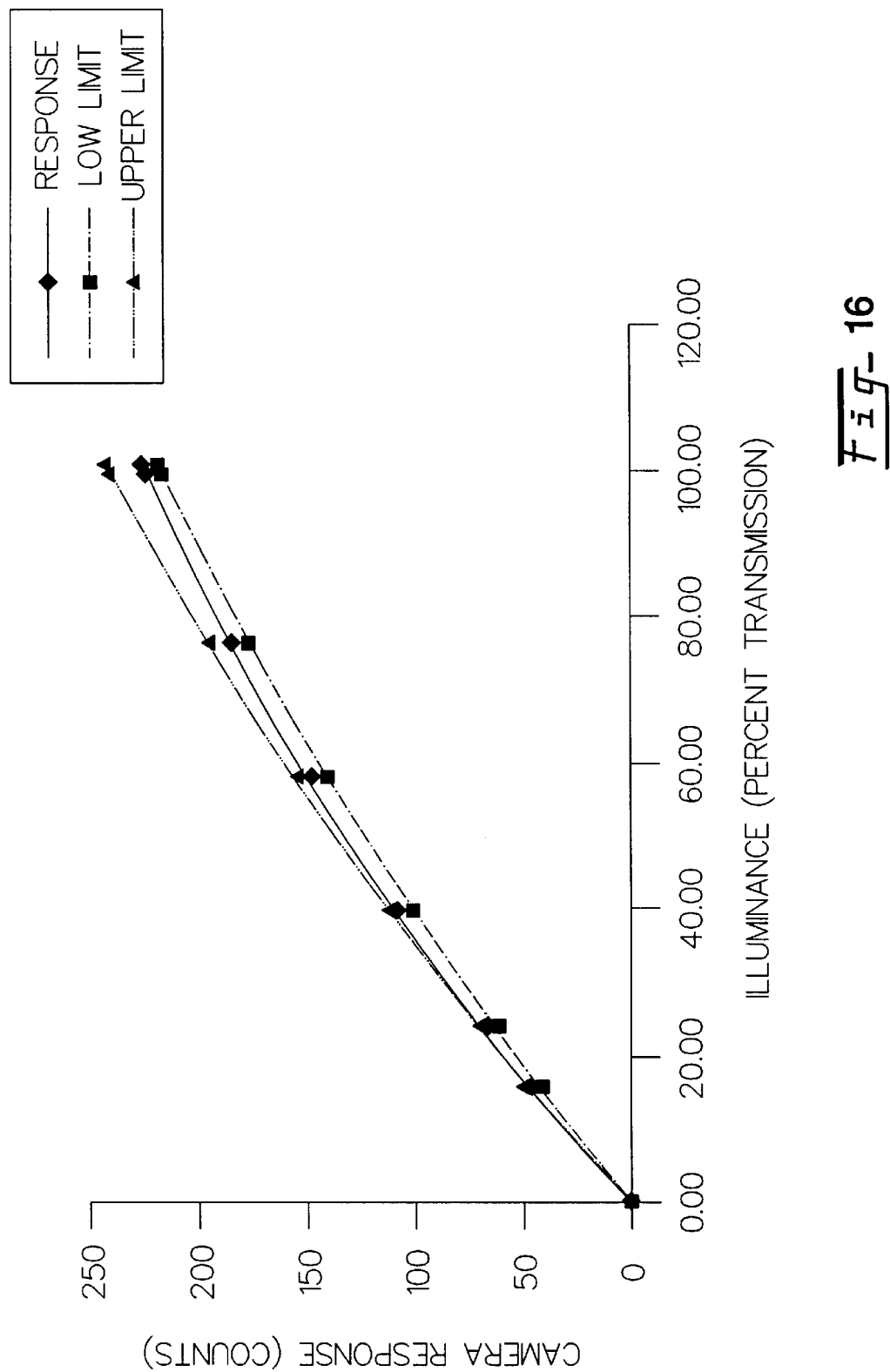
FIG. 16 is a linearity plot of an illumination sensor reading on the abscissa axis and the camera reading on the ordinate axis.

The embodiment of FIG. 15 employs a double beam system in which the illumination level is set by rotating the circular linearly variable neutral density wedge 667. Feedback for setting a selected illumination level is provided by the sensor 676 that receives light split off the main optical path 110 before it illuminates a specimen at specimen plane 662. FIG. 16 is a linearity plot which is essentially a plot of the illumination sensor reading on the abscissa axis and the camera reading on the ordinate axis. Table 10 shows the data plotted in FIG. 16 in tabular form. The sensor is previously calibrated to ensure its linearity. Therefore, the linearity plot is fundamentally a linearity plot of the system. The limits of the linearity test are dynamic and may be determined by the formula below. Limits on the camera response may be calculated as a function of the illumination or sensor response level. The sensor response level is the sensor response measured at a certain illumination as a percentage of the sensor response measured at 100% illumination.

The formula for calculating the camera response limit is given as limit=(sensor response level)*slope+intercept.

Using this formula, the camera response limits may be determined with the information provided in Table 1.

TABLE 9

Linearity Limits

| Sensor Response | Minimum | | Maximum | |
|---|---|---|---|---|
| Level | Slope | Intercept | Slope | Intercept |
| 0–10% | 2.60 | 4.00 | 3.00 | 6.00 |
| 10–20% | 2.50 | 5.00 | 2.70 | 9.00 |
| 20–35% | 2.47 | 5.67 | 2.47 | 13.67 |
| 35–50% | 2.13 | 17.33 | 2.40 | 16.00 |
| 50–75% | 2.08 | 20.00 | 2.24 | 24.00 |
| 75–105% | 1.88 | 35.00 | 2.04 | 39.00 |

TABLE 10

Linearity Test Data, AP300
20X Camera Linearity

| Illumination Level Illuminance | Camera Resp. Response | Minimum Low Limit | Maximum Upper Limit |
|---|---|---|---|
| 0.00% | 5.07 | 4 | 6 |
| 16.51% | 52 | 46.27 | 53.58 |
| 24.21% | 71.34 | 65.48 | 73.48 |
| 39.62% | 108,89 | 101.73 | 111.1 |
| 56.14% | 143.62 | 136.77 | 149.75 |
| 77.05% | 184.92 | 179.86 | 196.19 |
| 99.07% | 230.3 | 221.25 | 241.1 |
| 100.17% | 232.31 | 223.32 | 243.35 |

Modulation Transfer Function Test

Figure 17:
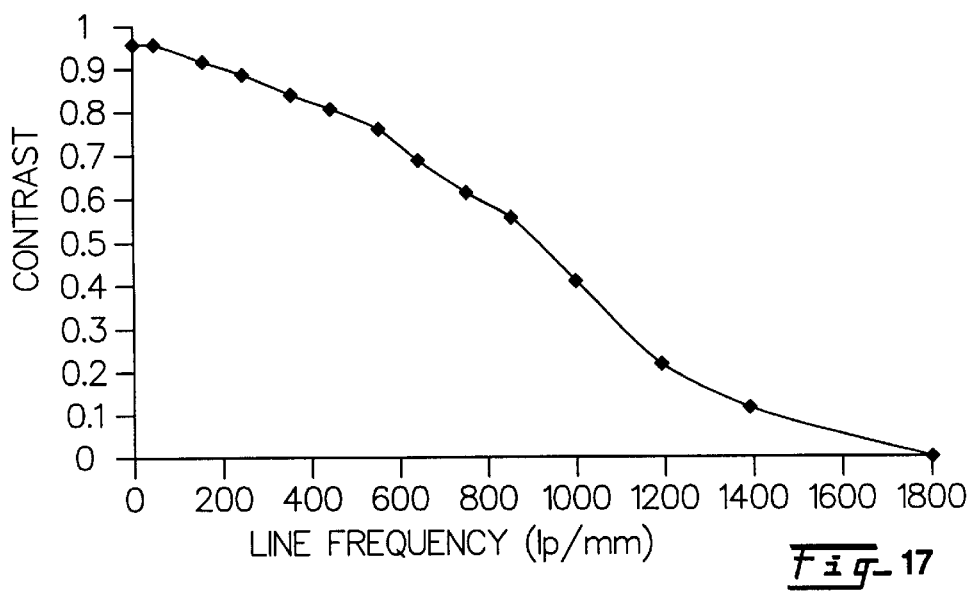
FIG. 17 shows an example of a modulation transfer function as employed in one embodiment of the invention.
Figure 18A:
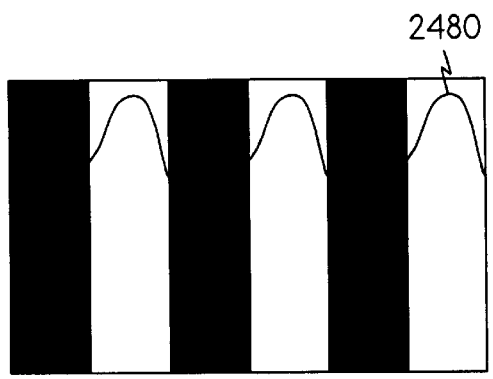
FIGS. 18A, 18B, 18C and 18D show bar patterns of progressively increasing spatial frequency and an intensity profile of those bar patterns in an image plane.
Figure 18B:
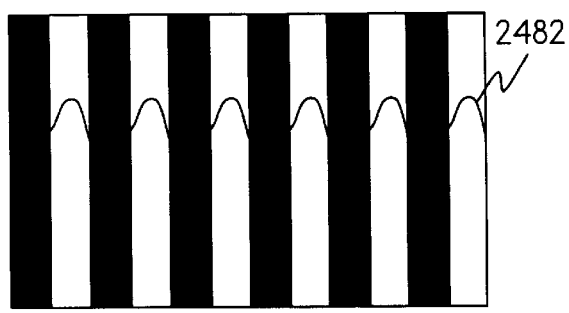
Figure 18C:
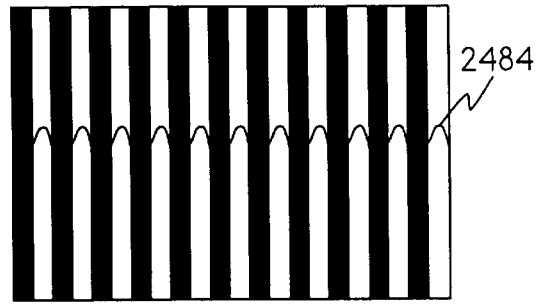
Figure 18D:
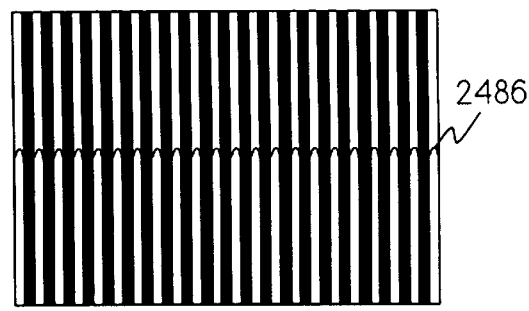

A Modulation Transfer Function (MTF) test characterizes the frequency response of the system. Modulation transfer functions are well known and typically comprise a curve of contrast in the image plane versus spatial line frequency of a sinusoidal input in the object plane. See, for example, Smith, *Modern Optical Engineering*, pp.308–323, McGraw-Hill Book Company, 1966. FIG. 17 shows an example of an MTF. As the line frequency of the object increases, that is, as objects get smaller and closer together, the ability of an optical system to provide contrast in the image decreases. FIGS. 18A, 18B, 18C and 18D show bar patterns of progressively increasing spatial frequency. Also shown are intensity profiles 80, 82, 84 and 86 of those bar patterns in the image plane. As line frequency increases the contrast in the image plane decreases. Beyond a predetermined cutoff frequency, the contrast is zero (i.e. there is no modulation in the image). Modulation is defined as follows:

Modulation=(max−min)/(max+min)

where: max and min are the maximum and minimum intensity values in the image plane.

There are typically two methods for generating an MTF curve. The first method involves conducting a series of contrast measurements over a set of discrete bar patterns. The contrast is measured at each bar pattern and a pseudo MTF curve is gradually generated. The first method does not actually generate an MTF curve because a true MTF test has a sinusoidal input. Sinusoidal targets are very difficult to generate and usually cannot be generated at even modestly high frequencies. Therefore, a bar pattern, which generates a square wave, is usually used. Although this is not true MTF, it is common practice. Another problem with the first method is that bar patterns, even square wave patterns, are difficult to generate at very high frequencies such as those above 250 lp/mm (i.e., 2 micron line widths). The problem is that many optical systems have a cutoff frequency around 2000 lp/mm. Therefore, this method can only test the pseudo (square wave) MTF in the lower part of the MTF curve up to 250 line pairs per millimeter.

Another method used to test MTF employs imaging a very small slit or small point of light in the object plane. If the slit or point is small relative to the optical resolution of the system, the resulting distribution of light in the image plane is referred to as the line or point spread function respectively. The convolution of the point or line spread function for a given optical system with a sinusoidal object (as an input function) yields the image (incorporating the contrast and phase shift) of that object for the system under test. Therefore, an MTF plot can be constructed by determining the line spread function in the manner stated and convolving it with a series of input sinusoids of varying frequency to determine the MTF function for a system. This method is often employed in MTF test systems for single lenses of low numeric aperture. In order for this approach to yield accurate results, two conditions must be met. First, the test sample (slit or point) must be small relative to the optical resolution of the system. Second, the magnification coupled with the pixel (or sample) size of the system must result in an accurate quantification of the point spread function. These two constraints are often difficult to meet. The following example demonstrates this fact. Consider a 20× optical system with a numeric aperture of 0.75 and a detector pixel size of 10 microns. In this system the diffraction limited optical resolution in the object plane is 0.4 microns (as determined by the formula below). In accordance, the entire Airy Disk (TM) diameter is only 0.8 microns.

$\delta$ radius=0.61 $\lambda$/NA where: $\lambda$ is 0.500 microns

Likewise the pixel size in the object plane is {pixel size/magnification} or 10 microns/20=0.5 microns pixels. This case illustrates both problems with this method. First, it is difficult to manufacture a slit with a sub-micron width. Second, the pixel size of 0.5 microns is inadequate to sample a line or point spread function with an Airy Disk (TM) diameter of 0.8 microns. There are not enough samples to reconstruct the function.

Both of the methods discussed above are inadequate to characterize the MTF of many optical systems. The method disclosed herein alleviates these shortcomings.

The method of the invention employs a single low frequency bar pattern to determine an actual MTF in a given axis. The frequency is low and the pattern is a square wave. Therefore, the target is easy to manufacture. The method of the invention also allows the MTF to be determined with respect to the cutoff frequency of the optical system and is relatively independent of the pixel size of the detector.

Figure 19A:
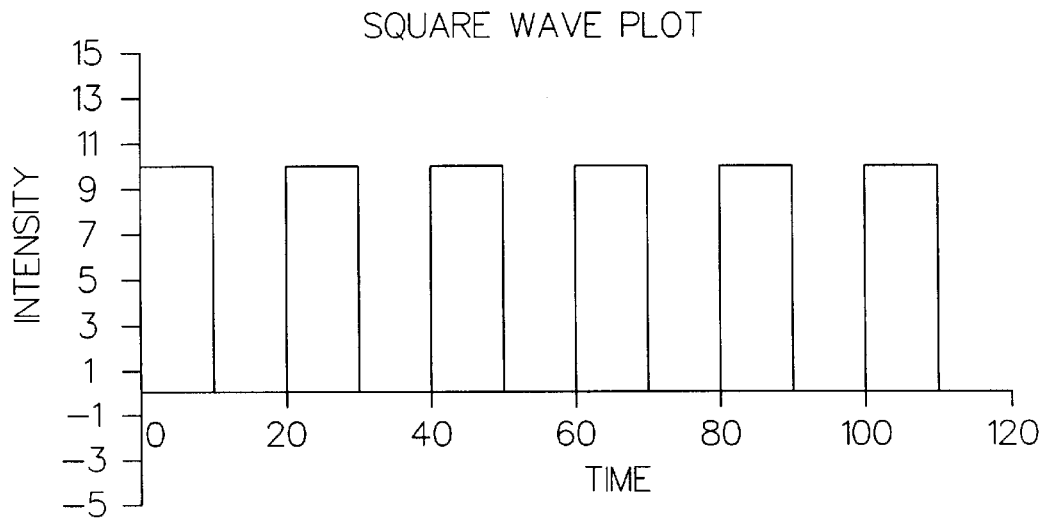
FIG. 19A shows a square wave plot for a theoretically perfect square wave.
Figure 19B:
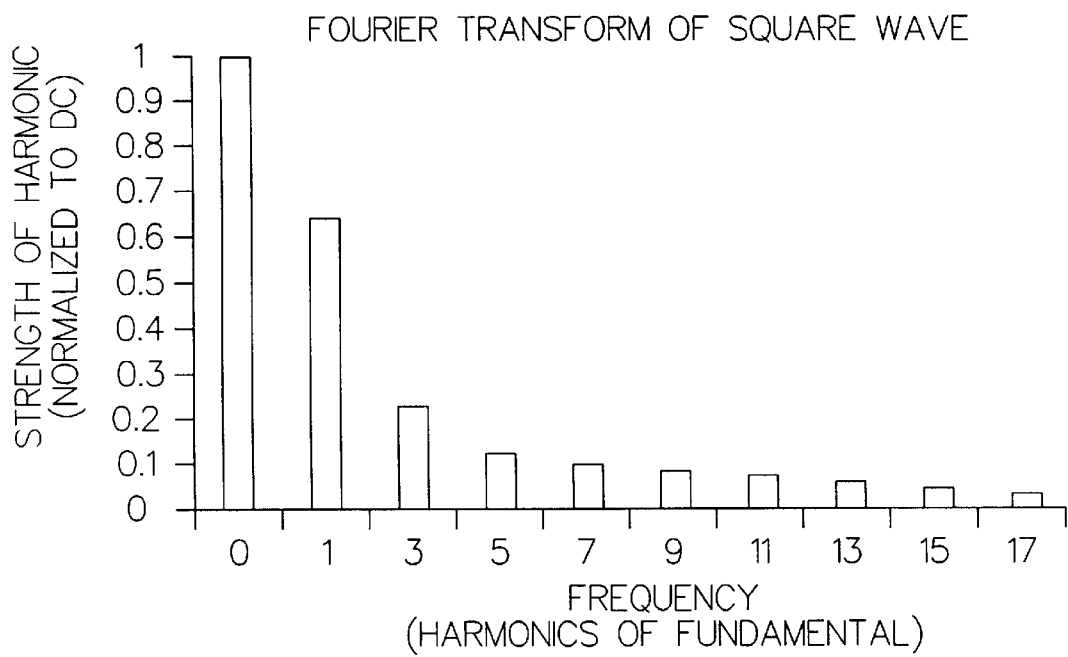
FIG. 19B shows the Fourier transform of a perfect square wave.

Fourier theory states that a periodic function of x with a spatial period of $\lambda$, can be synthesized by a summation of harmonic functions whose wavelengths are integral submultiples of $\lambda$ (that is $\lambda$, $\lambda/2$, $\lambda/3$ . . . ). This theory may be utilized judiciously in the case of MTF determination for an optical system. In this case, a square wave or bar target may be employed when one considers that a square wave is a summation of sinusoids whose wavelengths are the odd harmonics ($\lambda/3$, $\lambda/5$, $\lambda/7$ . . . ) of the original square wave frequency, $\lambda$. FIG. 19A shows a square wave plot. The Fourier transform of a perfect square wave, as represented in FIG. 19A, is shown in FIG. 19B. Note, the strength of the DC component or the 0 frequency point is half the intensity of the bright section of the input square wave. The DC component is equivalent to Ao/2, where Ao is the peak to peak intensity, that is, twice the amplitude, of the input square wave. Likewise, the strength of the fundamental frequency or first harmonic is, $4Ao/\pi$. In accordance with the equation for the Fourier series expansion seen below, the strength of each additional harmonic is 1/N the strength of the fundamental frequency. For example, the contribution of the 5th harmonic is ⅕ that of the fundamental frequency.

Fourier Series Expansion for Square Wave:

$$f(x) = Ao/2 + 4Ao/\pi(\sin kx + \tfrac{1}{3} \sin 3kx + \tfrac{1}{5} \sin 5kx + \ldots)$$

The MTF of a real optical system may now be measured. A calibration and test target with image primitives of periodic structure, such as a bar target, may be placed in the object focal plane of the image collection system. An image of this image primitive may be acquired by the detector of the image collection system. Using discrete Fast Fourier Transform (FFT) techniques, the Fourier transform of the acquired image may be determined. The strength and frequency of the signal spectral peaks in the FFT may be quantified. It should be noted, as in the case of the bar target, that each signal peak represents one of the constituent sinusoids that comprise the square wave image of the bar target. Each signal spectral peak from the FFT of the acquired image can be divided by an equivalent signal spectral peak from the Fourier transform of a square wave, of scaled amplitude, representative of the bar target magnified by a reference amount. The amplitude of the square wave is scaled to match that produced by the perfect image of a bar target in the automated cytology system. The reference amount of magnification is equivalent to that expected of the image collection system. FIG. 19B shows the Fourier transform of such a square wave. Degradation in the strengths of the signal peaks between the FFT of the acquired image and Fourier transform of the representative square wave comprise the modulation loss created by the optical and electronic imaging systems. Those skilled in the art, having the benefit of this disclosure, will appreciate that a windowing function may be advantageously applied to the image prior to computing the FFT. A perfect optical system that suffers no loss in modulation from diffraction, aberrations, manufacturing tolerances or signal processing should reproduce the square wave pattern perfectly in the image plane. In this case, the FFT would produce a plot identical to that shown in FIG. 19B. It should also be noted that a perfect optical system is an impossibility primarily due to diffraction effects. A plot of the ratios of the strengths of each of the constituent harmonic frequencies is really a plot of the MTF of the system. Therefore, if a relatively low frequency square wave is used as the input waveform in the object plane, one could quantify the modulation of numerous frequencies out to the cutoff frequency.

One of the true strengths of the method of the invention lies in the ability to determine the MTF of the image collection system well beyond the classical Nyquist sampling rate of the image collection system detector. In this case, the signal peaks representing the higher order harmonics are present in the FFT, however, they appear as foldback peaks or aliases. These peaks fold back from the sampling frequency back onto the original harmonics. Therefore, a fundamental frequency may be chosen in conjunction with a sampling frequency of the image collection system detector to allow the foldback frequencies to appear in between the lower order harmonics. The sampling frequency may be advantageously determined by the cameras pixel size if the sample rate of the digital processor of the image collection system is synchronous and equal to that of the camera. With this method, the MTF may be determined well beyond the half (Nyquist) sampling frequency of the detector.

Figure 20:
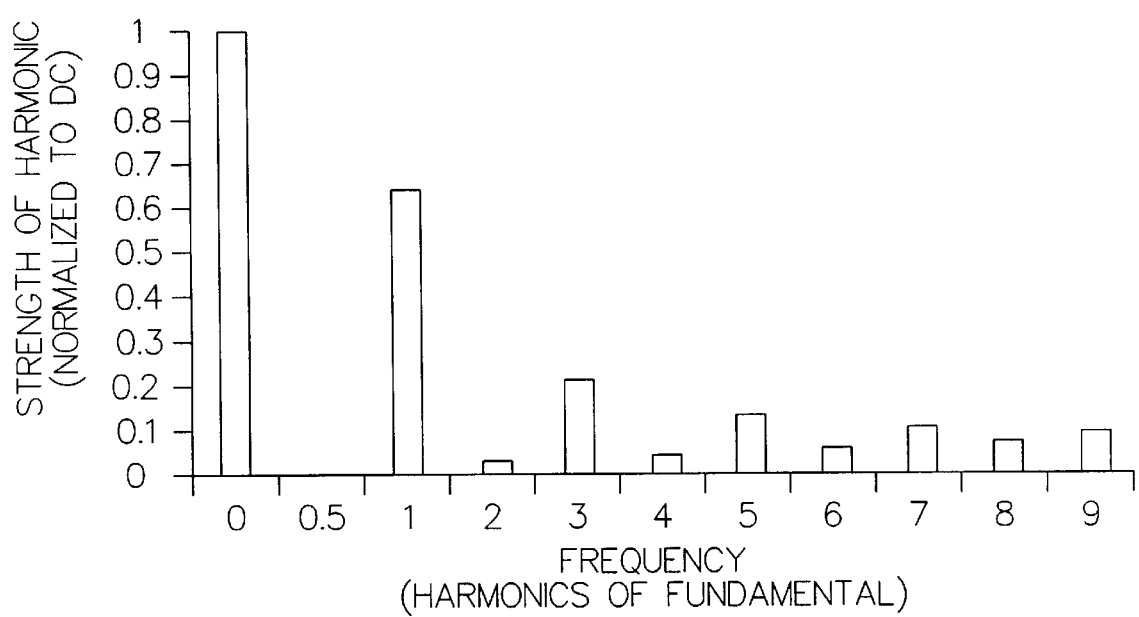
FIG. 20 shows one example of an FFT foldback for MTF determination beyond the detector sampling frequency.

FIG. 20 shows one example of an FFT foldback for MTF determination beyond the detector sampling frequency. Note, in this example, the sampling frequency of the detector was equal to a frequency of 9.5 times the fundamental. Therefore the higher harmonics, 11th, 13th etc., folded back into the location of the (missing) even harmonics. Note, that the strength of these harmonics is equal to the strength of the harmonics seen in FIG. 19B.

These techniques were employed to measure the MTF of an actual imaging system. The results are shown in Tables 11 and 12. Note the plots give the MTF at three locations in the Field of view for each direction. A vertical bar pattern with a line frequency of 50 lp/mm was used to determine the horizontal MTF. Likewise, a horizontal bar pattern was used for determination of vertical MTF. The optical system comprised a microscope objective with 20×magnification, 0.75 NA collection aperture and 0.45 NA illumination aperture. The camera pixel size was 11 microns in the image plane and 0.55 microns (11 microns/20×) in the object plane. The data is given for MTF in the object plane. This test was taken during operation of an automated biological specimen imaging and analysis system by intercepting the optical path with a glass target simulating a microscope slide with horizontal and vertical 50 lp/mm square wave targets.

TABLE 11

Vertical MTF
20X Vertical MTF for Three Portions of Field of View

| Freq Range | | Left | | | Center | | | Right | | |
| --- | --- | --- | --- | --- | --- | --- | --- | --- | --- | --- |
| min | max | freq | mtf | min | freq | mtf | min | freq | mtf | min |
| .0 | 0 | 0 | 0.951 | 0.839 | 0 | 0.939 | 0.839 | 0 | 0.937 | 0.839 |
| 48.0 | 52 | 49.7 | 0.951 | 0.91 | 49.7 | 0.95 | 0.91 | 49.7 | 0.953 | 0.91 |
| 144.0 | 156 | 149.1 | 0.924 | 0.87 | 149.1 | 0.925 | 0.87 | 149.1 | 0.928 | 0.87 |
| 240.0 | 260 | 248.5 | 0.885 | 0.819 | 248.5 | 0.885 | 0.819 | 248.5 | 0.893 | 0.819 |
| 336.0 | 364 | 348 | 0.845 | 0.75 | 348 | 0.84 | 0.75 | 348 | 0.85 | 0.75 |
| 432.0 | 468 | 447.4 | 0.799 | 0.66 | 447.4 | 0.798 | 0.66 | 447.4 | 0.803 | 0.66 |
| 528.0 | 572 | 546.8 | 0.76 | 0.55 | 550.4 | 0.743 | 0.55 | 550.4 | 0.756 | 0.55 |
| 624.0 | 676 | 649.8 | 0.675 | 0.449 | 649.8 | 0.683 | 0.449 | 649.8 | 0.698 | 0.449 |

TABLE 11-continued

Vertical MTF
20X Vertical MTF for Three Portions of Field of View

| Freq Range | | Left | | | Center | | | Right | | |
|---|---|---|---|---|---|---|---|---|---|---|
| min | max | freq | mtf | min | freq | mtf | min | freq | mtf | min |
| 730.0 | 780 | 749.2 | 0.607 | 0.349 | 749.2 | 0.623 | 0.349 | 749.2 | 0.632 | 0.349 |
| 816.0 | 884 | 848.7 | 0.545 | 0.250 | 848.7 | 0.542 | 0.259 | 848.7 | 0.549 | 0.259 |

TABLE 12

Horizontal MTF
20X Horizontal MTF for Three Portions of Field of View

| Freq Range | | Left | | | Center | | | Right | | |
|---|---|---|---|---|---|---|---|---|---|---|
| min | max | freq | mtf | min | freq | mtf | min | freq | mtf | min |
| .0 | 0 | 0 | 0.953 | 0.839 | 0 | 0.955 | 0.839 | 0 | 0.95 | 0.839 |
| 48.0 | 52 | 49.7 | 0.928 | 0.899 | 49.7 | 0.925 | 0.899 | 49.7 | 0.926 | 0.899 |
| 144.0 | 156 | 149.1 | 0.813 | 0.769 | 149.1 | 0.809 | 0.769 | 149.1 | 0.811 | 0.769 |
| 240.0 | 260 | 248.5 | 0.659 | 0.61 | 248.5 | 0.654 | 0.61 | 248.5 | 0.658 | 0.61 |
| 336.0 | 364 | 348 | 0.516 | 0.449 | 348 | 0.512 | 0.449 | 348 | 0.51 | 0.449 |
| 432.0 | 468 | 447.4 | 0.397 | 0.319 | 447.4 | 0.396 | 0.319 | 447.4 | 0.391 | 0.319 |
| 528.0 | 572 | 546.8 | 0.31 | 0.219 | 546.8 | 0.302 | 0.219 | 546.8 | 0.303 | 0.219 |
| 624.0 | 676 | 646.8 | 0.239 | 0.129 | 649.8 | 0.238 | 0.129 | 649.8 | 0.232 | 0.129 |
| 730.0 | 780 | 749.2 | 0.183 | 0 | 749.2 | 0.185 | 0 | 749.2 | 0.18 | 0 |
| 816.0 | 884 | 848.7 | 0.15 | 0 | 848.7 | 0.158 | 0 | 848.7 | 0.154 | 0 |

Signal to Noise Test

All the concepts taught in with respect to the method of the invention for determining a modulated transfer function described hereinabove are also employed in a signal to noise test as contemplated by the present invention. However, in the signal to noise test, all the signal peaks are summed. In addition, the rest of the bins, comprising non signal bins, of the FFT are also summed. The signal to noise ratio is the ratio of these sums. A signal to noise may thereby be developed for specific frequency regions of interest as well as for the entire spectrum. The signal to noise test steps described hereinabove were employed to determine the signal to noise ratio data seen in Table 13. The results in Table 5 are classified by portions of the spectrum. The first third is roughly the portion of the frequency spectrum between DC and 260 lp/mm. The second third is roughly the portion of the spectrum between 261 lp/mm and 572 lp/mm. The third, third is the portion of the spectrum beyond 573 lp/mm. The overall signal to noise incorporates the entire spectrum.

TABLE 13

Signal to Noise Data, 20X System
Collection Signal to Noise

| Region | Results | Limits |
|---|---|---|
| First Third: | S-N = 26.164 dB | min = 24.0 dB |
| Second Third: | S-N = 15.945 dB | min = 12.0 dB |
| Third Third: | S-N = 9.423 dB | min = 3.0 dB |
| Overall: | S-N = 28.026 dB | min = 26.0 dB |

The invention further comprises a suite of tests and a parameter monitoring method for characterizing focus illumination quality, noise floor level, focus filter frequency response, focus camera frequency response, focus camera longitudinal separation, focus camera lateral and angular alignment and closed loop accuracy of an autofocus system as used in an automated scanning instrument. The examples of tests discussed herein refer specifically by way of example to a system with a pulsed arc lamp and CCD imaging devices for primary and at least two autofocus cameras. The focus apparatus in a preferred embodiment uses an above and below focus camera frequency balancing method to determine the magnitude and direction to move to best focus. In addition, the images are passed through a set of focus filters to optimize performance for biological nuclear detail. The specifics of one example of a focus system are outlined in "Method and Apparatus For Rapid Capture of Focused Microscopic Images" by Jon Hayenga, et al., discussed further herein and incorporated herein by reference. However, the invention is not considered to be limited to the specific examples set forth herein. The concepts contained herein may be employed to other focus systems using continuous arc lamps, filament lamps, LASER sources, tube cameras, TDI sensors, PIN diodes and photomultiplier tubes.

Figure 13A:
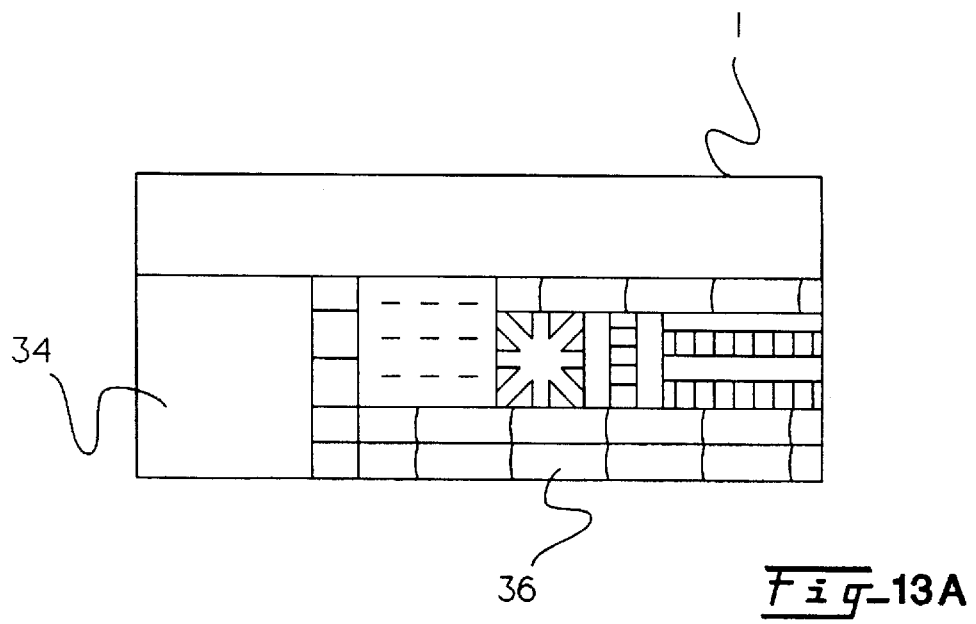
FIG. 13A shows one example of a calibration and test target or plate as used in one aspect of the invention.
Figure 13B:
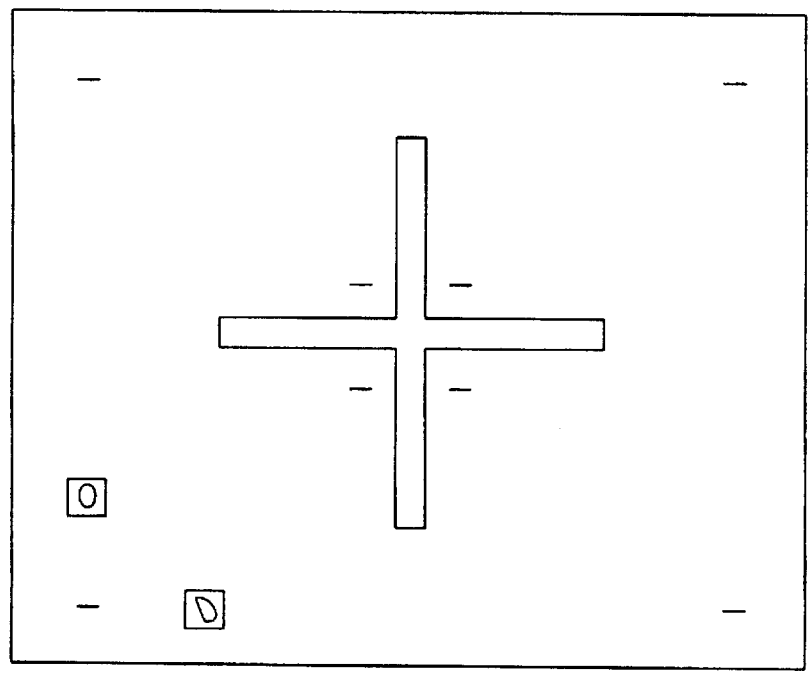
FIG. 13B shows an example of a fiducial marking.

Referring now to FIG. 13A which shows one example of a calibration and test target. Several of the processes employed by the present invention require a calibration and target plate. In the case of a transmission microscope, the calibration and test target 1 may comprise a piece of glass approximately 1.45 mm thick. The calibration and test target advantageously comprises specified clear areas 34 and image primitives such as horizontal and vertical bar targets 36. The clear area simulates a microscope slide. The clear areas are used herein for illumination and noise quality tests. The image primitives are used for frequency response and position testing. Other types of calibration markings, such as fiducial markings, may also be used. FIG. 13B shows an example of a fiducial marking. Such calibration and test target plates may be used for most transmission microscopes to simulate the optical path difference effects introduced by the substrate, coverslip and specimen media. In some embodiments of the invention, the calibration and test target may be advantageously mounted onto a conventional cantilever arm for ease of placement into the optical path in proximity to a position where a specimen would normally be positioned.

Focus System Illumination Quality

Figure 21:
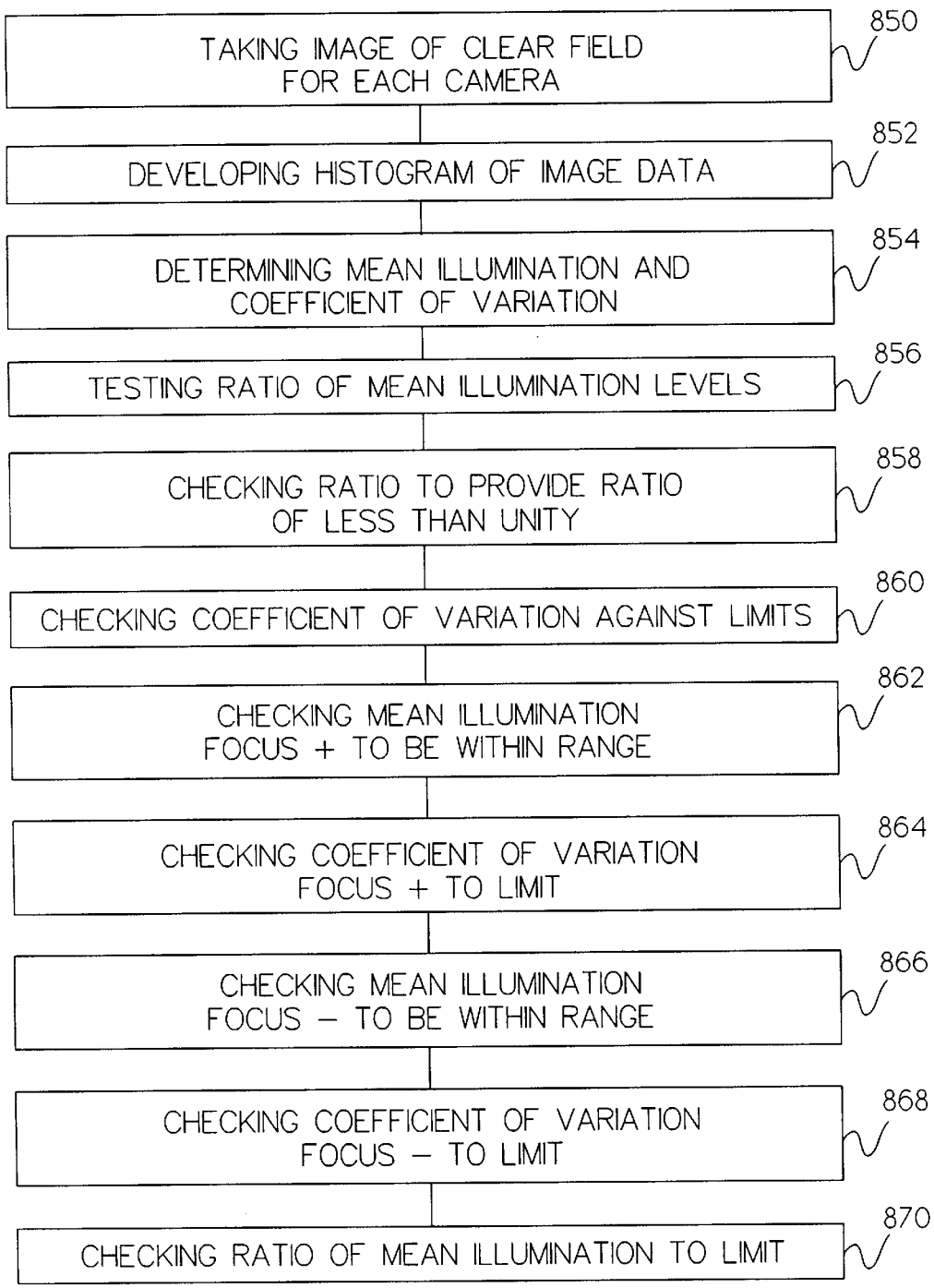
FIG. 21 shows a flow diagram of one method of the invention for checking focus system illumination quality.

Refer now to FIG. 21 which shows a flow diagram of the method of the invention for checking focus system illumination quality. Proper illumination at the focus cameras is needed for accurate focus of an automated biological specimen analysis system. An above and below autofocus method often determines the signal strength for each camera used in such a system and attempts to balance those signals. Such methods use at least two focus cameras. If the illumination level is different at each camera, there may be a discrepancy in signal strength even though the locus of the image presented to each camera may be identical. The invention provides a focus illumination test to be performed on each focus camera to check the illumination quality. The focus illumination test helps ensure that a signal presented to each camera is not influenced by any defect in illumination. At step 850, an image is taken of a clear field for each camera and, at step 852, a histogram is developed similar to that shown in Table 1. This histogram provides intensity values of the entire field for a focus and camera. From the histogram the mean illumination and coefficient of variation of the intensity of the field is determined for each camera at step 854.

TABLE 14

Intensity Histogram of Entire Field For Focus + Camera

| Int | # | Int | # | Int | # | Int | # | Int | # | Int | # | Int | # | Int | # |
|---|---|---|---|---|---|---|---|---|---|---|---|---|---|---|---|
| 0: | 0 | 32: | 0 | 64: | 0 | 96: | 0 | 128: | 0 | 160: | 0 | 192: | 0 | 224: | 2 |
| 1: | 0 | 33: | 0 | 65: | 0 | 97: | 0 | 129: | 0 | 161: | 0 | 193: | 0 | 225: | 7 |
| 2: | 0 | 34: | 0 | 66: | 0 | 98: | 0 | 130: | 0 | 162: | 0 | 194: | 0 | 226: | 213 |
| 3: | 0 | 35: | 0 | 67: | 0 | 99: | 0 | 131: | 0 | 163: | 0 | 195: | 0 | 227: | 1424 |
| 4: | 0 | 36: | 0 | 68: | 0 | 100: | 0 | 132: | 0 | 164: | 0 | 196: | 0 | 228: | 7803 |
| 5: | 0 | 37: | 0 | 69: | 0 | 101: | 0 | 133: | 0 | 165: | 0 | 197: | 0 | 229: | 47942 |
| 6: | 0 | 38: | 0 | 70: | 0 | 102: | 0 | 134: | 0 | 166: | 0 | 198: | 0 | 230: | 60366 |
| 7: | 0 | 39: | 0 | 71: | 0 | 103: | 0 | 135: | 0 | 167: | 0 | 199: | 0 | 231: | 74350 |
| 8: | 0 | 40: | 0 | 72: | 0 | 104: | 0 | 136: | 0 | 168: | 0 | 200: | 0 | 232: | 51837 |
| 9: | 0 | 41: | 0 | 73: | 0 | 105: | 0 | 137: | 0 | 169: | 0 | 201: | 0 | 233: | 15630 |
| 10: | 0 | 42: | 0 | 74: | 0 | 106: | 0 | 138: | 0 | 170: | 0 | 202: | 0 | 234: | 2231 |
| 11: | 0 | 43: | 0 | 75: | 0 | 107: | 0 | 139: | 0 | 171: | 0 | 203: | 0 | 235: | 317 |
| 12: | 0 | 44: | 0 | 76: | 0 | 108: | 0 | 140: | 0 | 172: | 0 | 204: | 0 | 236: | 22 |
| 13: | 0 | 45: | 0 | 77: | 0 | 109: | 0 | 141: | 0 | 173: | 0 | 205: | 0 | 237: | 0 |
| 14: | 0 | 46: | 0 | 78: | 0 | 110: | 0 | 142: | 0 | 174: | 0 | 206: | 0 | 238: | 0 |
| 15: | 0 | 47: | 0 | 79: | 0 | 111: | 0 | 143: | 0 | 175: | 0 | 207: | 0 | 239: | 0 |
| 16: | 0 | 48: | 0 | 80: | 0 | 112: | 0 | 144: | 0 | 176: | 0 | 208: | 0 | 240: | 0 |
| 17: | 0 | 49: | 0 | 81: | 0 | 113: | 0 | 145: | 0 | 177: | 0 | 209: | 0 | 241: | 0 |
| 18: | 0 | 50: | 0 | 82: | 0 | 114: | 0 | 146: | 0 | 178: | 0 | 210: | 0 | 242: | 0 |
| 19: | 0 | 51: | 0 | 83: | 0 | 115: | 0 | 147: | 0 | 179: | 0 | 211: | 0 | 243: | 0 |
| 20: | 0 | 52: | 0 | 84: | 0 | 116: | 0 | 148: | 0 | 180: | 0 | 212: | 0 | 244: | 0 |
| 21: | 0 | 53: | 0 | 85: | 0 | 117: | 0 | 149: | 0 | 181: | 0 | 213: | 0 | 245: | 0 |
| 22: | 0 | 54: | 0 | 86: | 0 | 118: | 0 | 150: | 0 | 182: | 0 | 214: | 0 | 246: | 0 |
| 23: | 0 | 55: | 0 | 87: | 0 | 119: | 0 | 151: | 0 | 183: | 0 | 215: | 0 | 247: | 0 |
| 24: | 0 | 56: | 0 | 88: | 0 | 120: | 0 | 152: | 0 | 184: | 0 | 216: | 0 | 248: | 0 |
| 25: | 0 | 57: | 0 | 89: | 0 | 121: | 0 | 153: | 0 | 185: | 0 | 217: | 0 | 249: | 0 |
| 26: | 0 | 58: | 0 | 90: | 0 | 122: | 0 | 154: | 0 | 186: | 0 | 218: | 0 | 250: | 0 |
| 27: | 0 | 59: | 0 | 91: | 0 | 123: | 0 | 155: | 0 | 187: | 0 | 219: | 0 | 251: | 0 |
| 28: | 0 | 60: | 0 | 92: | 0 | 124: | 0 | 156: | 0 | 188: | 0 | 220: | 0 | 252: | 0 |
| 29: | 0 | 61: | 0 | 93: | 0 | 125: | 0 | 157: | 0 | 189: | 0 | 221: | 0 | 253: | 0 |
| 30: | 0 | 62: | 0 | 94: | 0 | 126: | 0 | 158: | 0 | 190: | 0 | 222: | 0 | 254: | 0 |
| 31: | 0 | 63: | 0 | 95: | 0 | 127: | 0 | 159: | 0 | 191: | 0 | 223: | 0 | 255: | 0 |

TABLE 15

Intensity Histogram of Entire Field For Focus (−) Camera

| Int | # | Int | # | Int | # | Int | # | Int | # | Int | # | Int | # | Int | # |
|---|---|---|---|---|---|---|---|---|---|---|---|---|---|---|---|
| 0: | 0 | 32: | 0 | 64: | 0 | 96: | 0 | 128: | 0 | 160: | 0 | 192: | 0 | 224: | 0 |
| 1: | 0 | 33: | 0 | 65: | 0 | 97: | 0 | 129: | 0 | 161: | 0 | 193: | 0 | 225: | 0 |
| 2: | 0 | 34: | 0 | 66: | 0 | 98: | 0 | 130: | 0 | 162: | 0 | 194: | 0 | 226: | 0 |
| 3: | 0 | 35: | 0 | 67: | 0 | 99: | 0 | 131: | 0 | 163: | 0 | 195: | 0 | 227: | 0 |
| 4: | 0 | 36: | 0 | 68: | 0 | 100: | 0 | 132: | 0 | 164: | 0 | 196: | 0 | 228: | 1 |
| 5: | 0 | 37: | 0 | 69: | 0 | 101: | 0 | 133: | 0 | 165: | 0 | 197: | 0 | 229: | 0 |
| 6: | 0 | 38: | 0 | 70: | 0 | 102: | 0 | 134: | 0 | 166: | 0 | 198: | 0 | 230: | 214 |
| 7: | 0 | 39: | 0 | 71: | 0 | 103: | 0 | 135: | 0 | 167: | 0 | 199: | 0 | 231: | 404 |
| 8: | 0 | 40: | 0 | 72: | 0 | 104: | 0 | 136: | 0 | 168: | 0 | 200: | 0 | 232: | 6823 |
| 9: | 0 | 41: | 0 | 73: | 0 | 105: | 0 | 137: | 0 | 169: | 0 | 201: | 0 | 233: | 8942 |
| 10: | 0 | 42: | 0 | 74: | 0 | 106: | 0 | 138: | 0 | 170: | 0 | 202: | 0 | 234: | 62366 |
| 11: | 0 | 43: | 0 | 75: | 0 | 107: | 0 | 139: | 0 | 171: | 0 | 203: | 0 | 235: | 62350 |

TABLE 15-continued

Intensity Histogram of Entire Field For Focus (–) Camera

| Int | # | Int | # | Int | # | Int | # | Int | # | Int | # | Int | # |
|---|---|---|---|---|---|---|---|---|---|---|---|---|---|
| 12: | 0 | 44: | 0 | 76: | 0 | 108: | 0 | 140: | 0 | 172: | 0 | 204: | 0 | 236: | 61837 |
| 13: | 0 | 45: | 0 | 77: | 0 | 109: | 0 | 141: | 0 | 173: | 0 | 205: | 0 | 237: | 16630 |
| 14: | 0 | 46: | 0 | 78: | 0 | 110: | 0 | 142: | 0 | 174: | 0 | 206: | 0 | 238: | 1231 |
| 15: | 0 | 47: | 0 | 79: | 0 | 111: | 0 | 143: | 0 | 175: | 0 | 207: | 0 | 239: | 217 |
| 16: | 0 | 48: | 0 | 80: | 0 | 112: | 0 | 144: | 0 | 176: | 0 | 208: | 0 | 240: | 122 |
| 17: | 0 | 49: | 0 | 81: | 0 | 113: | 0 | 145: | 0 | 177: | 0 | 209: | 0 | 241: | 0 |
| 18: | 0 | 50: | 0 | 82: | 0 | 114: | 0 | 146: | 0 | 178: | 0 | 210: | 0 | 242: | 0 |
| 19: | 0 | 51: | 0 | 83: | 0 | 115: | 0 | 147: | 0 | 179: | 0 | 211: | 0 | 243: | 0 |
| 20: | 0 | 52: | 0 | 84: | 0 | 116: | 0 | 148: | 0 | 180: | 0 | 212: | 0 | 244: | 0 |
| 21: | 0 | 53: | 0 | 85: | 0 | 117: | 0 | 149: | 0 | 181: | 0 | 213: | 0 | 245: | 0 |
| 22: | 0 | 54: | 0 | 86: | 0 | 118: | 0 | 150: | 0 | 182: | 0 | 214: | 0 | 246: | 0 |
| 23: | 0 | 55: | 0 | 87: | 0 | 119: | 0 | 151: | 0 | 183: | 0 | 215: | 0 | 247: | 0 |
| 24: | 0 | 56: | 0 | 88: | 0 | 120: | 0 | 152: | 0 | 184: | 0 | 216: | 0 | 248: | 0 |
| 25: | 0 | 57: | 0 | 89: | 0 | 121: | 0 | 153: | 0 | 185: | 0 | 217: | 0 | 249: | 0 |
| 26: | 0 | 58: | 0 | 90: | 0 | 122: | 0 | 154: | 0 | 186: | 0 | 218: | 0 | 250: | 0 |
| 27: | 0 | 59: | 0 | 91: | 0 | 123: | 0 | 155: | 0 | 187: | 0 | 219: | 0 | 251: | 0 |
| 28: | 0 | 60: | 0 | 92: | 0 | 124: | 0 | 156: | 0 | 188: | 0 | 220: | 0 | 252: | 0 |
| 29: | 0 | 61: | 0 | 93: | 0 | 125: | 0 | 157: | 0 | 189: | 0 | 221: | 0 | 253: | 0 |
| 30: | 0 | 62: | 0 | 94: | 0 | 126: | 0 | 158: | 0 | 190: | 0 | 222: | 0 | 254: | 0 |
| 31: | 0 | 63: | 0 | 95: | 0 | 127: | 0 | 159: | 0 | 191: | 0 | 223: | 0 | 255: | 0 |

The ratio of mean illumination levels is tested along with the absolute value of the means at step 856. The ratio is checked and inverted if necessary to provide a ratio of less than unity at step 858. This allows for one limit to be set for the ratio. The coefficient of variation for each camera is also checked against limits at step 860. Limits are seen below in Table 16.

At step 862, the mean illumination focus+ is checked to be within a certain tolerance range. At step 864, the coefficient of variation of the focus+ camera is checked against a predetermined limit. At step 866, the mean illumination of the focus plus camera is checked to be within a predetermined range of values. At step 868 the coefficient of variation of the focus+camera is checked against a predetermined limit. Similarly, at step 870, the ratio of beam illumination is checked against a predetermined limit.

TABLE 16

Parameter Results and Limits Comparison for Static Field Uniformity

| Parameter Description | Actual Value | Limits |
|---|---|---|
| Mean Illumination Focus (+) | 231 | 220 < x < 250 |
| Coefficient of variation Focus (+) | 0.6% | <1.0% |
| Mean Illumination Focus (–) | 235 | 220 < x < 250 |
| Coefficient of variation Focus (–) | 0.7% | <1.0% |
| Ratio of Mean Illumination | 0.98 | >0.97 |

Focus Noise Floor Level

Figure 22:
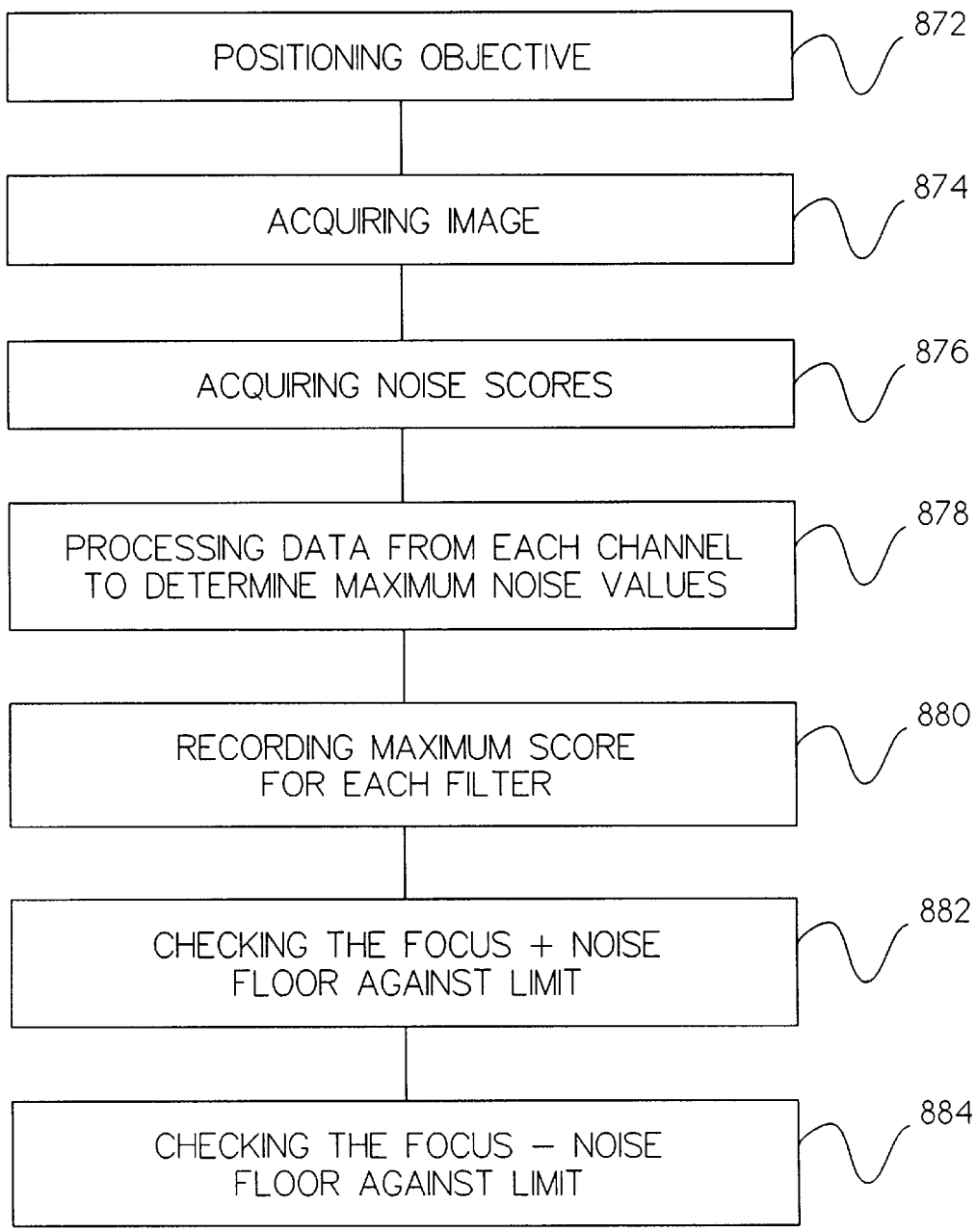
FIG. 22 shows a flow diagram of one method of the invention for checking focus noise floor level.

Now referring to FIG. 22, a flow diagram of the invention for checking focus noise floor level is shown. The above and below focus method being tested in accordance with the invention uses focus filters for each camera as shown in FIG. 15. The focus filters are electronic filters which optimize signals delivered from the cameras for focus processing by filtering out objects that do not have the characteristic frequency content of cellular nuclei. Filtering techniques are described in more detail below. Debris in the focus paths and electronic noise may generate erroneous focus projections. Theoretically, the response of the focus filters should be zero over a uniformly illuminated clear field of view. In actuality, however, the response of the filters to this type of stimulus is rarely, if ever, zero. Electronic noise, debris in the focus path, and focus filter inefficiencies can and do result in some response at the output. This response is referred to as the "focus noise floor level." Specifically, the focus noise floor level is the response of the focus filters to a uniformly illuminated clear field. One aspect of the invention provides a test for measuring the amplitude of filter response under this condition. In addition, since the above and below focus method employed generates a focus filter data point for each active line in the video timing, in one example, a total of 512 focus noise floor levels are captured and analyzed for the focus plus and focus minus response. A focus noise floor test is performed on each focus camera to ensure proper operation. In one specific embodiment, this test is performed at a system level. It is advantageous to perform the focus noise floor level test after pixel calibration at a selected magnification has been completed.

At step 872, a selected objective is positioned over the nominal clear area of the calibration plate with, for example, a 20×magnification selected. An image is acquired at step 874 and at step 876 noise scores for each line of the plus and minus focus filters are acquired. Data acquired from each channel is processed to determine the maximum noise values for each channel at step 878. The maximum score for each filter is then recorded as the focus noise floor at step 880. At step 882 the focus plus noise floor is checked against a predetermined limit. The focus minus noise floor is also checked at step 884. Examples of focus noise floor limits are shown below.

Limits

Focus+noise floor: <10 counts
Focus–noise floor: <10 counts

Focus Filter Frequency Response

Figure 23:
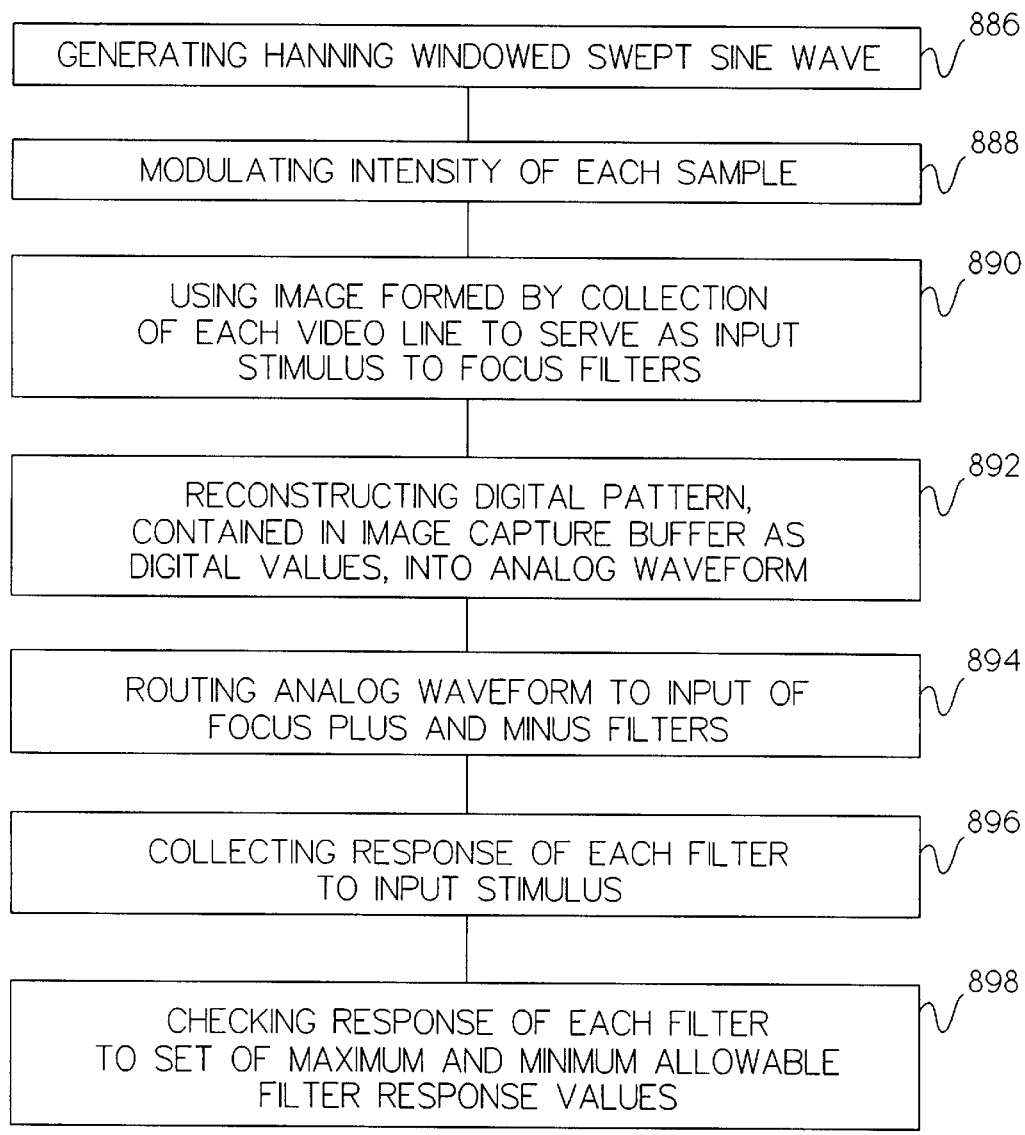
FIG. 23 shows a flow diagram of one method of the invention for checking focus filter frequency response.

Now referring to FIG. 23, a schematic flow diagram of one method for checking focus filter frequency response is shown. The electronic band-pass filters discussed below, utilized by the focus channels are optimized for maximum sensitivity in the frequency range characteristic to that of cellular nuclei. To determine the focus projection of "best clinical value" these filters must perform appropriately in both the stop and pass bands. The bandpass is chosen to heavily weigh frequencies which are generated by cellular nuclei when imaged at a defocus of about four microns. Four microns is, in one embodiment, the nominal separation of the focus and primary cameras. Poorly adjusted, or malfunctioning focus filters may severely skew the focus projection value. It is necessary, therefore, to accurately quantify the performance of the filters to ensure proper operation of the focus subsystem. The focus filter frequency response test of the invention provides the means for evaluating filter efficacy by evaluating its output response to that of a known test pattern. It is advantageous to perform this test prior to running a batch of slides for analysis.

At step 886, a Hanning windowed swept sine wave is electronically generated from 50 kHz to 2.2 MHz. in the ICF image buffer according to the expression:

$$I(X_i) = G[(1+\sin(2\pi TX_i * f + \phi)) * \{1 + G_h(\sin(\pi X_i/(NoPixels-1)))\}] + 0.5$$

Where:

$I(X_i)$=The intensity or amplitude of the ith pixel.

$X_i$=The horizontal position index of the ith pixel or sample. From 0 through 511 samples.

$\Phi$=The phase term for each sample. Typically 0 radians.

G=Intensity gain factor.

$G_h$=Hanning gain factor.

NoPixels=Total number of pixels or samples.

f=The frequency of the test pattern for the current line.

At step 888 it is indicated that the intensity of each sample, I(xi) is modulated according to the expression given above. At step 890, the image formed by the collection of each video line then serves as the input stimulus to the focus filters. This pattern, contained in the image capture buffer (ICF) 516 as digital values, is then reconstructed into an analog waveform by routing it through an on board D/A converter at step 892. The analog waveform is then routed to the input of the focus plus and minus filters providing them necessary stimulus for characterizing the overall output response at step 894. The filter response for each line is then collected at step 896. The response is then checked against limits in step 898.

Figure 24:
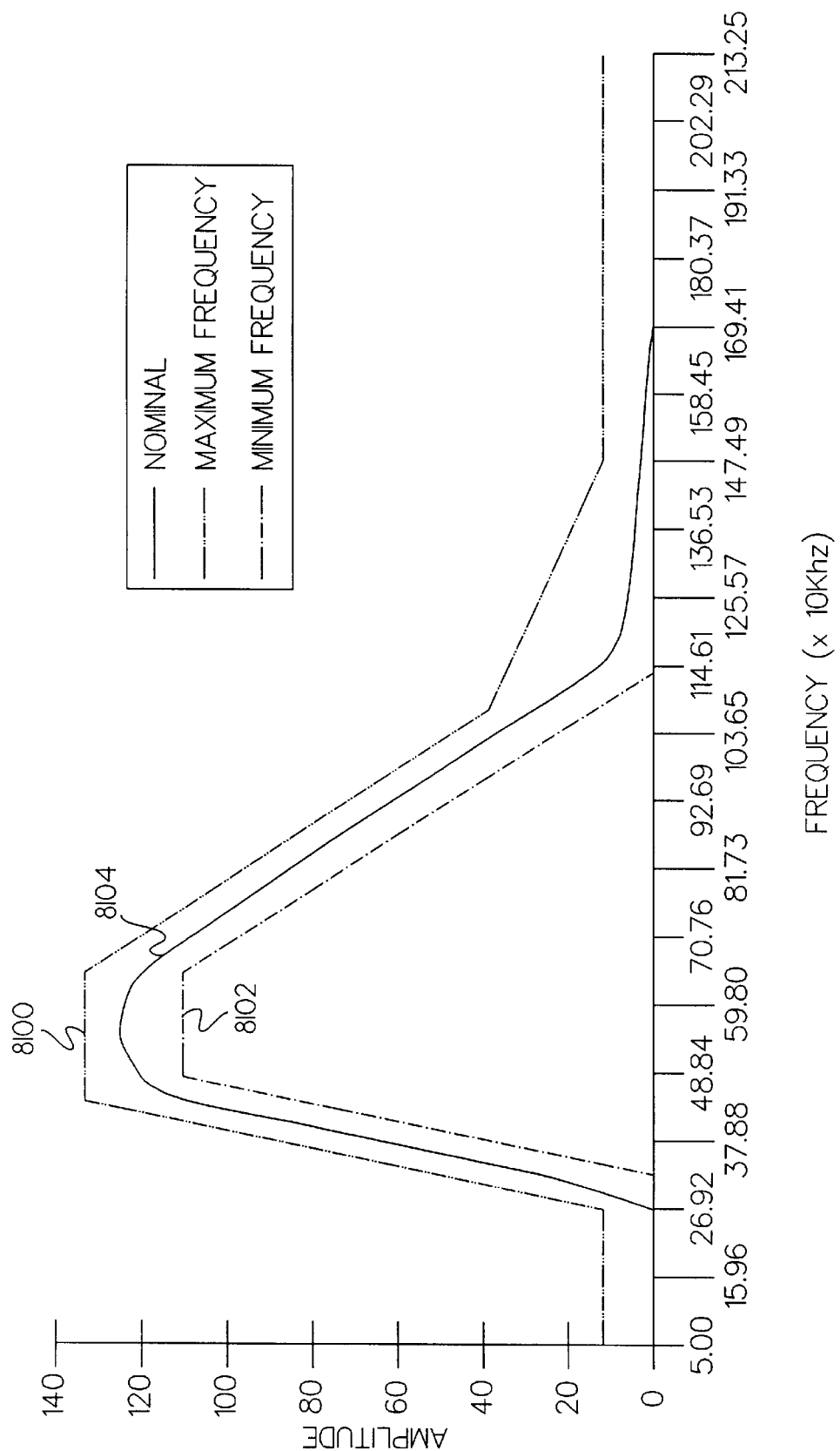
FIG. 24 shows a graph of focus filter response.

Response limits have been empirically determined for a machine manufactured by NeoPath, Inc. of Bellevue, Wash., U.S.A. called the AP300 System. The empirically derived limits represent the maximum and minimum allowable output variation for the filters. To ensure proper operation of the Focus System, the AP300 machine evaluates the response of the focus filters when initially processing of each new tray of slides. FIG. 24 illustrates the filter response envelope, the upper and lower curves, 8100 and 8102 respectively, represent the maximum and minimum limits. The middle curve 8104 represents a typical response for a normally functioning filter. Table 17, contains an example of limits used for evaluating filter response. Bin 0, corresponds to the starting frequency of the test pattern (50 Khz). Bin 255 corresponds to the ending frequency of the test pattern (2.2 Mhz).

TABLE 17

Maximum and Minimum Allowable Focus Response Values for Hanning Swept Sine Wave Test Pattern

| Bin | Min | Max | Bin | Min | Max | Bin | Min | Max | Bin | Min | Max |
|---|---|---|---|---|---|---|---|---|---|---|---|
| 0 | 0 | 12 | 64 | 110 | 133 | 128 | 0 | 34 | 192 | 0 | 13 |
| 1 | 0 | 12 | 65 | 110 | 133 | 129 | 0 | 34 | 193 | 0 | 13 |
| 2 | 0 | 12 | 66 | 110 | 133 | 130 | 0 | 33 | 194 | 0 | 13 |
| 3 | 0 | 12 | 67 | 110 | 133 | 131 | 0 | 33 | 195 | 0 | 13 |
| 4 | 0 | 12 | 68 | 110 | 133 | 132 | 0 | 32 | 196 | 0 | 13 |
| 5 | 0 | 12 | 69 | 110 | 133 | 133 | 0 | 32 | 197 | 0 | 13 |
| 6 | 0 | 12 | 70 | 110 | 133 | 134 | 0 | 31 | 198 | 0 | 13 |
| 7 | 0 | 12 | 71 | 110 | 133 | 135 | 0 | 31 | 199 | 0 | 13 |
| 8 | 0 | 12 | 72 | 110 | 133 | 136 | 0 | 30 | 200 | 0 | 13 |
| 9 | 0 | 12 | 73 | 108 | 131 | 137 | 0 | 30 | 201 | 0 | 13 |
| 10 | 0 | 12 | 74 | 106 | 129 | 138 | 0 | 29 | 202 | 0 | 13 |
| 11 | 0 | 12 | 75 | 104 | 127 | 139 | 0 | 29 | 203 | 0 | 13 |
| 12 | 0 | 12 | 76 | 102 | 125 | 140 | 0 | 28 | 204 | 0 | 13 |
| 13 | 0 | 12 | 77 | 100 | 123 | 141 | 0 | 28 | 205 | 0 | 13 |
| 14 | 0 | 12 | 78 | 98 | 121 | 142 | 0 | 27 | 206 | 0 | 13 |
| 15 | 0 | 12 | 79 | 96 | 119 | 143 | 0 | 27 | 207 | 0 | 13 |
| 16 | 0 | 12 | 80 | 94 | 117 | 144 | 0 | 26 | 208 | 0 | 13 |
| 17 | 0 | 12 | 81 | 92 | 115 | 145 | 0 | 25 | 209 | 0 | 13 |
| 18 | 0 | 12 | 82 | 90 | 113 | 146 | 0 | 25 | 210 | 0 | 13 |
| 19 | 0 | 12 | 83 | 88 | 111 | 147 | 0 | 24 | 211 | 0 | 13 |
| 20 | 0 | 12 | 84 | 86 | 109 | 148 | 0 | 24 | 212 | 0 | 13 |
| 21 | 0 | 12 | 85 | 84 | 107 | 149 | 0 | 23 | 213 | 0 | 13 |
| 22 | 0 | 12 | 86 | 82 | 105 | 150 | 0 | 23 | 214 | 0 | 13 |
| 23 | 0 | 12 | 87 | 80 | 103 | 151 | 0 | 22 | 215 | 0 | 13 |
| 24 | 0 | 12 | 88 | 78 | 101 | 152 | 0 | 22 | 216 | 0 | 13 |
| 25 | 0 | 12 | 89 | 76 | 99 | 153 | 0 | 21 | 217 | 0 | 13 |
| 26 | 0 | 12 | 90 | 74 | 97 | 154 | 0 | 21 | 218 | 0 | 13 |
| 27 | 0 | 18 | 91 | 72 | 95 | 155 | 0 | 20 | 219 | 0 | 13 |
| 28 | 0 | 23 | 92 | 70 | 93 | 156 | 0 | 20 | 220 | 0 | 13 |
| 29 | 0 | 29 | 93 | 68 | 91 | 157 | 0 | 19 | 221 | 0 | 13 |
| 30 | 0 | 34 | 94 | 66 | 89 | 158 | 0 | 19 | 222 | 0 | 13 |
| 31 | 0 | 40 | 95 | 64 | 87 | 159 | 0 | 18 | 223 | 0 | 13 |
| 32 | 0 | 45 | 96 | 62 | 85 | 160 | 0 | 18 | 224 | 0 | 13 |
| 33 | 0 | 51 | 97 | 60 | 83 | 161 | 0 | 17 | 225 | 0 | 13 |
| 34 | 0 | 56 | 98 | 58 | 81 | 162 | 0 | 17 | 226 | 0 | 13 |
| 35 | 0 | 62 | 99 | 56 | 79 | 163 | 0 | 16 | 227 | 0 | 13 |
| 36 | 0 | 67 | 100 | 54 | 77 | 164 | 0 | 16 | 228 | 0 | 13 |
| 37 | 0 | 73 | 101 | 52 | 75 | 165 | 0 | 15 | 229 | 0 | 13 |
| 38 | 0 | 78 | 102 | 50 | 73 | 166 | 0 | 15 | 230 | 0 | 13 |

TABLE 17-continued

Maximum and Minimum Allowable Focus Response Values for
Hanning Swept Sine Wave Test Pattern

| Bin | Min | Max | Bin | Min | Max | Bin | Min | Max | Bin | Min | Max |
|-----|-----|-----|-----|-----|-----|-----|-----|-----|-----|-----|-----|
| 39 | 0 | 84 | 103 | 48 | 71 | 167 | 0 | 14 | 231 | 0 | 13 |
| 40 | 43 | 89 | 104 | 46 | 69 | 168 | 0 | 14 | 232 | 0 | 13 |
| 41 | 49 | 95 | 105 | 44 | 67 | 169 | 0 | 13 | 233 | 0 | 13 |
| 42 | 55 | 100 | 106 | 42 | 65 | 170 | 0 | 13 | 234 | 0 | 13 |
| 43 | 61 | 106 | 107 | 40 | 63 | 171 | 0 | 13 | 235 | 0 | 13 |
| 44 | 67 | 111 | 108 | 38 | 61 | 172 | 0 | 13 | 236 | 0 | 13 |
| 45 | 73 | 117 | 109 | 36 | 59 | 173 | 0 | 13 | 237 | 0 | 13 |
| 46 | 79 | 122 | 110 | 34 | 57 | 174 | 0 | 13 | 238 | 0 | 13 |
| 47 | 86 | 128 | 111 | 32 | 55 | 175 | 0 | 13 | 239 | 0 | 13 |
| 48 | 92 | 133 | 112 | 30 | 53 | 176 | 0 | 13 | 240 | 0 | 13 |
| 49 | 98 | 133 | 113 | 28 | 51 | 177 | 0 | 13 | 241 | 0 | 13 |
| 50 | 104 | 133 | 114 | 26 | 49 | 178 | 0 | 13 | 242 | 0 | 13 |
| 51 | 109 | 133 | 115 | 24 | 47 | 179 | 0 | 13 | 243 | 0 | 13 |
| 52 | 110 | 133 | 116 | 22 | 45 | 180 | 0 | 13 | 244 | 0 | 13 |
| 53 | 110 | 133 | 117 | 20 | 43 | 181 | 0 | 13 | 245 | 0 | 13 |
| 54 | 110 | 133 | 118 | 18 | 41 | 182 | 0 | 13 | 246 | 0 | 13 |
| 55 | 110 | 133 | 119 | 16 | 39 | 183 | 0 | 13 | 247 | 0 | 13 |
| 56 | 110 | 133 | 120 | 14 | 38 | 184 | 0 | 13 | 248 | 0 | 13 |
| 57 | 110 | 133 | 121 | 12 | 38 | 185 | 0 | 13 | 249 | 0 | 13 |
| 58 | 110 | 133 | 122 | 10 | 37 | 186 | 0 | 13 | 250 | 0 | 13 |
| 59 | 110 | 133 | 123 | 8 | 37 | 187 | 0 | 13 | 251 | 0 | 13 |
| 60 | 110 | 133 | 124 | 6 | 36 | 188 | 0 | 13 | 252 | 0 | 13 |
| 61 | 110 | 133 | 125 | 4 | 36 | 189 | 0 | 13 | 253 | 0 | 13 |
| 62 | 110 | 133 | 126 | 2 | 35 | 190 | 0 | 13 | 254 | 0 | 13 |
| 63 | 110 | 133 | 127 | 0 | 35 | 191 | 0 | 13 | 255 | 0 | 13 |

If the focus filter frequency response test fails, either in pass or stop bands, the failure is logged and system integrity checks are advantageously rerun. Pass bands and stop bands are specific frequencies which depend upon the system being tested. Focus filter response may comprise a non calibratable subsystem and as such may not be adjusted by the system. In one example, a system level integrity test will attempt to measure the systems response a maximum of 5 times. If the filter response does not pass during these attempts the system is halted.

Focus Camera Frequency Response

Figure 25:
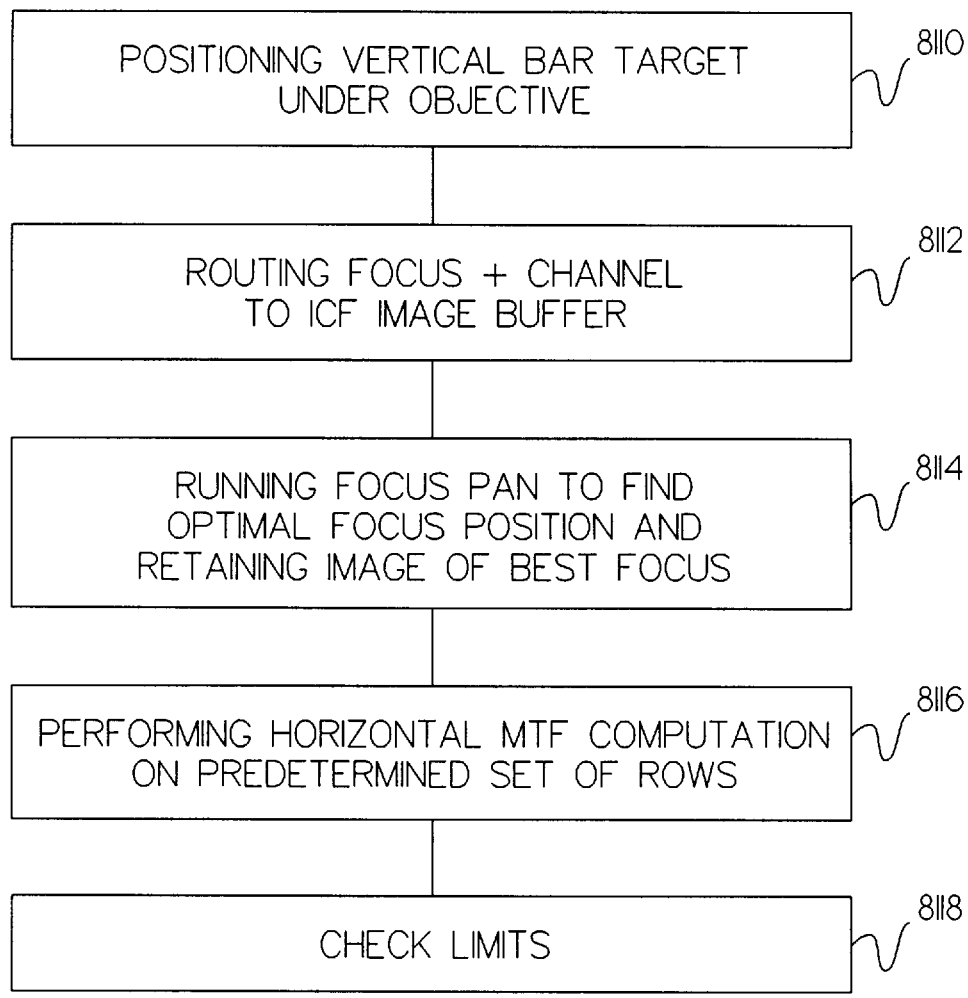
FIG. 25 shows a flow diagram of one method of the invention for checking focus camera frequency response.

Now referring to FIG. 25, a flow diagram of one example of the invention for checking focus camera frequency response is shown. The focus system relies on several components. In this example, the optics deliver images to the focus cameras at a specified spacing, cameras convert the image into an electronic signal, and the ICF converts the electronic signal into an estimate of the focus of the image projected to the primary camera in the camera head assembly. This test measures a focus camera's ability to represent contrast and fine image detail in its electronic signal.

Modulation transfer function test is substantially similar to the tests measuring MTF in a collection quality test. The ability of the focus cameras to represent the image accurately with their electronic signal is important to a properly operating focus system and must be checked periodically to insure acceptable operation.

This test may be used to insure operation for a focus camera components in a focus system such as the one described in "Method and Apparatus for Rapid Capture of Focused Microscopic Images", by Jon Hayenga, et. al. discussed further hereinbelow.

Like the primary focus filters, the focus camera frequency response is critical to projecting the focus of best clinical value. An MTF test is conducted for each focus camera to ensure proper operation.

At step 8110 the 50 lp/mm vertical bar target is positioned under the objective. In one example, the vertical bar target may be a bar target of 50 lp/mm. At step 8112, the focus+ channel is routed to the ICF image buffer. At step 8114, an MTF focus pan is performed to find the optimal focus position and the image of best focus is retained. At step 8116, a horizontal MTF computation is performed on 32 rows at the center of the image to measure the response of the focus− camera. The same procedure is repeated for the focus− camera.

Given the manufacturer's specification for the camera and our optical system transfer function, Tables 18 and 19 list the focus+ and focus− camera frequency response limits. Measurements that yield lower results than these limits 8118 indicate a malfunctioning or substandard camera or optical path.

TABLE 18

Focus + Camera Frequency Response

| Frequency Limits | | Minimum MTF |
|---|---|---|
| Minimum | Maximum | Center |
| 0.0 | 0.0 | 0.45 |
| 47.5 | 52.5 | 0.84 |
| 142.5 | 157.5 | 0.73 |
| 237.5 | 262.5 | 0.54 |
| 332.5 | 367.5 | 0.41 |

TABLE 19

Focus − Camera Frequency Response

| Frequency Limits | | Minimum MTF |
|---|---|---|
| Minimum | Maximum | Center |
| 0.0 | 0.0 | 0.45 |
| 47.5 | 52.5 | 0.84 |

TABLE 19-continued

Focus – Camera Frequency Response

| Frequency Limits | | Minimum MTF |
|---|---|---|
| Minimum | Maximum | Center |
| 142.5 | 157.5 | 0.73 |
| 237.5 | 262.5 | 0.54 |
| 332.5 | 367.5 | 0.41 |

Focus Camera Longitudinal Separation Test

Figure 26:
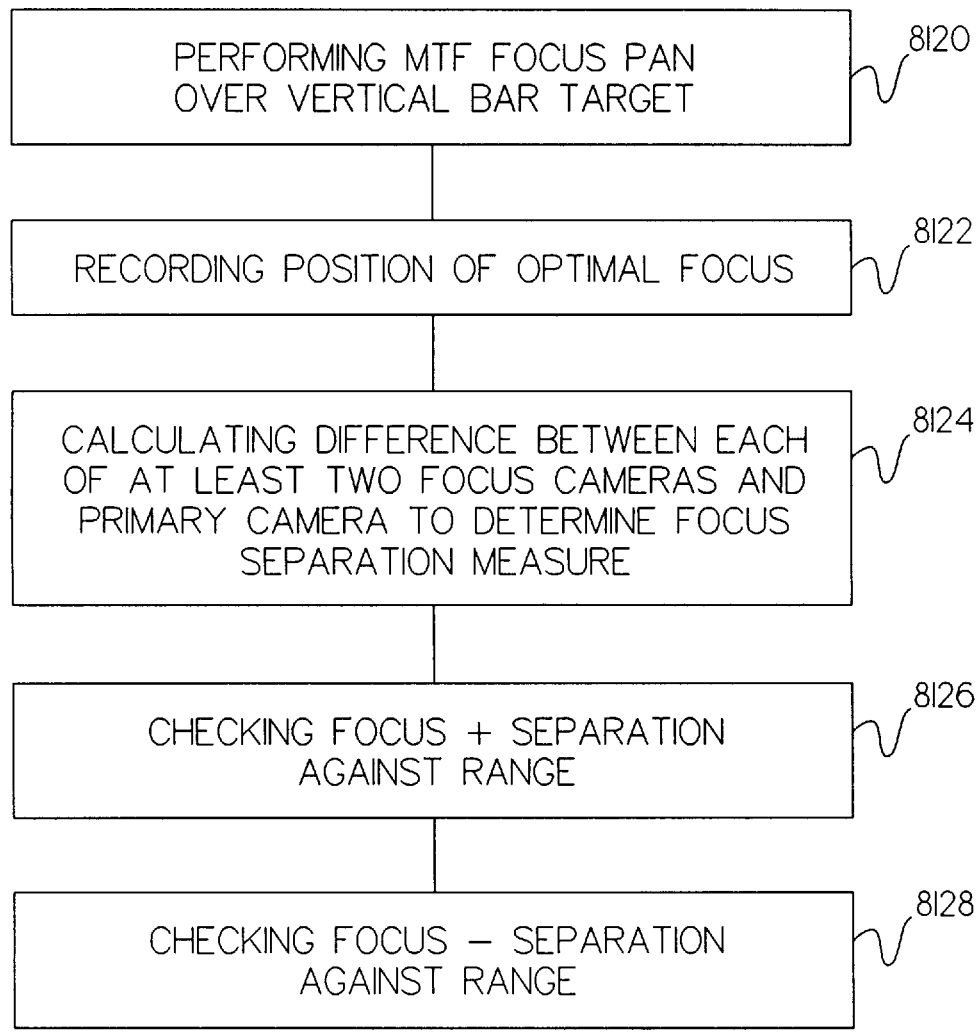
FIG. 26 shows a flow diagram of one example of the method of the invention for performing a focus camera longitudinal separation test.

Referring now to FIG. 26, a flow diagram for one example of a focus camera longitudinal separation test is shown. In a focus system described in Hayenga, et. al., focus cameras are spaced above and below the optimal image plane of the objective. The z-separation between the focus and primary cameras directly affects the focus projection. The z-separation as used refers to the separation of focus positions between the focus camera as along the optical axis. The focus camera longitudinal position test is conducted to ensure that the camera separations are within limits.

An step 8120, an MTF focus pan is performed over the 50 lp/mm vertical bar target for the primary camera and each focus camera. The position of optimal focus is recorded at step 8122 and the difference between the focus cameras and primary camera is taken to determine the focus separation at step 8124. Because of the extremely small dimensions being measured at 20x, for example, the measurement is performed at lower magnification where the effective separation of the focal planes is much larger. This serves two purposes, first the positioning and step size errors at 20x may be a significant percentage of the measurement. Second, the depth of field of the objective at 20x makes any tilt of target a significant contributor to the uncertainty of the estimate of the optimal focus position. Using a lower magnification lens makes both the separation and tilt factors much less significant in the measurement allowing an effective improvement in the separation measurement. The Z-separation at a lower magnification is increased by the ratio of the square of the relative magnifications. At steps 8126 and 8128 the focus+ separation and focus– separation are checked respectively. One example of tolerance ranges for focus separation is shown below.

Limits

Focus+ separation: 3500<x<4500 nm

Focus– separation: –7000<x<–6000 nm

Failing the focus separation test preferably invalidates the results of a previously processed tray of slides.

Focus Camera Lateral Separation Test

Figure 27:
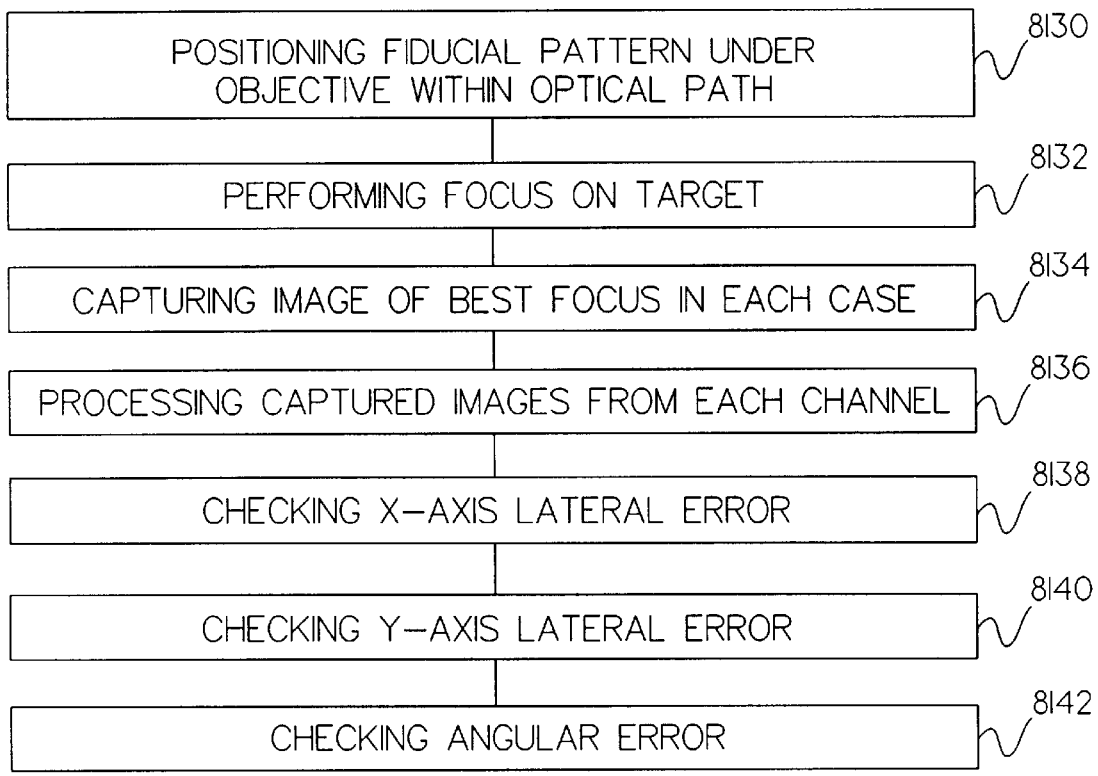
FIG. 27 shows a flow diagram showing one example of the method of the invention for checking focus camera lateral separation.

Now referring to FIG. 27, one example of a focus camera lateral separation test is shown in flow diagram form. A focus projection score, computed as described in further detail below may be derived, in part, by balancing the frequency content, of the focus plus and focus minus cameras. It is desirable, therefore, to image the same field position at both focus channels. Lateral misalignment in x or y between channels may result in a different presentation of the field to each camera. Cellular data imaged in one channel may not be imaged at all in the other channel. Mispositioning will potentially cause an imbalance in the overall frequency content of the images presented to each focus camera. A signal imbalance may ultimately skew the focus projection away from optimal focus. In addition, focus line scores, used in determining the focus projection value, are qualified in pairs before they are included into the computation for focus projection. A score from the plus focus camera is combined with a score generated by the corresponding line from the minus focus camera. This qualification technique assumes that the focus line pairs have been exposed to the same region in the image. Severe lateral displacement in y could result in focus score comparisons for different areas of the image. Rotational, or angular misalignment between the focus channels may also result in erroneous focus projection scores for the same reasons mentioned above. It is therefore necessary to adjust and periodically measure these parameters to help ensure proper focus system operation. The focus camera lateral separation test measures these parameters and may advantageously be run prior to processing each tray of slides.

At step 8130, a 0,0 fiducial pattern or primitive is positioned under a 20×objective. Alternately, the focus+ and focus– video channels may be routed to the ICF image buffer. A z-pan focus is performed under control of the FOV computers on the target at step 8132. A z-pan focus refers to a generic focusing procedure in which a sample is scanned in the Z axis, that is, along the optical axis, preferably through the focal plane of the optical system. At predetermined increments during the scan, images are acquired by a detector, and preferably imaged onto the focal plane of the system. A plurality of images are processed to determine a feature, or features, related to the focus of each individual image. The feature or combination of features may be, for example,the slope of edge profiles in the image, or, the spatial frequency content of the image, or some other suitable feature. Typically, a plot of the feature or features is generated and an optimal position is determined. The optimal position indicates the best focus position for the image.

For each z-pan, the image of best focus is captured and saved for later analysis at step 8134. The images captured from each channel are then processed to determine the extent of any lateral (that is, x and y offsets) or angular offsets between cameras at steps 8138, 8140 and 8142 respectively. The table immediately below shows examples of test limits for the focus camera lateral separation test.

X-axis lateral error: <±67 microns

Y-axis lateral error: <±67 microns

Angular error: <±0.01 radians

Failing the lateral separation test preferably invalidates the results of a previously processed tray of slides.

Closed Loop Fiducial Focus Test

Figure 28:
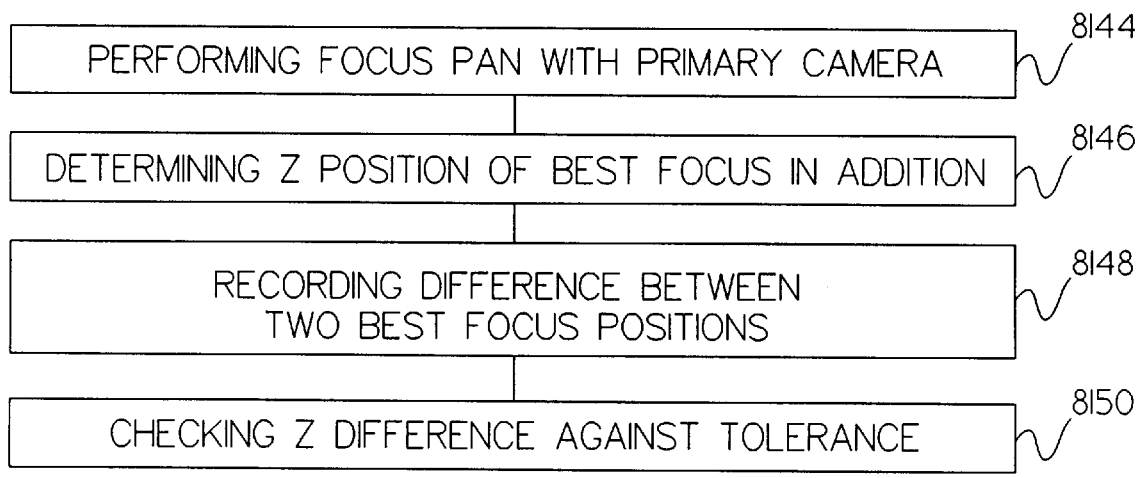
FIG. 28 shows a flow diagram of one example of a closed loop fiducial focus test in accordance with the rest of the invention.

Referring now to FIG. 28, a flow diagram of one example of a closed loop fiducial focus test is shown. The closed loop fiducial focus test verifies that the focus achieved by the above and below focus camera method is consistent with the focus achieved using a z-pan focus method. In this case the z-pan is performed using the primary camera in the preferred embodiment of this system. Although all the focus quality tests are important factors in developing an accurate focus projection, an overall closed loop test is required to ensure the system is operating correctly.

At step 8144, a z-pan focus is performed on the 0,0 fiducial using the primary camera. Simultaneously, as images are acquired on the primary camera the autofocus system of the instrument is also developing focus projections according to the alternate focussing method 8146 taught by Hayenga et al. The best focus for each of the two focusing techniques is determined. The difference in the two best focus positions is recorded at step 8148. At step 8150 a Z difference is checked against a predetermined tolerance as for example, Z difference: 1000<x<3000 nm.

The purpose of the autofocus system in the preferred embodiment is to provide a real time computation determining the location of best focus. The real time best focus location can be determined with a single flash of the lamp (i.e. real time), as the image of the field of interest is captured by the primary camera and two focus instruments simultaneously. However, the absolute position of best focus must be compared to a standard focus. The z-pan method provides a standard of comparison. Therefore, both methods of focus are compared on a test target. Although the tests outlined previously in this disclosure help to qualify the focus system. This test provides for a final redundant check to ensure the system is operating properly.

Failing may result in invalidating the results of the previously processed tray of slides.

In order to promote further understanding of the invention, one example of a method as taught by Hayenga et al. and employed by the invention for focussing will now be further described. As described above with reference to FIGS. 1A, 1B and 1C, the motion controller 504 includes a stage for receiving the slide 1 and is responsive to a slide scan signal, received from a processor 540, for moving the stage in a slide plane represented by X and Y directions. In the illustrative diagram of FIGS. 1A, 1B and 1C, the X and Y directions are located in the plane that is perpendicular to an optical path intermediate the slide 1 and the condenser 402. The motion controller 504 is further responsive to a slide focus signal for moving the slide 1 in a direction normal to the slide plane, along the optical path 110, for focusing the camera upon the slide 1. The motion controller 504 is constructed to provide a position signal to the processor 540 wherein the position signal is indicative of the X, Y, and Z position of the slide 1. Motion controllers for performing the above-described functions are known in the art and a suitable motion controller may be selected by those skilled in the art.

The camera assembly 512 is constructed to provide an image signal indicative of the optical transmissivity of the specimen on the slide 1. The image signal from the camera assembly 512 is obtained by focusing the camera assembly 512 on a focal point positioned a first distance along the optical path 110. The camera assembly 512 is further constructed to provide an above focus image signal and a below focus image signal, referred to herein as a focus plus and a focus minus signal, respectively. The focus plus signal is provided by focusing the camera assembly on a focal point positioned a second distance along the optical path 110 wherein the length of the second distance is greater than the length of the first distance. The focus minus signal is provided by focusing the camera assembly on a focal point positioned a third distance along the optical path 110 wherein the length of the third distance is less than the length of the first distance. The image signal, focus plus signal, and focus minus signal are each provided to the processor 540.

The processor 540 uses the focus plus signal and the focus minus signal to determine the positioning of the slide 1 along the optical path 110 necessary for focusing the specimen so that the image signal provided by the camera 512 will be in focus. More particularly, the processor 540 determines whether the received signal is of a magnitude large enough to focus, whether the image plane lies within the correctable region, and which direction to move the slide 1 to focus the image.

Figure 29:
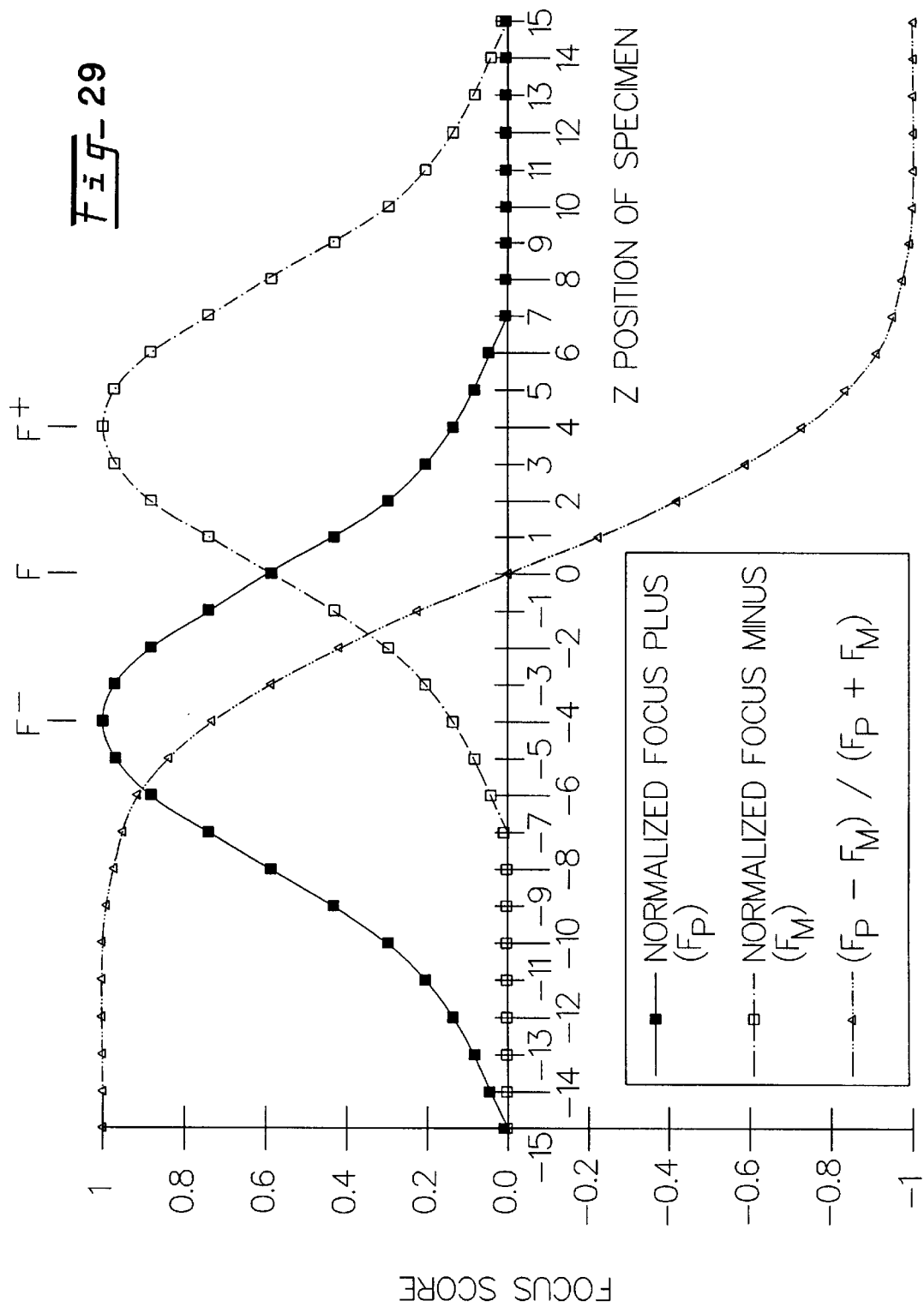
FIG. 29 is a graph illustrating the relationship between the passband frequency component of the signal provided by the camera assembly of FIG. 1A and the focus of the camera assembly.

Generally, the processor 540 determines the magnitude of the band-pass frequency energy in the focus plus and focus minus signals. As illustrated in FIG. 29, the image signal will be in focus when the band-pass frequency energy of the focus plus and focus minus signals are substantially equal. Accordingly, to determine the proper positioning of the slide 1 along the optical path, the processor 540 need only determine how far the slide must be displaced for the energy provided by the focus plus and focus minus signals to be substantially equal. It will be apparent to those skilled in the art that the relative positioning of the focal point of the camera assembly when providing the focus plus signal and focus minus signal is determinative of the relationship between their band-pass frequency energy components and the positioning of the camera assembly for providing a focused image signal.

So that the image signals may be obtained more rapidly, the processor 540 is constructed to provide the scan signal to position the motion controller 504 in a plurality of X-Y positions to obtain a plurality of image signals indicative of a respective plurality of images of a portion of the specimen on the slide 1. The processor 540 may be further constructed to determine the proper positioning of the slide 1 along the optical path for each of the plurality of image signals obtained. After each of the plurality of image signals has been obtained, the processor 540 can determine whether the slide is focused by examining the band-pass frequency component of the focus plus signal and the focus minus signal, as discussed above. If the image signals were not focused, the processor 540 will determine the proper positioning of the slide for focus and will provide the scan signal to the motion controller 504 to re-position the slide 1 in the X-Y positions of the portions not focused and, simultaneously, provide the slide focus signal to the motion controller 504 to obtain the proper positioning of the slide 1 along the optical path so that focused image signals are obtained.

Figure 30:
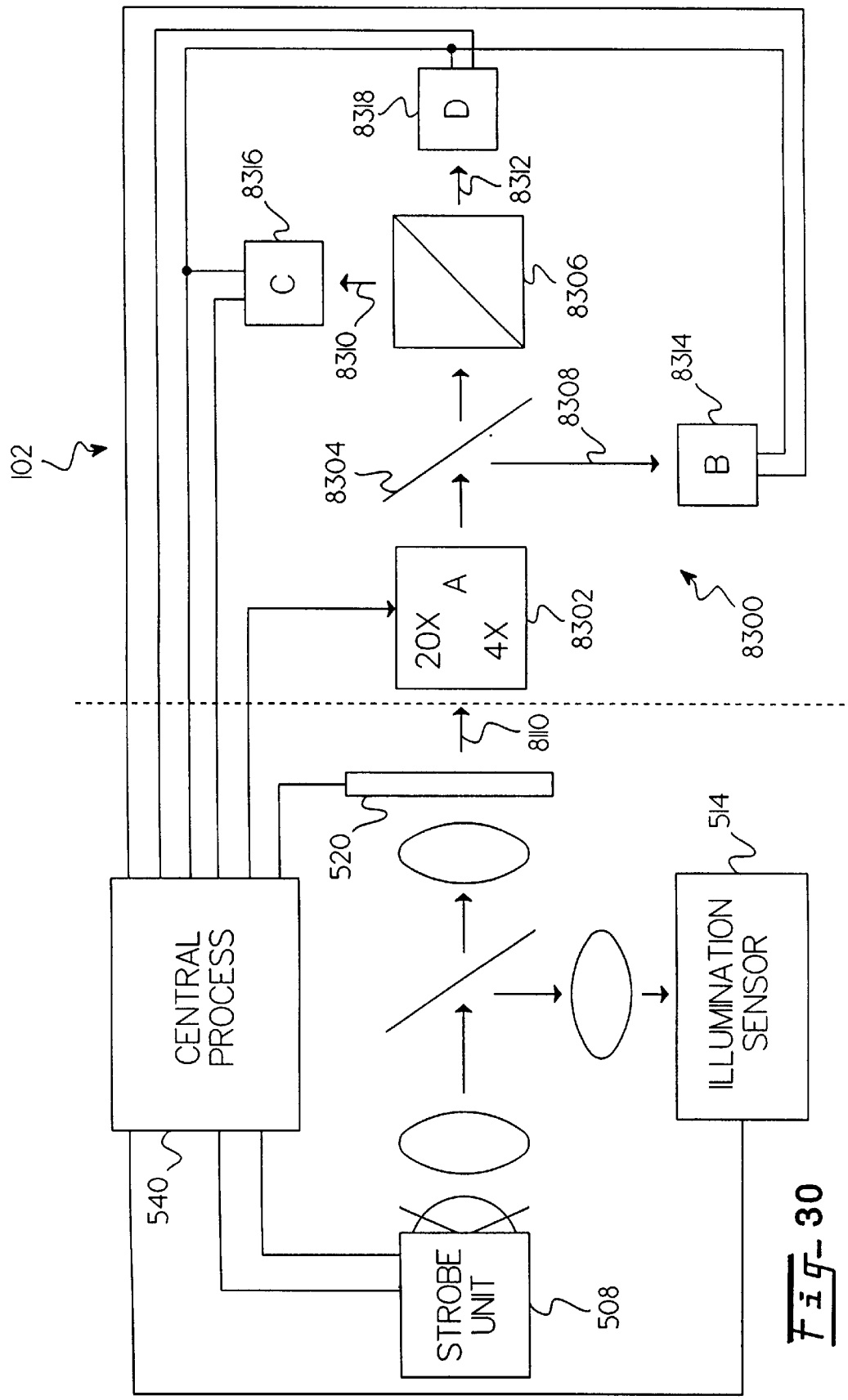
FIG. 30 is a more detailed illustrative diagram of the camera assembly that comprises the subject invention.

A more detailed diagram of the camera assembly 512 is provided in the illustrative diagram of FIG. 30. Therein, an optical transmission assembly 8300 includes an objective lens assembly 8302, a first beam splitter 8304 and a second beam splitter 8306. The first and second beam splitters 8304 and 8306 provide first, second, and third optical paths 8308, 8310, and 8312, respectively. The objective lens assembly 8302 is constructed to vary the magnification provided to the specimen on the slide 1. In a presently preferred embodiment of the invention, the objective lens assembly 8302 is responsive to a magnification signal received from the processor 540 to select various lenses to vary the magnification. Suitable assemblies for responding to an electric signal to move two or more lenses into and out of position for varying the magnification provided to the specimen may readily be provided by those skilled in the art.

A primary camera 8314 is positioned to receive a first image of the specimen on the slide 1 via the first optical path 8308. The first optical path 8308 is the path from point A on the objective 8302 to point B at the CCD of the primary camera 8314. The primary camera 8314 is responsive to an activation signal for providing an image signal representing the first image. A focus plus camera 8316 is positioned to receive a second image of the specimen on the slide 1 along a second optical path 8310. The second optical path 8310 is the path from point A on the objective 8302 to point C on the CCD of the focus plus camera 8316. The length of the second optical path 8310 is less than the length of the first optical path 8110 by a predetermined length. The focus plus camera 8316 is also responsive to the activation signal for providing a focus plus signal, wherein the focus plus signal is indicative of the focus of the image signal. A focus minus camera 8318 is positioned to receive a third image of the object on the slide 1 via a third optical path 8312. The third optical path is the path from point A on the objective 8302 to a point D on the CCD of the focus minus camera 8318. The length of the third optical path 8312 is greater than the length of the first optical path 8308 by the predetermined length. The focus minus camera 8318 is responsive to the activation signal for providing a focus minus signal that is also indicative of the focus of the image signal.

As discussed above, the processor 540 determines the band-pass energy of the focus plus signal and the focus minus signal to determine the proper positioning of the slide 1 so that the image signals will be representative of a focused image of the specimen on the slide. Accordingly, the processor 540 includes first and second identical focus processor circuits 1400 and 1403, as illustrated in FIG. 31. The focus processor circuits 1400 and 1403 each include a band pass filter 1404 and 1406, respectively, for receiving the focus plus and focus minus signals. The band pass filters 1404 and 1406 are constructed to pass a band-pass energy component of the focus plus and focus minus signals. Each filtered signal is multiplied by itself in respective multiplier circuits 1408 and 1410 so that the resulting signal is always proportional to the magnitude of the energy. This energy level signal is then integrated for each line of active video provided in respective integrators 1412 and 1414 to provide signals indicative of the total energy provided in the band-pass. The output from integrators 1412 and 1414 is sampled by respective sample and hold circuits 1416 and 1418 before being digitized by an analog-to-digital convertor 1420. The processor 540 uses the signals from the analog-to-digital convertor 1420 to determine the proper positioning of the slide 1 so that the image signals provided by the primary camera 8314 will be representative of a focused image.

In operation, the processor 540 receives an array of focus plus scores FP(0), FP(1), . . . FP(255), and array of focus minus scores FM(0), FM(1), . . . FM(225), each including 256 elements, one for each line of a particular field of the camera 512. The focus plus and focus minus arrays provide video signals to the focus processor which are used to calculate the focus score. Only the first field of the interlaced video image is used to calculate the focus score so that the acceptability of the image may be determined while the second field is still being received from the camera. In this manner, the focus score is available before the entire image is received. Each line of the image is processed through bandpass filters and the energy is integrated and measured by the analog-to-digital converters.

In order to further understand the filter selection process of the invention, refer to FIG. 32 where a schematic view of a typical cell is shown. A cell 900 comprises cell cytoplasm 902 and a cell nucleus 904. Typical cell nuclear sizes for pap smears range in area from about 40 micrometers squared to 220 micrometers squared. Typical nuclear diameters range from about 4 micrometers to 10 micrometers. In one example embodiment of the invention where the magnification of interest is 20×, pixel size is 0.55 micrometers per pixel.

Now referring to FIG. 33, a process for converting physical cell size into electrical band width is schematically illustrated. The conversion from physical size into electrical band width may be accomplished by using the known pixel clock rate from the camera. In this example, the pixel clock rate is $14.1875 \times 10^6$ pixels per second. From the pixel clock rate, the physical size of a cell nucleus may be translated into a time varying voltage when the camera images the cell nucleus. This technique is well known in the art. The pixel time in one example of the invention is about $70.5 \times 10^{-9}$ seconds. The target for the focus system is between 7 and 19 pixels in size. Because some spreading of the object size occurs due to defocused images being used as the stimulus to the cameras for measuring focus, the size range is increased slightly. The focus system may advantageously be made sensitive to objects having a size of from 7 to 22 pixels. A nucleus sectioned by a video camera scan line 906 has a time varying modulation 908 in the electrical domain, which correlates to its size in the spatial domain. The relationship between the spatial domain and electrical domain is illustrated in FIG. 33 which shows the cell 900 having its nucleus 904 scanned by video lines 906. The scanned cell is then translated into electrical voltages as indicated by plot 910 which plots a modulated voltage signal 908 against time.

Figure 34:
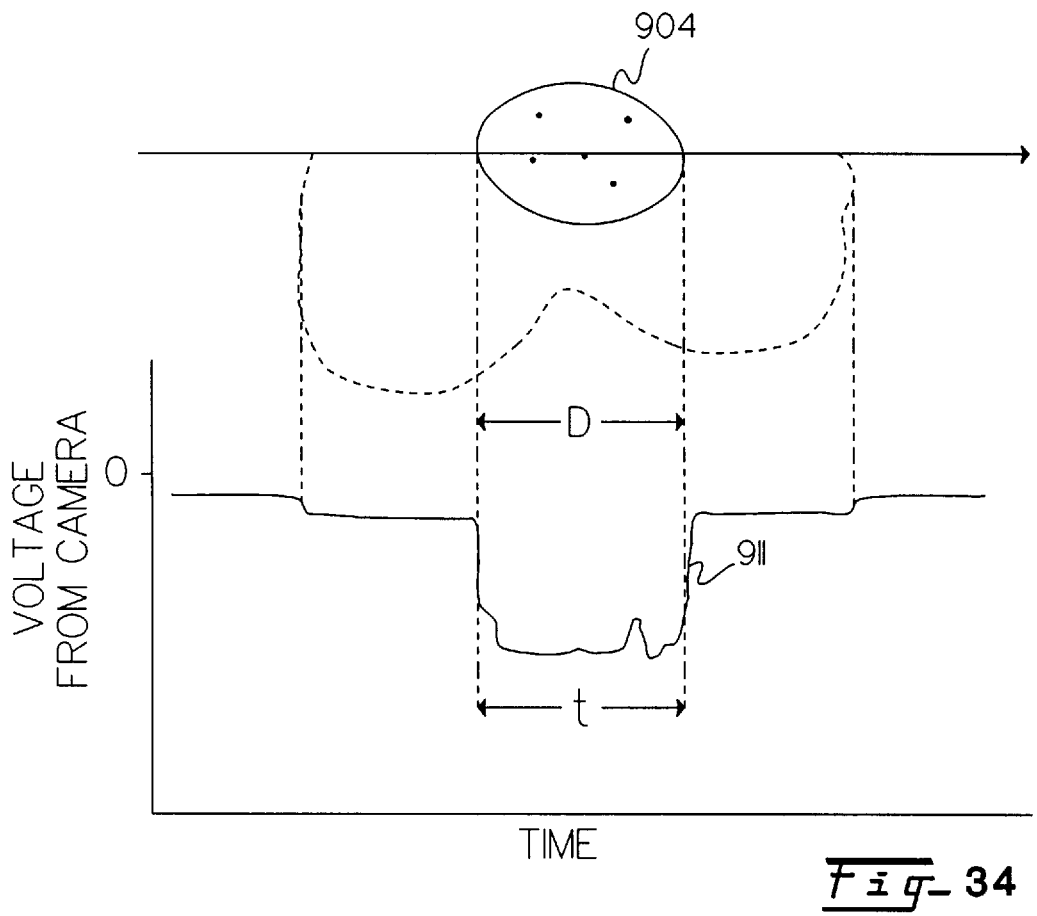
FIG. 34 graphically illustrates a time varying voltage of a dark nucleus.
Figure 35:
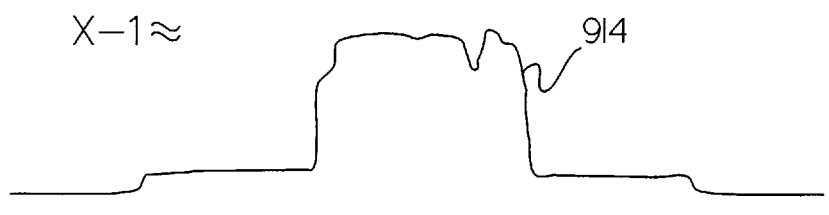
FIG. 35 shows an inverted pulse representing a square function.

Referring now to FIG. 34, a time varying voltage of a dark nucleus is graphically illustrated. The nucleus 904 is analogous to a pulse or square function 911 having an interval, t. In this example, shown for illustrative purposes and not by way of limitation of the invention, the interval t may range from about $493 \times 10^{-9}$ to $1550 \times 10^{-9}$ seconds. FIG. 35 shows an inverted pulse 914 which is inversely related to pulse 911. Fourier transformations for such square functions are well known.

Figure 36:
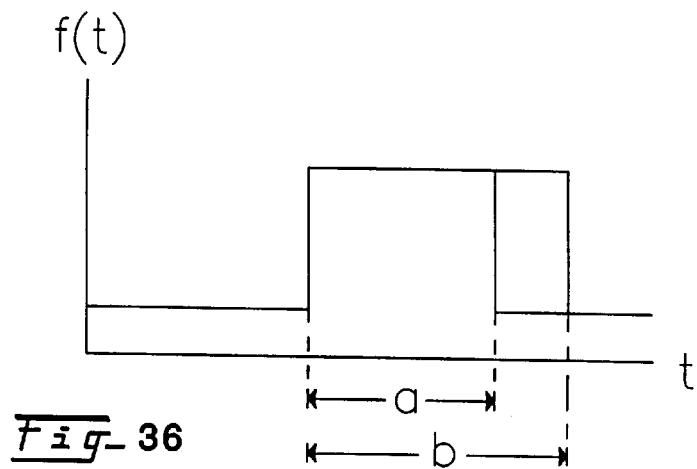
FIGS. 36 and 37 show a Fourier transformation for a square function as employed in one aspect of the invention.
Figure 37:
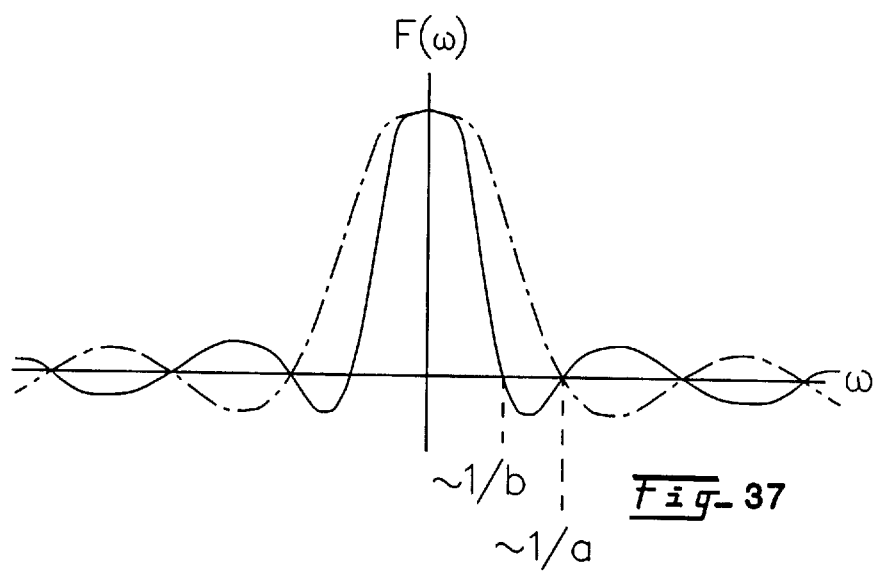

Referring now jointly to FIGS. 36 and 37, a Fourier transformation for a square function is illustrated as employed in one aspect of the invention. Where a is the smallest nucleus and b is the biggest nucleus, the focus transformation of such pulses then represent spectral energy of objects of the particular size of interest. Using the Fourier representation of these objects, a spectral filter may be chosen which is sensitive to objects in this size range.

Figure 38:
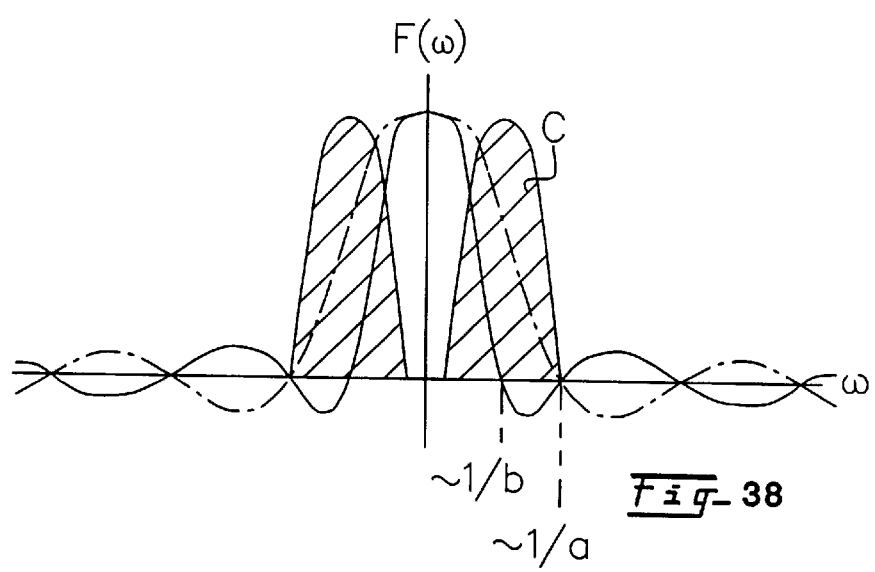
FIG. 38 illustrates a filter response sensitive to objects of interest, such as cell nuclei as employed in one embodiment of the invention.

Referring now to FIG. 38, filter response sensitive to objects of interest, such as cell nuclei, is schematically illustrated. Filter response C may be selected so that the focus system is sensitive to cell nuclei in the size range of interest. Once having the benefit of knowing the filter response desired for objects in the range of interest as taught by the present invention, a band pass filter may then be designed using conventional techniques.

Next, a filter operation is performed on each of the four arrays FP, FM, FPnoise, and FMnoise in order to reduce sensitivity to objects that are smaller than the desired cells that are to be focused on. The filter operation is sensitive to the vertical size of objects, whereas the band pass filter on the video lines are sensitive to the horizontal size of objects. Accordingly, the system is sensitive to the two dimensional size of objects in the focus system. This provides an improved focus and improves signal-to-noise ratio.

The filter operation can be expressed as follows:

$$[FP(0) \ldots FP(255)]*[Ffk(0) \ldots Ffk(4)] \Rightarrow [XFPS(2) \ldots XFPS(253)]$$

$$[FM(0) \ldots FM(255)]*[Ffk(0) \ldots Ffk(4)] \Rightarrow [XFMS(2) \ldots XFMS(253)]$$

The focus plus and focus minus array are each convolved with a filter array Ffk to correlate the energies of adjacent lines. The filter array Ffk is selected to provide a low pass filter that looks for objects at least five lines in size. The filter array Ffk is selected to provide a finite impulse response, low pass filtering of the focus plus and focus minus arrays. The filter kernel is designed to be sensitive to the size and type of object that the processor 540 is attempting to detect. Further, the finite impulse response filtering is performed in a manner so that the resulting filter array eliminates the first and last few elements of the respective focus plus and focus minus array to eliminate edge effects from the filter.

After filtering the focus plus and focus minus arrays, filtered focus plus and focus minus arrays, XFPS and XFMS, respectively, are created with each array including 252 elements. The filtered focus scores are further combined with a noise array to eliminate noise that may be provided by the camera system 512. More particularly, the camera system 512 may include noise that results from camera noise, integrator leakage, dust or streaks on the focus camera, or in one of the optical image planes. To eliminate this noise, a noise array is generated and combined with the filtered focus scores. The noise array is generated by focusing the camera 512 upon a white field, i.e., one with no slide 1 so that the focus plus and focus minus camera can measure the fixed noise floor energy within the focus filter band pass. The blank image is viewed in order to obtain a measure of the fixed noise patterns that will stimulate the focus processor. The noise arrays of raw focus scores obtained from viewing the blank image are represented as: [FPnoise(0) . . . FPnoise(255)] for the focus plus array; and, [FMnoise(0) . . . FMnoise(255)] for the focus minus array. The noise floor integration is relatively consistent and can be measured and subtracted from the energy measurements made for the individual line scores. This significantly improves the signal to noise ratio for each line.

In this regard, a noise plus and noise minus array is measured for the focus plus and focus minus cameras 8316, 8318 in the same manner as the focus plus and focus minus signals, discussed above. The noise plus and noise minus arrays include an element for each line of the focus plus and focus minus arrays, respectively. The noise plus and noise minus arrays are convolved with the filter array Ffk, as discussed above with the focus plus and focus minus arrays, to provide filtered noise plus and filtered noise minus arrays, FPNX and FMNX, respectively. The resulting arrays are filtered noise plus and filtered noise minus arrays, having a one-to-one correspondence with the focus plus and focus minus arrays, respectively. The filter operation on the noise arrays are expressed as follows:

[FPnoise(0) . . . FPnoise(255)]*[Ffk(0) . . . Ffk(4)]⇒[FPNX(2) . . . FPNX(253)]

[FMnoise(0) . . . FMnoise(255)]*[Ffk(0) . . . Ffk(4)]⇒[FMNX(2) . . . FMNX(253)]

The filter operations are a convolution, shown in the above equations by the asterisk symbol. The 2 elements on each end of the filtered arrays are excluded since the convolution operation is not defined for the elements on each end of the array. The filtered noise plus and noise minus arrays, FPNX and FMNX are correspondingly subtracted from the filtered focus plus and focus minus arrays, XFPS and XFMS, to provide respective focus plus and focus minus signal arrays, FPS and FMS. This improves the S/N ratio. The noise value can be as much as 10%–50% of the total signal. Since the noise is static and repeatable, it can be removed with this method. The noise reduced arrays are as follows:

[XFPS(2) . . . XFPS(253)]−[FPNX(2) . . . FPNX(253)]=FPS[(2) . . . (253)]

[XFMS(2) . . . XFMS(253)]−[FMNX(2) . . . FMNX(253)]=FMS[(2) . . . (253)]

The individual elements of the focus plus signal and the focus minus signal arrays are now combined to provide an array of focus scores FS. Now, lines 2 through 253 have scores which are noise reduced and related to the two dimensional characteristics of above and below focus images. Each line from the above and below cameras represents a measure (in 2D) of the image frequency content. An array of focus scores can now be calculated as follows:

$$FS[(2)\ldots(253)] = \frac{FPS[()\ldots()] - FPM[()\ldots()]}{FPS[()\ldots()] + FPM[()\ldots()]}$$

This step produces a normalized focus score for each line of the camera 512, except the first and last few lines that were excluded because of edge filter effects, as discussed above. Normalization of the focus scores helps to make the data independent, i.e., tends to make each score comparable to one another regardless of the amount of data used to produce the score. This operation normalizes the focus scores to values somewhere between −1 and +1, to create a spatially distributed set of focus scores.

After the focus plus signal array and focus minus signal array have been combined as discussed above to produce an array of focus scores, the array of focus scores is screened to eliminate those scores for which insufficient data existed to achieve a meaningful score. This is done by eliminating each score FS(x) for which FPS(x) plus FMS(x) is outside the range of a predetermined threshold. The threshold range is selected empirically by the lowest signal content image of interest. In a preferred embodiment of the invention, the range is selected to be between 3 and 240. Those skilled in the art will appreciate, however, that this range is only illustrative and that any range, including the full range, may be selected. In one embodiment, favorable results may be obtained using between 1% and 95% of the range. The FS values that qualify are then averaged to yield a single focus score evaluation for the image. This single focus score is a number between −1 and +1 which has a one-to-one correspondence with the distance necessary to move to put the image into best average focus.

In one aspect of the invention, a focus quality score, FQS(x), may be provided. The focus quality score comprises the average of FPS(x) plus FMS(x). The focus quality score indicates the signal level of the image and thereby provides a confidence level for the focus score. If the focus quality score is below a predetermined level, the focus score is not accepted as a reliable focus indicator.

After the focus score has been obtained a look up table is consulted for determining the distance and direction of movement along the optical path necessary to bring the object into focus. As noted above, a particularly novel aspect of the subject invention is the ability of the processor 540 to not only determine whether an image is in focus or out of focus, and not only determine the direction necessary to move the specimen to bring the image into focus, but to also determine the distance of motion necessary to bring the specimen into focus. By determining the exact displacement, and direction of displacement, necessary to bring the specimen into focus, the processor 540 may control the motion controller 504 to rapidly return to the position of any out of focus specimen and may provide the appropriate scan signal so that the motion controller will position the specimen to be in focus.

To determine the amount of displacement, a look up table comprising predetermined correction factors for a given set of optics is employed prior to obtaining any image signals. The correction factors may be derived empirically, for a each set of optics, using known methods. The correction factors in the look up table represent the distance necessary to move an object into focus. Since the focus scores relate to distance, the correction factors may be related to focus scores. When deriving the correction factors, a test image is employed and placed on the motion controller. In a presently preferred embodiment of the invention, a calibration to determine the displacement and direction correlation to focus scores is performed only once when the system is designed and remains the same so long as the component parts of the system are not disturbed. However, those skilled in the art will appreciate that the calibration to obtain data correlating the focus scores to the amount and direction of displacement may be performed at any time prior to obtaining image signals.

Using the above-described apparatus, focused image signals may be obtained in a very rapid manner. In a presently preferred embodiment of the invention, the motion controller 504 positions the slide 1 at a plurality of predetermined positions for obtaining image signals. After each image signal is obtained, the motion controller 504 immediately moves to obtain the next image signal. While the motion controller 504 is positioning the slide 1 to obtain the next image signal, the processor 540 determines whether the last obtained image signal was in focus. Accordingly, there is a 60 millisecond delay between the time that the image is taken and the time the image it is read out of the processor 540. If the last obtained image was in focus, processor 540 identifies the image signal as a focused image signal for use by the remainder of the system. However, if the image signal was not in focus, the processor 540 determines the displacement and direction necessary for focus of the specimen. Thereafter, the processor 540 instructs the motion controller 504 to return to the out of focus image and provides the necessary displacement information so that, when next obtained, the image will be in focus.

A novel modulation transfer function test is explained in detail in U.S. Pat. No. 5,581,631 ibid. This patent is hereby incorporated by reference.

Figure 40A:
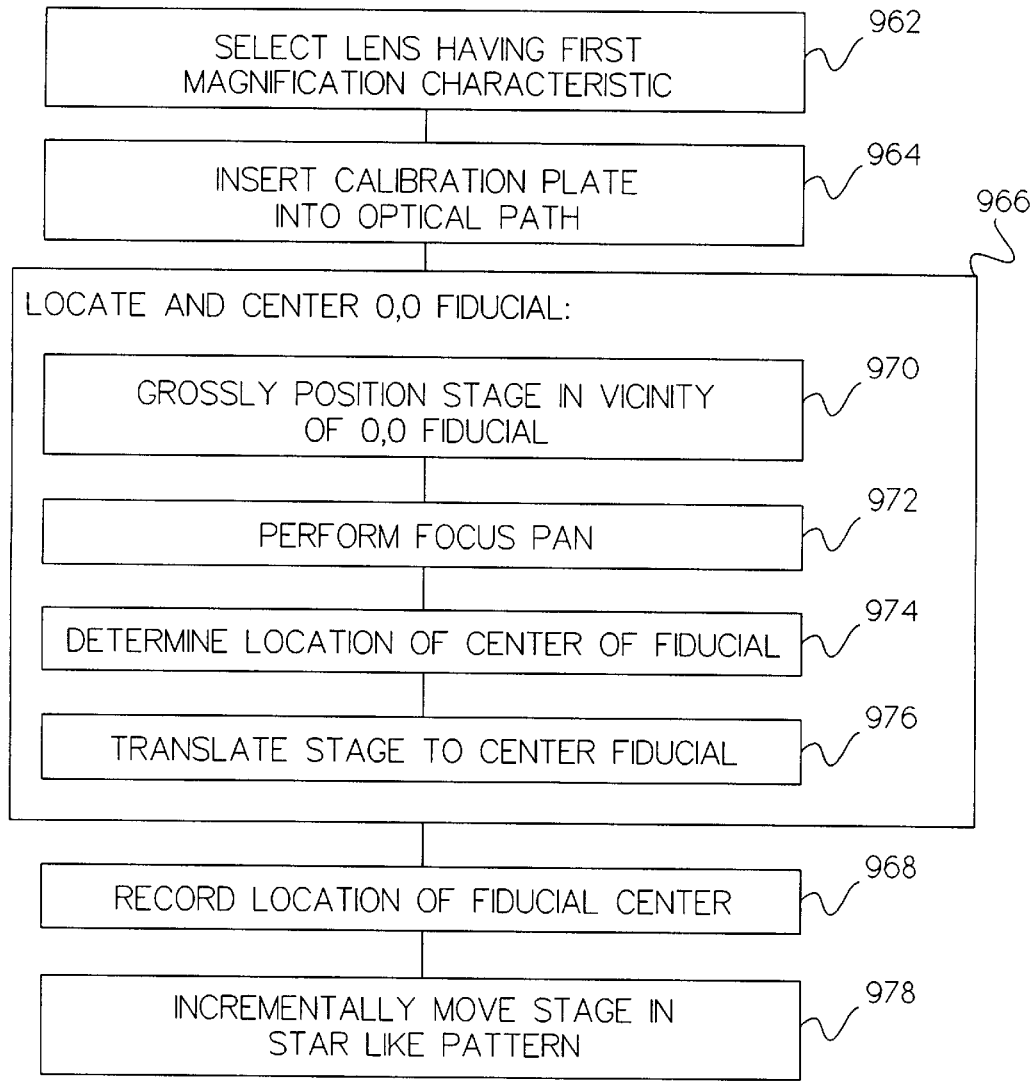
FIGS. 40A and 40B show a flow diagram of one method of the invention for checking stage movement repeatability.
Figure 40B:
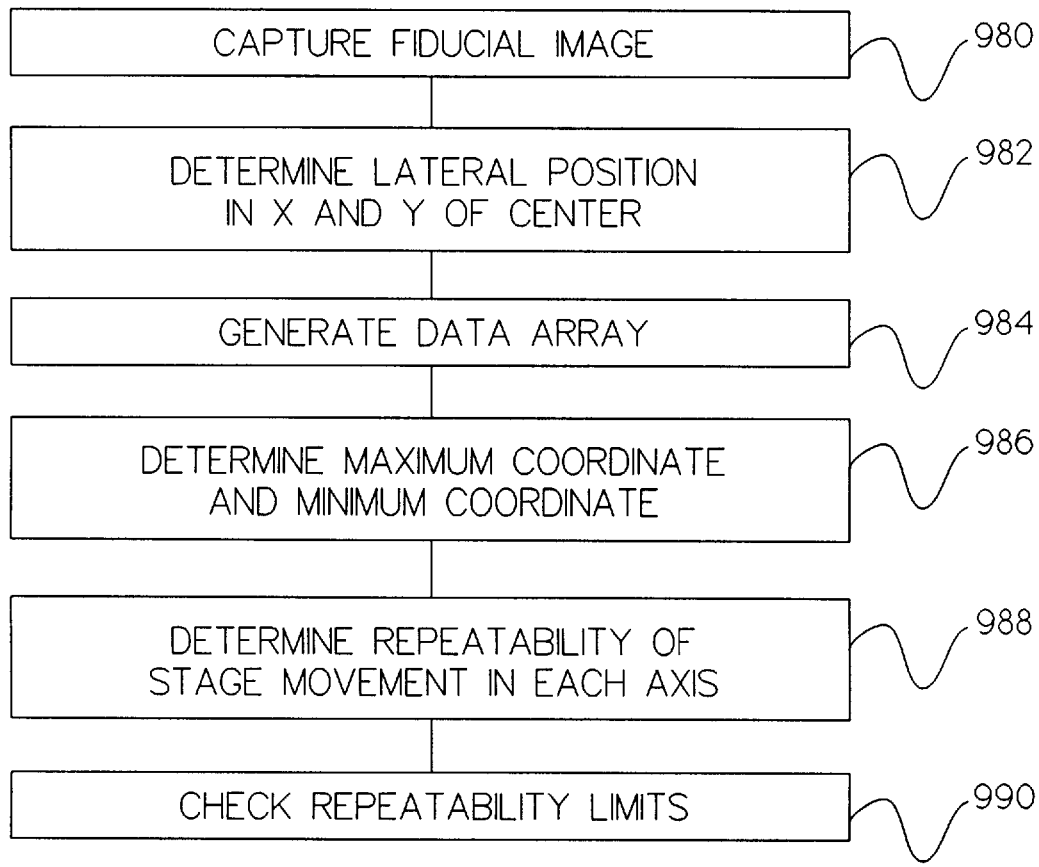

Referring now to FIGS. 40A and 40B, a flow diagram of one method of the invention for checking stage movement repeatability is shown. At step 962 an objective lens of a first magnification power is selected. In one example, a 20×magnification is selected. At step 964 the calibration plate is inserted into the optical path as shown, for example, in FIG. 1C, and the 0,0 fiducial, best shown in FIG. 13B is located and centered in the microscope's field of view at step 966. Generally, step 966 may comprise a number of process substeps for grossly positioning the stage in the vicinity of the 0,0 fiducial as shown at substep 970, performing a focus pan at substep 972, determining the location of the center of the fiducial with respect to the optical axis (or camera center) at substep 974 and translating the stage in the X and Y plane to center the fiducial in the field of view at substep 976.

In one example of the invention, a focus pan 972 may comprise the steps of moving the stage in the Z direction to an estimated focus position followed by incrementally moving towards a position of best focus while acquiring images at each position. The images acquired during the focus pan are processed for focus features, such as high frequency content. The stage continues to move incrementally until the position of best focus has been passed, that is the focus features cease to improve. The stage is then returned to the position of best focus. Other methods are known by those skilled in the art to perform a focus pan.

At step 968, the location of the fiducial center is recorded. At step 978 the stage is moved in a star like pattern first in a direction away from the center of the field of view, then in a direction returning the fiducial to the center of the field of view.

Figure 39:
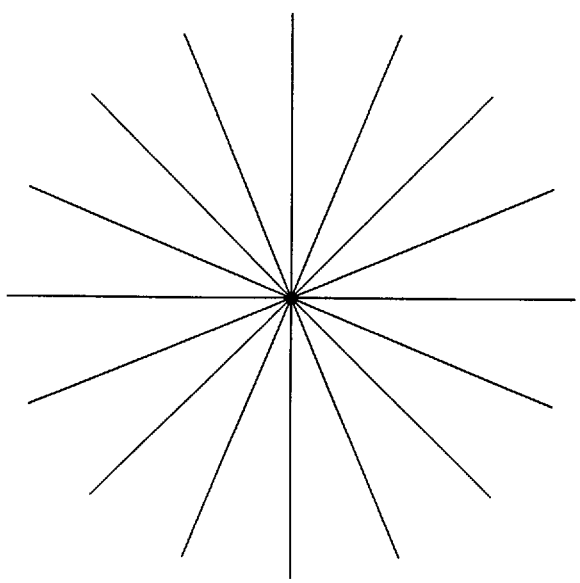
FIG. 39 shows an example of a scan pattern of a point on the XY stage used by one method of the invention.

In one example, the stage is automatically moved so as to move the fiducial away from and then back to the center of the field of view on a 1.5 mm radius in 15 degree increments for twenty four repetitions. The motion profile appears to be a star like pattern as shown in FIG. 39.

The basic premise of the method of the invention is to move the fiducial so as to approach a predetermined position from multiple directions to determine the multidirectional repeatability of the system. The process continues with step 980 where, each time the stage returns to the central position, the fiducial image is captured by the camera. At step 980 the fiducial image is captured by the camera and the coordinates of the fiducial image are recorded. The recorded coordinate information is used to determine the lateral position in the X and Y plane of the center of the fiducial with respect to the optic axis at step 982. In addition, at step 984, the Z position of the image is also determined using the focus apparatus described in allowed U.S. patent application Ser. No. 08/302,355, for which the issue fee has been paid, filed Sep. 7, 1994, entitled "Method and Apparatus for Rapid Capture of Focused Microscopic Images," as described herein with reference to FIGS. 29–38. A difference in Z position from iteration to iteration represents a cross coupling of motion into the Z axis from an X-Y move. At step 984 a data array is generated comprising the X, Y and Z coordinate for each iteration of the test. The array is read to determine the maximum and minimum coordinate 986 in each of the X, Y and Z axes for each of the incremental movements following the star like pattern. The absolute value of the difference between each of the corresponding maximum and minimum coordinates is used to determine the repeatability of stage movement in each axis 988.

The method of the invention is superior to linear encoders or interferometric methods because repeatability is determined exactly at the point of interest. Other methods infer position based on a device that is remotely located from the point of interest. In addition the method of the invention allows a quick check of stage performance between processing operations performed by the machine being tested with no special instrumentation needed. Table 20 shows the output of the test including the limits 990 for test parameters.

TABLE 20

X/Y Repeatability and Z Cross Coupling Test

| Parameter | Result | Limit |
|---|---|---|
| X repeatability: | 3299 | <15000 nm |
| Y repeatability: | 2200 | <15000 nm |
| Z cross coupling | 111 | <2000 nm |

Z Repeatability Test

Figure 41A:
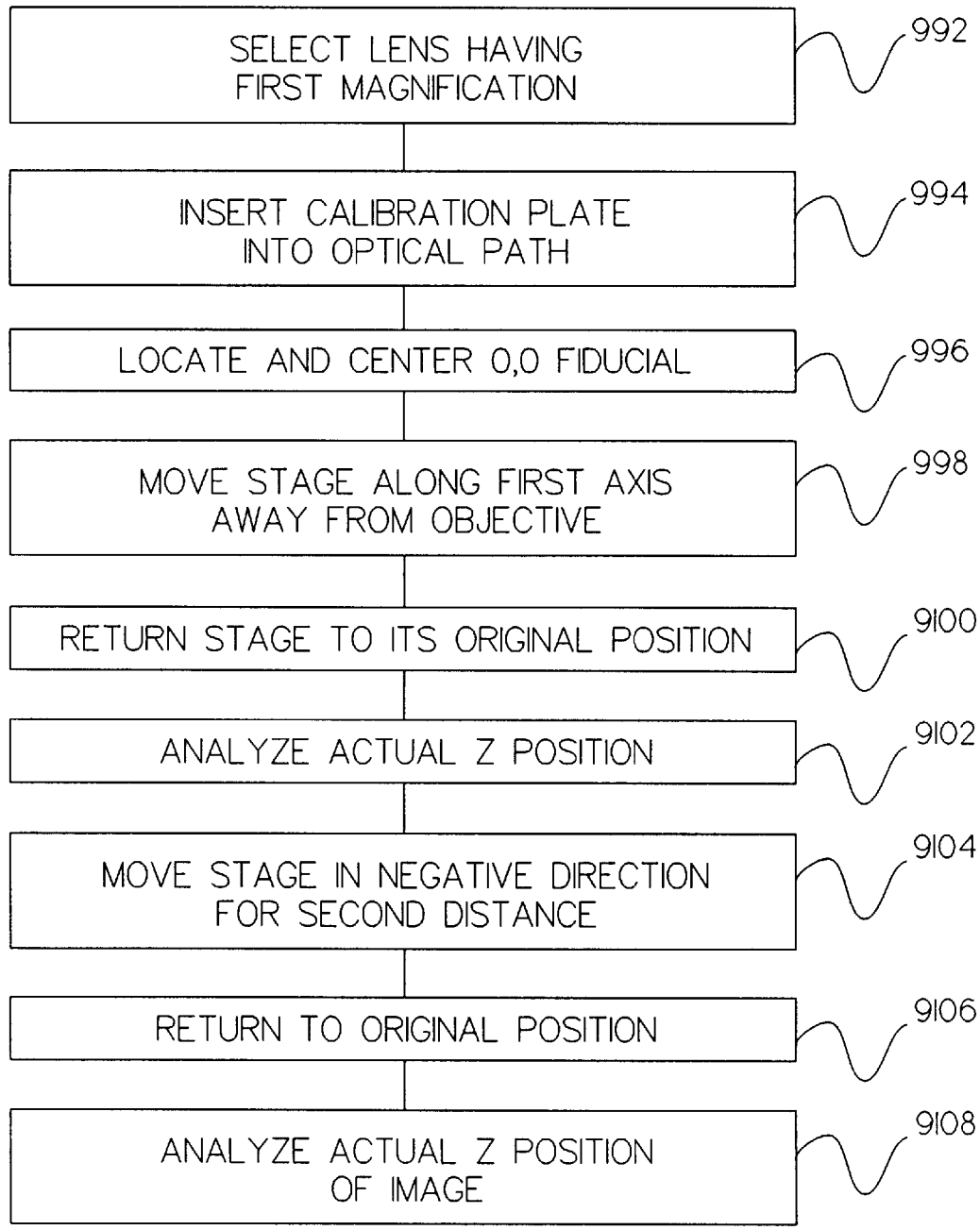
FIGS. 41A and 41B show a flow diagram of one method of the invention for checking repeatability of movement along a Z axis.
Figure 41B:
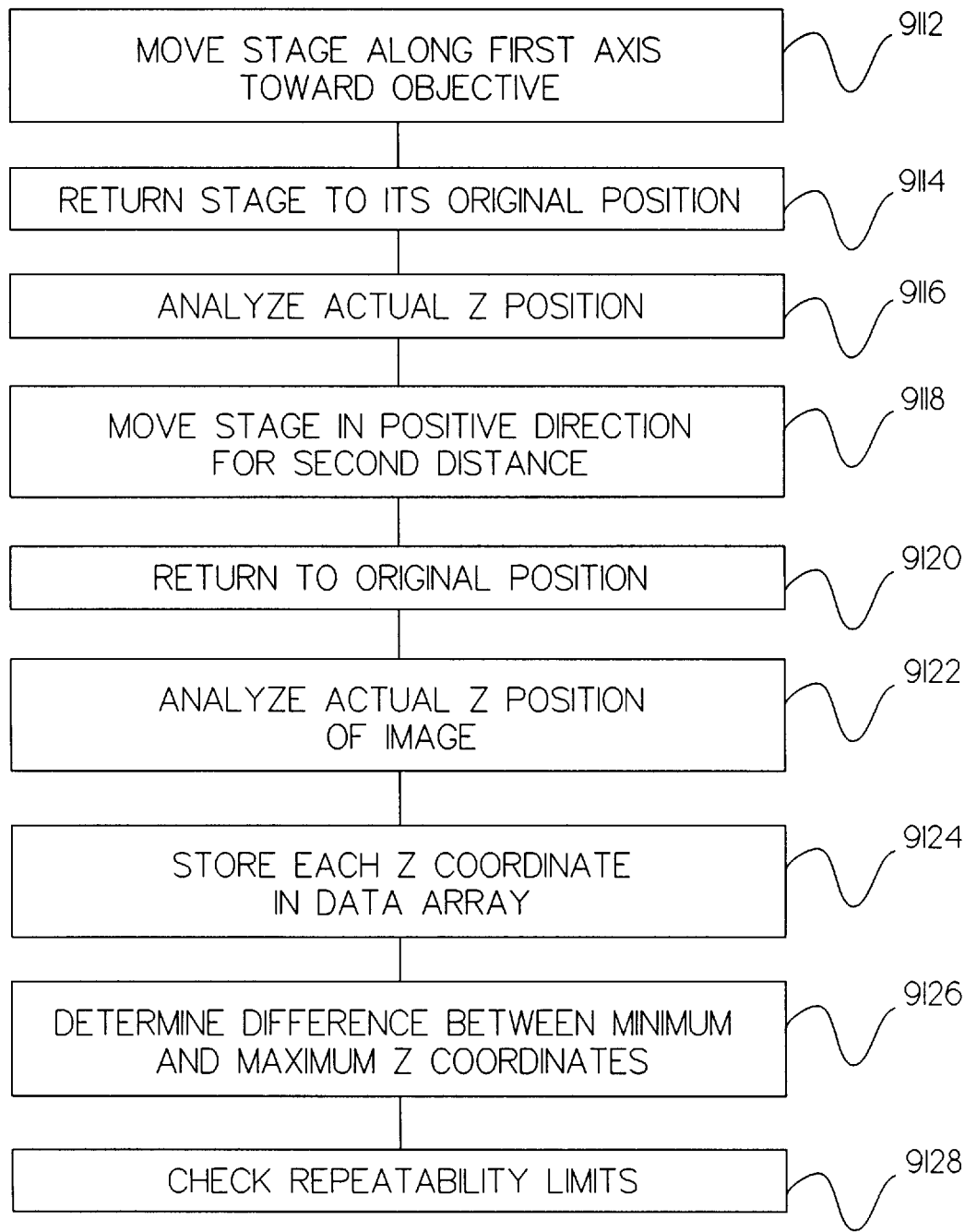

Refer now to FIGS. 41A and 41B where a flow diagram of one method of the invention for checking repeatability of movement along a Z axis is shown. Repeatability in Z influences the speed of processing of an automated microscopy instrument. This is due to the manner in which the instrument collects images for processing. When an image does not have suitable focus for processing, a projection of best focus is made and the image is returned to the queue to be collected later. When the system returns to that image the focus projection is applied. If the stage has poor repeatability of movement along the Z axis relative to the focus error budget, the system may move to the incorrect position, thereby requiring numerous iterations developing a new focus projection, replacing the image back into the queue and reattempting to correctly position the image to finally attain acceptable focus. This increases the time to process the slide. The Z repeatability test as run in accordance with the present invention characterizes this error.

Process steps 992, 994 and 996 set up the test and are similar to those as above described above with reference to FIG. 40A with respect to process steps 962, 964 and 966 respectively. As above, in one example an objective lens having a 20×magnification is selected and a fiducial 0,0 is focused and centered in the field of view to establish an origin. At step 998 the stage is moved in a negative direction, where a negative direction is considered to be a direction away from the microscope objective. In one useful example, the stage is moved along the Z axis a first distance of about 10 microns. At step 9100 the stage is returned to the origin. After returning, the actual Z position is analyzed at step 9102 using the autofocus method and apparatus as described herein. At step 9104 the stage moved in a negative direction equal to a second distance. In the example described herein the second distance may be about 100 microns. As before, at step 9106 the stage returns to the origin. The image is again processed for Z position at step 9108.

The process is repeated again in the positive Z direction beginning at step 9112 where the stage is moved along the Z axis in a positive direction (that is, toward the microscope objective) a third distance. At step 9114 the stage is returned to origin and the actual position of the fiducial along the Z axis is measured at step 9116. At step 9118 the stage is moved in a positive direction for a fourth distance. At step 9120 the stage is returned to the origin. After returning, the actual Z position is again analyzed at step 9122 using the autofocus method and apparatus as described herein.

Then the process is repeated again in both directions, each time the Z coordinate is stored at step 9124. The multiple distance moves are incorporated to ensure the repeatability in move length independent. After all iterations have been completed, the data array is processed to determine the difference between the minimum and maximum Z coordinate 9126. An absolute value of the difference is taken as the repeatability of the Z stage 9128. Some results of this test have been generated for the NeoPath system and are shown in Table 21.

TABLE 21

Z Repeatability

| Parameter | Result | Limit |
|---|---|---|
| Z repeatability: | 149 | <2000 nm |

Turret Repeatability Test

Figure 42:
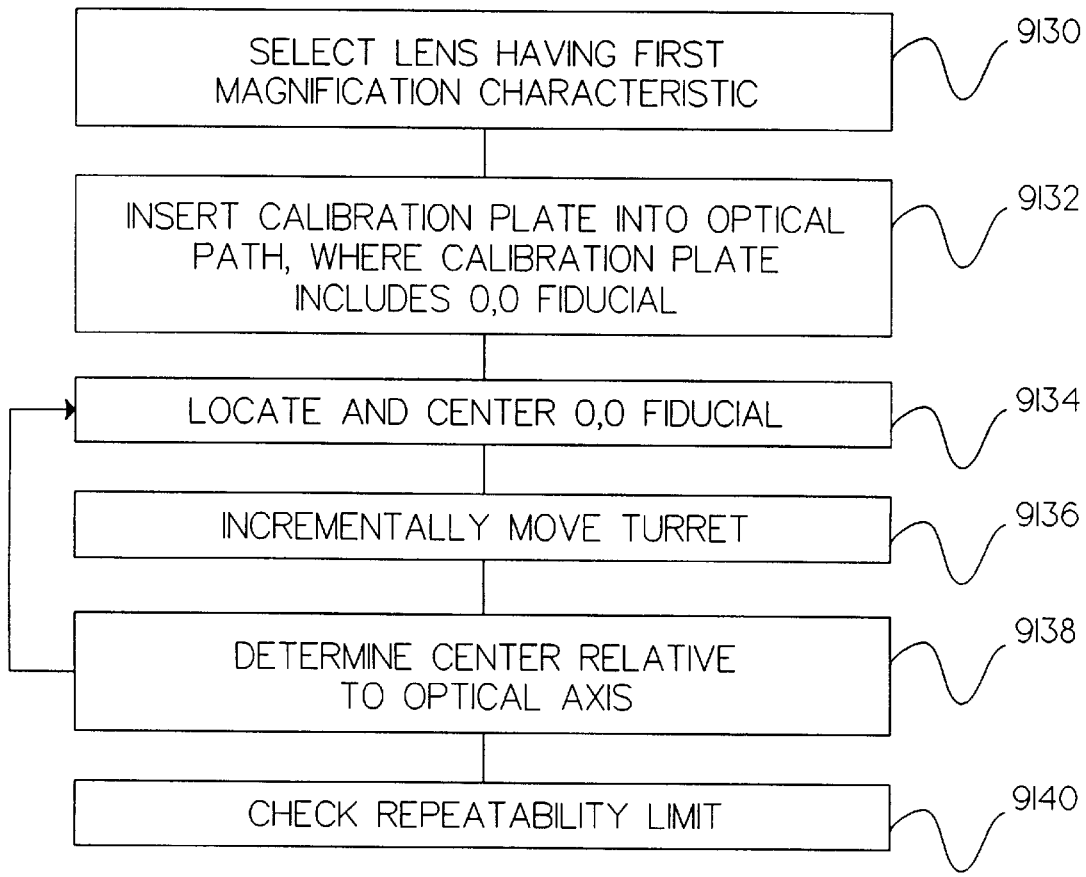
FIG. 42 shows a flow diagram of one method of the invention for checking repeatability of turret movement.

Refer now to FIG. 42 showing a flow diagram of one method of the invention for checking repeatability of turret movement. In a similar fashion to the checks for stage repeatability in the X,Y plane, turret movement repeatability may also effect the efficacy of an automated microscope based instrument. Therefore, the invention provides a turret repeatability test. The system is set up as before. In this case however, the XY and Z stage remains stationary and the turret 22 is moved out of and back into position. The turret positioning movement is repeated six times, each time alternating between clockwise and counter clockwise directions. As described above, at step 9130 an objective lens of a selected magnification characteristic is used. At step 9132 a calibration plate is inserted into the optical path and, at step 9134, each time the turret is moved back into position, an image of fiducial 0,0 is acquired. The image is processed at step 9138 to determine the center in the X, Y plane relative to the optical axis of the microscope. In one example, a 6×2 array is developed of X and Y coordinates for each of the six iterations. The maximum and minimum extent are determined for each axis. An absolute value of the largest difference is taken as the turret repeatability which is checked against limits at step 9140. The results are shown in Table 22.

TABLE 22

Turret Repeatability

| Parameter | Result | Limit |
|---|---|---|
| Turret repeatability: | 1650 | <7000 nm |

Objective Centration and Parfocality Test

Figure 43:
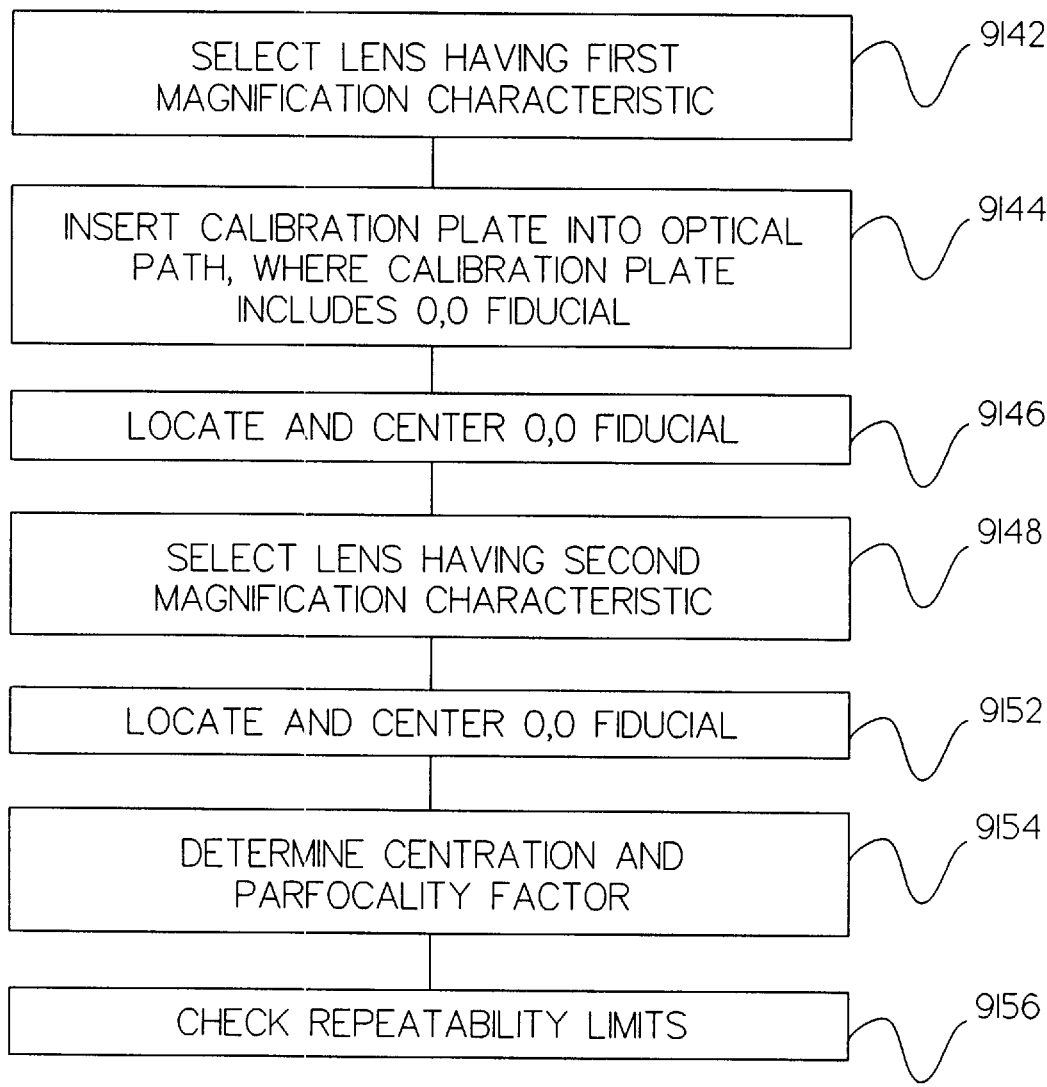
FIG. 43 shows a flow diagram of one method of the invention for checking objective centration and parfocality.

Refer now to FIG. 43 where a flow diagram of one method of the invention for checking objective centration and parfocality is shown. Multiple objectives are typically used in an automated microscope based instrument to vary the magnification. Each objective has its own optical axis, that is to say each objective looks at a certain area of the specimen. It is necessary to make these optic axes collinear such that the center of the image in one objective is very close to the center of another objective when it is placed in position. In addition, it is advantageous to make the focal planes coplanar. A test is performed to ensure that the optic axes of each objective are collinear and the focal planes are coplanar.

Process steps 9142, 9144 and 9146 set up the test and are similar to those as above described above with reference to FIG. 40A with respect to process steps 962, 964 and 966 respectively. As above, in one example an objective lens having a 20×magnification is selected and a fiducial 0,0 is focused and centered in the field of view to establish an origin. At step 9148, a second objective is selected having a second magnification characteristic. In one example, the system is reconfigured to the 4×magnification and the center of the fiducial is found and focused. At step 9152, the 0,0 fiducial is again located and centered. The X, Y and Z coordinates are compared to those of the first selected objective. The X and Y difference is taken as the centration of the objectives and the Z difference is taken as the parfocality at step 9154. The results are compared against limits at step 9156 as seen in Table 23.

TABLE 23

Centration and Parfocality

| Parameter | Result | Limit |
|---|---|---|
| Centration 4X to 20X | 4400 | <25000 nm |
| Parfocality 4X to 20X | 750 | <15000 nm |

Power Supply Limits
Test Description
The processor will query the ICF to check power supply test points once per tray.
Limits

| | |
|---|---|
| Flash Reference | 196–204 |
| +15V/−5.5V | 134–150 |
| +5V/−15V | 169–188 |
| +5.5V/−5.2V | 118–133 |

Failure Response
Stop processing slides and call for service.
4×Frequency Response
The same factors that influence 20×frequency response may also affect the 4×frequency response.
Test Description
The same test described above with reference to FIGS. 40A and 40B is run under 4×magnification with the following exceptions. First, the MTF focus pan starts at 25 microns below the nominal focus position and ten steps of 5 microns each are taken during the pan. Second, the MTF data is only calculated for the center of the field; any field related frequency response problems will be detected by the 20×test.

Limits

4×Vertical Frequency Response

| Frequency Limits | | Minimum MTF |
|---|---|---|
| min | max | center |
| 0.0 | 0.0 | 0.83 |
| 48.5 | 51.0 | 0.85 |
| 148.0 | 150.0 | 0.62 |

4×Horizontal Frequency Response

| Frequency Limits | | Minimum MTF |
|---|---|---|
| min | max | center |
| 0.0 | 0.0 | 0.83 |
| 48.5 | 51.0 | 0.62 |
| 148.0 | 150.0 | 0.08 |

Failure Response

Failure for any 4×condition requires the illumination adjustment of the 4×ND wheel position and 4×pixel gain and offset calibration.

Pixel Correction Gain and Offset

Although pixel correction can reduce patterning in the CCD and static illumination variation, it can also mask problems in these areas as well. Therefore, a check of the pixel gain and offset buffers is made to determine if any corrections are in error.

Test Description

A histogram is generated for the gain and offset buffers and the standard statistical computations are made.

Limits

Pixel Gain

Mean: 2.60<x<2.87

Coefficient of Variation: x<3.60

Maximum: x<3.30

Minimum: x>2.50

Pixel Offset

Mean: 100.0<x<160.0

Coefficient of Variation: x<3.0

Maximum x<180.00

Minimum: x>80.00

Failure Response

Failure for any 20×condition requires the illumination adjustment of the 20×ND wheel position and 20×pixel gain and offset calibration.

Failure for any 4×condition requires the illumination adjustment of the 4×ND wheel position and 4×pixel gain and offset calibration.

Cal-Plate Tilt

Most System Integrity and calibration routines make use of the resolution targets on the cal-plate. Hence the cal-plate must be properly positioned for these routines to be valid. A cal-plate tilt test is performed to ensure that the pitch and roll positioning of the cal-plate arm is within limits.

Test Description

The 50 lp/mm vertical bar target is positioned under the objective and a MTF focus pan is performed separately for the top and bottom regions of the field-of-view to find the best focus position for each region. The difference in the focus positions are taken to determine the pitch of the cal-plate. To determine the roll, a MTF focus pan is performed for the left and right regions of the 50 lp/mm horizontal bar target. The difference between the left and right in-focus positions is reported as the roll.

Limits

Cal-Plate Pitch: <1500 nm

Cal-Plate Roll: <1500 nm

Illumination and Pixel Calibration

Illumination Adjustment

A fundamental component of System Integrity is to ensure that the camera is illuminated to its full dynamic range. This helps the system to achieve an optimal signal to noise ratio. The camera meets an NTSDC criteria that specifies a video dynamic range to be 710 ±20 mV at full white. For concerns of linearity and tolerances, it is possible to adjust a fully illuminated clear field over a nominal thickness glass slide to a camera output voltage of 680 ±10 mV. Adjustment to the illuminator neutral density wedge is made using feed back from the ICF as it measures video signal amplitude.

Once the correct illumination level is achieved, the strobe sensor average value is recorded for maintenance at 4×magnification.

Adjustment Limits

| Camera voltage | 680 ± 10 mV. |
|---|---|
| Sensor Limit | 130 < sensor reading < 230 |

Failure Response

Failure to achieve the sensor or camera limits indicates that the system requires servicing the imaging system.

4×Pixel Offset and Gain Adjustment

Camera and electronic offsets are compensated for on every pixel. This ensures the integrity of low level measurements by controlling the fixed error summed into the video signal.

The gain of each pixel is adjusted to modify the sensitivity of the ICF so that the next measurement of the white field will place the averaged pixel values between 125.5 and 135.5 counts. The standard deviation of the averaged image should be less than 0.6 counts. The difference between the minimum and maximum pixel intensities in the averaged white images cannot exceed 7 counts.

The strobe is turned off and an image averaged 32 times is acquired. The offset is adjusted so that the next measurement of the dark field will place the average pixel values between 4.5 counts and 5.5 counts. The standard deviation of the averaged image should be less than 0.2 counts. The difference between the minimum and maximum pixel intensities in the averaged dark images cannot exceed 4 counts.

The pixel adjustment process is repeated for gain and offset if necessary. If the above limits are not all met after 5 attempts then a fatal error is returned.

Adjustment Limits

| 50% Image Amplitude Average | 130 ± 0.5 counts |
|---|---|
| 50% Image Std Dev | <0.6 counts |
| 50% Image Histogram Width | ≦7 counts |
| Black Image Amplitude Average | 5 ± 0.5 counts |
| Black Image Std. Dev. | <0.2 counts |
| Black Image Histogram Width | ≦4 counts |
| Iteration Attempts | ≦5 |

Failure Response
  Failure requires processing to stop
20×Focus, Illumination and Pixel Calibration
  20× Illumination Adjustment
  A fundamental component of System Integrity is to ensure that the camera is illuminated to its full dynamic range. This helps the system to achieve an optimal signal to noise ratio. The camera meets an NTSC criteria that specifies a video dynamic range to be 710 ±20 mV at full white. For concerns of linearity and tolerances, a fully illuminated blank field is adjusted over a nominal thickness glass slide to a camera output voltage of 680 ±mV. Adjustment to the illuminator neutral density wedge is made using feedback from the ICF as it measures video signal amplitude.
  Once the correct illumination level is achieved the strobe sensor average value is recorded for maintenance at 20×magnification.
  Adjustment Limits

| | |
|---|---|
| Camera voltage | 680 ± 10 mV |
| Sensor Limit | 130 < sensor reading < 230 |

Failure Response
  Failure to achieve the sensor or camera limits indicates that the system requires servicing the imaging system.
20×Pixel Offset Adjustment
  Camera and electronic offsets are compensated for on every pixel. These insure the integrity of low level measurements by controlling the fixed error summed into the video signal.
  The gain of each pixel is adjusted to modify the sensitivity of the ICF so that the next measurement of the white field will place the averaged pixel values between 125.5 and 135.5 counts. The standard deviation of the averaged image should be less than 0.6 counts. The difference between the minimum and maximum pixel intensities in the averaged white images cannot exceed 7 counts.
  The strobe is turned off and an image averaged 32 times is acquired. The offset is adjusted so the next measurement of the dark field will place the averaged pixel values at 4.5 and 5.5 counts. The standard deviation of the averaged image should be less than 0.2 counts. The difference between the minimum and maximum pixel intensities in the averaged dark images cannot exceed 4 counts.
  The pixel adjustment process is repeated for gain and offset if necessary. If the above limits are not all met after 5 attempts then return a fatal error.
Adjustment Limits

| | |
|---|---|
| 50% Image Amplitude Average | 130 ± 0.5 counts |
| 50% Image Std Dev | <0.6 counts |
| 50% Image Histogram Width | ≦7 counts |
| Black Image Amplitude Average | 5 ± 0.5 counts |
| Black Image Std. Dev. | <0.2 counts |
| Black Image Histogram Width | ≦4 counts |
| Iteration Attempts | ≦5 |

Failure Response
  Failure requires processing to stop.
20×Focus NoiseTable Adjustment
  The focus scores processed for the focus− and focus+ cameras are subject to an integrator that sums processed image content on each line of the first field of video. The camera and integrator will have temperature variation dependencies. Dust and particulate may also collect on imaged surfaces and corrupt the focus camera scoring. The "no signal level" of response from this circuit must be monitored for changes. If changes are small a new table of noise floor values can be created during calibration.
Adjustment Limits

| | |
|---|---|
| Focus + Noise Scores | all lines < 10 counts |
| Focus − Noise Scores | all lines < 10 counts |

Failure Response
  Failure requires processing to stop.
20×to 4×Centration Adjustment
  The alignment between the 4×and 20×objectives is a key factor in accurately locating objects of interest. It is very important that the center of the 20×image be very nearly the same as the 4×image center. The XY error between image centers can be compensated for by offsets in the X and Y dimensions when objectives are changed. The calculated center of a test image is used to measure the error and apply corrective offsets.
  The number of adjustment attempts should be no more than 3.
Adjustment Limits

| | |
|---|---|
| 20x to 4x x-error | <7.5 μm |
| 20x to 4x y-error | <7.5 μm |
| 20x to 4x x-offset | <35 μm |
| 20x to 4x y-offset | <35 μm |
| Iterations Attempts | ≦3 |

Failure Response
  Failure requires processing to stop.
  The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An on-line, automated method, capable of performing biological specimen analysis without any operator intervention, of checking processing integrity for an automated biological specimen analysis system wherein the analysis of a biological specimen comprises measuring a feature of the biological specimen, the method comprising the steps of:

(a) measuring an automated biological specimen analysis system parameter with a computer, wherein the automated biological specimen analysis system parameter relates to the processing integrity of the automated biological specimen analysis system to measure the feature;

(b) comparing the automated biological specimen analysis system parameter to a limit to check processing integrity with the computer;

(c) repeating steps (a) and (b) at regularly defined intervals while the automated biological specimen analysis system remains on line; and (d) stopping the automated biological specimen analysis system if the biological specimen analysis system parameter is not within the limit.

2. The method of claim 1 further comprising the step of terminating operation of the automated biological specimen analysis system if the at least one system parameter exceeds the limit.

3. The method of claim 1 further comprising the step of invalidating output of the automated biological specimen analysis system with a computer if the at least one system parameter exceeds the limit.

4. The method of claim 1 wherein the biological specimen analysis system performs at least one recalibration if the at least one system parameter exceeds the limit.

5. An on-line, automated method, capable of performing biological specimen analysis without any operator intervention, for checking biological analysis system processing integrity for an automated biological analysis system wherein the analysis of a biological specimen comprises measuring a feature of the biological specimen, the automated method comprising the steps of:

(a) performing a system calibration with a computer;

(b) performing a set of subsystem integrity checks at regular, predefined intervals to obtain an integrity measure with the computer while the automated biological specimen analysis system remains on line, wherein a condition of a subsystem affects the processing integrity of the automated biological specimen analysis system to measure the feature; and (c) determining a system status with the computer.

6. The automated method of claim 5 wherein the step of performing a system calibration further comprises the step of terminating system operation if the system status indicates a failure condition.

7. The automated method of claim 5 wherein the step of performing a set of subsystem integrity checks further comprises the steps of:

(a) checking processing quality;

(b) checking illumination quality;

(c) checking image collection quality;

(d) checking focus quality; and (e) checking position quality.

8. The automated method of claim 7 wherein the step of checking processing quality comprises:

(a) checking image transfer and processing; and (b) checking power supply limits.

9. The automated method of claim 7 wherein the step of checking illumination quality comprises:

(a) checking global illumination variation;

(b) checking static field uniformity;

(c) checking dynamic field uniformity;

(d) checking slide thickness variation;

(e) checking cal plate dirt check;

(f) checking strobe variation; and (g) checking strobe drop out monitor.

10. The automated method of claim 7 wherein the step of checking collection quality comprises:

(a) checking system linearity;

(b) checking modulation transfer function for at least one magnification;

(c) checking image collection signal to noise; and (d) checking correction gain and offset for at least one pixel.

11. The automated method of claim 7 wherein the step of checking focus quality comprises:

(a) checking focus illumination;

(b) checking focus noise floors;

(c) checking focus filter frequency response;

(d) checking at least one focus camera modulation transfer function;

(e) checking focus camera longitudinal separation;

(f) checking focus camera lateral and angular offsets; and (g) checking closed loop focus accuracy.

12. The automated method of claim 7 wherein the step of checking position quality further comprises:

(a) testing at least one position repeatability;

(b) checking turret repeatability;

(c) checking calibration plate tilt; and (d) checking at least one magnification surface sense parfocality and centration.

13. The automated method of claim 5 wherein the step of performing a system calibration with a computer further comprises the steps of:

(a) calibrating illumination and pixel parameters for at least one magnification; and (b) calibrating mechanical parameters.

14. The automated method of claim 13 wherein the step of calibrating illumination and pixel parameters of at least one magnification comprises:

(a) performing illumination adjustment; and (b) performing offset and gain adjustment for at least one pixel.

15. The automated method of claim 13 wherein the step of calibrating mechanical parameters comprises:

(a) performing a parfocal and centration calibration adjustment between a plurality of magnifications; and (b) performing a parfocal calibration between at least one magnification and a surface sensor.

16. The automated method of claim 5 wherein the step of performing a set of subsystem integrity checks further comprises the steps of:

(a) checking processing quality;

(b) checking image transfer and processing;

(c) checking power supply limits;

(d) checking illumination quality;

(e) checking global illumination variation;

(f) checking static field uniformity;

(g) checking dynamic field uniformity;

(h) checking slide thickness variation;

(i) checking cal plate dirt check;

(j) checking strobe variation;

(k) checking strobe drop out monitor;

(l) checking collection quality;

(m) checking system linearity;

(n) checking 20×frequency response;

(o) checking 4×frequency response;

(p) checking collection signal to noise;

(q) checking pixel correction gain and offset;

(r) checking focus quality;

(s) checking focus illumination;

(t) checking focus noise floor;

(u) checking focus filter frequency response;

(v) checking focus camera frequency response;

(w) checking focus camera longitudinal separation;

(x) checking focus camera lateral and angular offsets;

(y) checking closed loop fiducial focus test;

(z) checking position quality;

(aa) x,y repeatability;

(ab) checking turret repeatability;

(ac) checking cal plate tilt;

(ad) checking 4×, 20×, surface sense parfocality and centration;

(ae) checking 4×illumination and pixel calibration;

(af) checking 4×illumination adjustment;

(a,g) checking 4×pixel offset and gain adjustment;

(ah) checking 4×illumination adjustment;

(ai) checking 4×pixel offset and gain adjustment;

(aj) checking 20×focus, illumination and pixel calibration;

(ak) checking 20×illumination adjustment;

(al) checking 20×pixel offset and gain adjustments;

(am) checking 20×focus noise table adjustments;

(an) checking mechanical parfocal and centration calibration;

(ao) checking 4×to 20×parfocal and centration adjustments; and (ap) checking 20×to surface sense adjustment.

17. An on-line, automated method, capable of performing biological specimen analysis without any operator intervention, of checking processing integrity for an automated biological specimen analysis system wherein the analysis of a biological specimen comprises measuring a feature of the biological specimen, the method comprising the steps of:

(a) calibrating the automated biological specimen analysis system with a computer;

(b) performing a system calibration to provide a calibration parameter, wherein the calibration parameter relates to the processing integrity of the biological specimen system to measure the feature, with a computer;

(c) repeating steps a) and b) a predetermined number of times if the at least one calibration parameter exceeds at least one predetermined limit until the at least one calibration parameter is within the at least one predetermined limit; and (d) indicating that the automated biological specimen analysis system is unsuitable to analyze the biological specimen if the predetermined number of times has been exceeded and the at least one calibration parameter exceeds the at least one predetermined limit, and otherwise passing the system.

18. The method of claim 17 further comprising the step of failing a previous group of specimen results if the system fails.

19. The method of claim 17 further comprising the step of validating a previous group of specimens if the system passes the integrity check.

20. The method of claim 17 wherein the system calibrates and performs an integrity check during power up.

21. The method of claim 17 wherein the system performs an integrity check between each group of specimens.

22. The method of claim 21 wherein the system calibrates if necessary between each group of specimens.

23. The method of claim 1 wherein trays containing slides of biological specimens are loaded into the automated biological analysis system and the automated biological analysis system produces results for each tray, the method further comprising the steps of:

(a) invalidating the results for a tray if the biological specimen analysis system parameter is not within the limit; and (b) validating the results for a tray if the biological specimen analysis system parameter is within the limit.

* * * * *